United States Patent
Magnuson et al.

(10) Patent No.: US 8,338,594 B2
(45) Date of Patent: Dec. 25, 2012

(54) PYRROLOTRIAZINE DERIVATIVES USEFUL FOR TREATING CANCER THROUGH INHIBITION OF AURORA KINASE

(75) Inventors: Steven Magnuson, Dublin, CA (US); Julie Dixon, Bethany, CT (US); Barton Phillips, New Haven, CT (US); Uday Khire, Orange, CT (US); Lei Wang, Milford, CT (US); Zhonghua Zhang, Ridgefield, CT (US); Manoj Patel, Berlin, CT (US); Ellalahewage Sathyajith Kumarasinghe, Franklin, MA (US); Philip Wickens, Richmond Hill (CA); Alan Olague, Shelton, CT (US)

(73) Assignee: Bayer HealthCare LLC, Tarrytown, NY (US)

( * ) Notice: Subject to any disclaimer, the term of this patent is extended or adjusted under 35 U.S.C. 154(b) by 555 days.

(21) Appl. No.: 12/085,850

(22) PCT Filed: Dec. 1, 2006

(86) PCT No.: PCT/US2006/046082
§ 371 (c)(1),
(2), (4) Date: Oct. 6, 2010

(87) PCT Pub. No.: WO2007/064932
PCT Pub. Date: Jun. 7, 2007

(65) Prior Publication Data
US 2011/0021518 A1  Jan. 27, 2011

Related U.S. Application Data

(60) Provisional application No. 60/742,003, filed on Dec. 2, 2005.

(51) Int. Cl.
*C07D 487/04* (2006.01)
*C07D 401/14* (2006.01)
*C07D 403/14* (2006.01)
*A61K 31/53* (2006.01)
*A61P 35/00* (2006.01)

(52) U.S. Cl. ........................................ 544/183; 514/243

(58) Field of Classification Search .................. 544/183; 514/243
See application file for complete search history.

(56) References Cited

PUBLICATIONS

Cecil Textbook of Medicine, edited by Bennet, J.C., and Plum F., 20th edition, vol. 1, 1004-1010, 1996.*
Freshney et al., Culture of Animal Cells, A Manual of Basic Technique, Alan R. Liss, Inc., 1983, New York, p4.*
Dermer et al., Bio/Technology, 1994, 12:320.*
Cohen et al., Current Opinion in Chemical Biology, 3,459-465, 1999.*
Golub et al., Science, 286, 531-537, 1999.*
Mass, R. D., Int. J. Radiation Oncology Bio. Phys.vol. 58(3): 932-940, 2004.*
Fabbro et al. Pharmacology & Therapeutics 93, 79-98, 2002.*
Gautschi et al., Clin. Cancer Res., 14(6), 1639-1648, 2008.*
Mountzios et al., Cancer Treatments Reviews, 34, 175-182, 2008.*

* cited by examiner

*Primary Examiner* — Venkataraman Balasubramanian

(57) ABSTRACT

This invention relates to novel compounds and processes for their preparation, methods of treating diseases, particularly Cancer, comprising administering said compounds, and methods of making pharmaceutical compositions for the treatment or prevention of disorders, particularly Cancer.

14 Claims, No Drawings

PYRROLOTRIAZINE DERIVATIVES USEFUL FOR TREATING CANCER THROUGH INHIBITION OF AURORA KINASE

FIELD OF THE INVENTION

This invention relates to novel compounds and processes for their preparation, methods of treating diseases, particularly Cancer, comprising administering said compounds, and methods of making pharmaceutical compositions for the treatment or prevention of disorders, particularly Cancer.

BACKGROUND OF THE INVENTION

Dysregulated cellular proliferation, genomic instability and survival are hallmarks of all cancers. Normal cellular regulation is a balance of signals that control cell proliferation and programmed cell death (apoptosis). The interplay between these complex processes maintains tissue stability and function. A loss of regulation of these cellular pathways that control cell cycle progression leads to uncontrolled cell growth and tissue homeostasis.

Cell cycle regulation is controlled through an ordered cascade of protein phosphorylation events. Several families of protein kinases that play critical roles in cell cycle progression have been identified. Interestingly, the activity of many of these kinases is increased in human tumors when compared to normal tissue. Whether this is due to increased levels of expression or protein or by changes in expression of co-activators, the ultimate result is a loss of cell cycle regulation.

The Aurora family (Aurora-A, B, C or 2, 1, 3) are serine/threonine kinases that are essential to the regulation and function of mitosis and cytokinesis (summarized in Adams et al., 2001, Trends in Cell Biology 11 (2): 49-54). The expression and activity of Aurora Kinase is cell cycle regulated such that peak activity occurs during mitosis and expression is nearly undetectable in a resting cell. The catalytic domains of the Auroras are highly conserved, with greater than 90% homology, but have distinct subcellular localizations and functions during mitosis and cytokinesis. Aurora Kinase A is localized to centrosomes and spindle poles in mitosis and is required for centrosome segregation and maturation. In contrast, Aurora-B forms a complex with three other proteins, inner centromere protein (INCENP), borealin and survivin, and behaves as a "mitotic passenger protein" (Meraldip P, et al 2004). This chromosomal passenger protein plays a central role in complex functions to chaperone and regulate mitosis and cytokinesis. The movement of the complex from centromeres to the central spindle during anaphase, to the midbody presumably reflects the requirement of Aurora-B to act on different substrates. A range of substrates has been identified for Aurora Kinase A and B with histone 3, a protein involved in chromatin condensation and mitotic entry, being the best characterized. Finally, Aurora C has been shown to be localized to spindle poles during the late stages of mitosis, however very little is known about its overall function (Kimuram M, et al 1999).

Small molecule inhibitors of Aurora Kinases have provided insight into the overall understanding of the role of Auroras in mitotic regulation (Ditchfield C, et al 2003, Hanning E A, et al 2004, and Carpinelli P, et al 2005). Structurally diverse inhibitors promote the same cellular phenotypes and inhibition of histone 3 phosphorylation on serine 10. Additionally, small molecule inhibitors of Aurora Kinase and antisense oligonucleotides have been demonstrated to have an antiproliferative effect on tumor cells. This indicates that inhibition of Aurora Kinase will be useful in the treatment of cancer.

SUMMARY OF THE INVENTION

In one embodiment, the present invention provides a compound of formula (I)

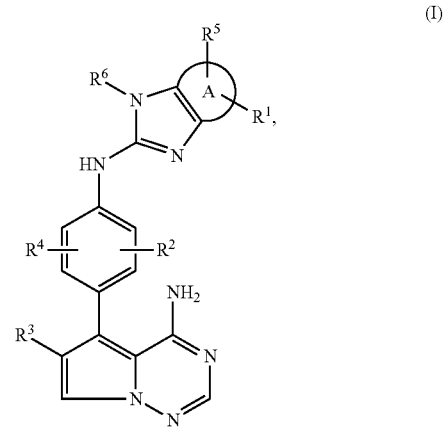

wherein
The A ring denotes a 5 to 7 membered aryl, heteroaryl, heterocyclic or cycloalkyl ring wherein the heteroaryl or heterocyclic rings include 1 to 3 heteroatoms selected from O, N or S;

$R^1$ is selected from the group consisting of hydrogen, halo, alkyl, trifluoromethyl, hydroxy, alkoxy, alkoxyalkyl, trifluoromethoxy, phenyloxy, halophenyloxy, methylphenyloxy, alkoxyphenyl, alkylphenyl, alkoxyalkylphenyl, halothiophenyl, alkylcarbonyl, nitro, cyano, carboxyl, alkoxycarbonyl, benzoyl, alkylamino, alkylaminocarbonyl, alkylaminosutfonyl, cycloalkylamino, cycloaklylalkylamino, benzylamino, alkoxyalkylamino, and heterocyclyl, or $R^1$ is a group

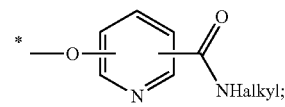

or $R^1$ and $R^5$ together with the carbon atoms to which they are attached, form a 1,3-dioxolane or 1,4-dioxane ring, which can optionally be substituted with 1, 2, or 3 halo;

$R^2$ is hydrogen, halo or methyl;

$R^3$ is

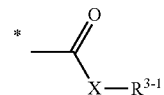

wherein $R^{3-1}$ is hydrogen, alkyl, trifluoroethyl, alkoxyalkyl, cycloalkyl, cycloalkylalkyl, heterocyclylalkyl, dialkylaminoalkyl, hydroxycycloalkyl, and X is —O—, —NH— or —N(alkyl)-, or wherein X and R3-1 are taken together to form a heterocyclyl ring optionally substituted with alkyl, carboxamide, alkoxyalkyl, or dialkylamine;

$R^4$ is hydrogen or halo;

$R^5$ is hydrogen, halo, or alkyl; and $R^6$ is hydrogen or alkyl;

or a pharmaceutically acceptable salt thereof.

In a preferred embodiment, the invention encompasses a compound of claim 1, wherein X is —O—.

In another preferred embodiment, the invention encompasses a compound of formula (I), wherein X is —NH—.

In another embodiment, the invention encompasses a compound of formula (I), wherein $R^{3-1}$ is trifluoroethyl.

In a distinct embodiment, the invention encompasses a compound of formula (I), wherein X and $R^{3-1}$ are taken together to form a heterocyclyl ring optionally substituted with alkyl, carboxamide, alkoxyalkyl, or dialkylamine.

In another preferred embodiment, the invention encompasses a compound of formula (I), wherein $R^2$ is hydrogen and $R^4$ is halogen, preferably fluorine.

In still another preferred embodiment, the invention encompasses a compound of formula (I), wherein $R^6$ is hydrogen.

In another distinct embodiment, the invention encompasses a compound having formula (Ia)

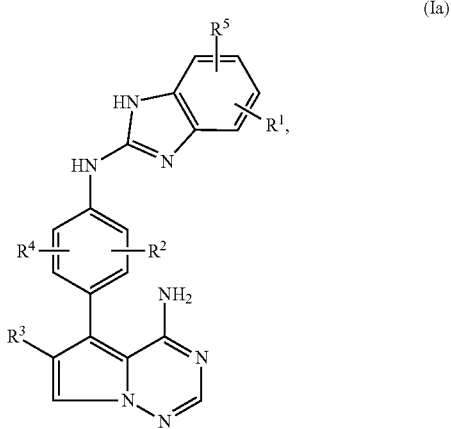

(Ia)

wherein $R^1$ is selected from the group consisting of hydrogen, halo, alkyl, trifluoromethyl, hydroxy, alkoxy, trifluoromethoxy, alkylcarbonyl, cyano, carboxyl, alkoxycarbonyl, alkylaminocarbonyl, alkylaminosulfonyl, and heterocyclyl, or $R^1$ is a group

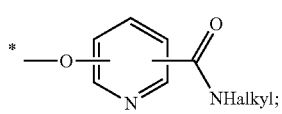

or $R^1$ and $R^5$ together with the carbon atoms to which they are attached, form a 1,3-dioxolane or 1,4-dioxane ring, which can optionally be substituted with 1, 2, or 3 halo;

$R^2$ is hydrogen, halo or methyl;

$R^3$ is

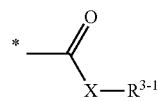

wherein $R^{3-1}$ is alkyl or trifluoroethyl, and X is O or —NH—;

$R^4$ is hydrogen or halo;

$R^5$ is hydrogen, halo, alkyl, or alkoxy;

or a pharmaceutically acceptable salt thereof.

In yet another distinct embodiment, the invention encompasses a compound having the formula:

4-amino-5-[4-(1H-benzimidazol-2-ylamino)phenyl]-N-(2,2,2-trifluoroethyl)pyrrolo[2,1-f][1,2,4]triazine-6-carboxamide;

4-amino-5-{4-[(5-cyano-1H-benzimidazol-2-yl)amino]phenyl}-N-(2,2,2-trifluoroethyl)pyrrolo[2,1-f][1,2,4]triazine-6-carboxamide;

4-amino-5-{4-[(7-hydroxy-1H-benzimidazol-2-yl)amino]phenyl}-N-(2,2,2-trifluoroethyl)pyrrolo[2,1-f][1,2,4]triazine-6-carboxamide;

4-amino-5-{4-[(6-chloro-1H-benzimidazol-2-yl)amino]phenyl}-N-(2,2,2-trifluoroethyl)pyrrolo[2,1-f][1,2,4]triazine-6-carboxamide;

4-amino-N-(2,2,2-trifluoroethyl)-5-(4-{[6-(trifluoromethyl)-1H-benzimidazol-2-yl]amino}phenyl)pyrrolo[2,1-f][1,2,4]triazine-6-carboxamide;

4-amino-5-{4-[(5,7-difluoro-1H-benzimidazol-2-yl)amino]phenyl}-N-(2,2,2-trifluoroethyl)pyrrolo[2,1-f][1,2,4]triazine-6-carboxamide;

4-amino-5-{4-[(6-fluoro-1H-benzimidazol-2-yl)amino]phenyl}-N-(2,2,2-trifluoroethyl)pyrrolo[2,1-f][1,2,4]triazine-6-carboxamide;

4-amino-5-{4-[(6-methoxy-1H-benzimidazol-2-yl)amino]phenyl}-N-(2,2,2-trifluoroethyl)pyrrolo[2,1-f][1,2,4]triazine-6-carboxamide;

4-amino-5-{4-[(6-bromo-1H-benzimidazol-2-yl)amino]phenyl}-N-(2,2,2-trifluoroethyl)pyrrolo[2,1-f][1,2,4]triazine-6-carboxamide;

4-amino-5-{4-[(6-tert-butyl-1H-benzimidazol-2-yl)amino]phenyl}-N-(2,2,2-trifluoroethyl)pyrrolo[2,1-f][1,2,4]triazine-6-carboxamide;

4-amino-5-{4-[(6-benzoyl-1H-benzimidazol-2-yl)amino]phenyl}-N-(2,2,2-trifluoroethyl)pyrrolo[2,1-f][1,2,4]triazine-6-carboxamide;

4-amino-5-{4-[(5,6-dichloro-1H-benzimidazol-2-yl)amino]phenyl}-N-(2,2,2-trifluoroethyl)pyrrolo[2,1-f][1,2,4]triazine-6-carboxamide;

4-amino-5-{4-[(6-chloro-5-fluoro-1H-benzimidazol-2-yl)amino]phenyl}-N-(2,2,2-trifluoroethyl)pyrrolo[2,1-f][1,2,4]triazine-6-carboxamide;

4-amino-5-{4-[(5,6-difluoro-1H-benzimidazol-2-yl)amino]phenyl}-N-(2,2,2-trifluoroethyl)pyrrolo[2,1-f][1,2,4]triazine-6-carboxamide;

4-amino-5-{4-[(6,7-dimethyl-1H-benzimidazol-2-yl)amino]phenyl}-N-(2,2,2-trifluoroethyl)pyrrolo[2,1-f][1,2,4]triazine-6-carboxamide;

4-amino-5-[4-(1H-thieno[3,4-d]imidazol-2-ylamino)phenyl]-N-(2,2,2-trifluoroethyl)pyrrolo[2,1-f][1,2,4]triazine-6-carboxamide;

4-amino-5-{4-[(2,2-difluoro-5H-[1,3]dioxolo[4,5-f]benzimidazol-6-yl)amino]phenyl}-N-(2,2,2-trifluoroethyl)pyrrolo[2,1-f][1,2,4]triazine-6-carboxamide;

4-amino-5-[4-(3H-imidazo[4,5-b]pyridin-2-ylamino)phenyl]-N-(2,2,2-trifluoroethyl)pyrrolo[2,1-f][1,2,4]triazine-6-carboxamide;

4-amino-5-(4-{[6-(4-methoxyphenyl)-1H-benzimidazol-2-yl]amino}phenyl)-N-(2,2,2-trifluoroethyl)pyrrolo[2,1-f][1,2,4]triazine-6-carboxamide;

4-amino-5-{4-[(5-pyrrolidin-1-yl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-[4-(9H-purin-8-ylamino)phenyl]-N-(2,2,2-trifluoroethyl)pyrrolo[2,1-f][1,2,4]triazine-6-carboxamide;

4-amino-5-{4-[(7-methyl-1H-benzimidazol-2-yl)amino]phenyl}-N-(2,2,2-trifluoroethyl)pyrrolo[2,1-f][1,2,4]triazine-6-carboxamide;

4-amino-5-{4-[(6-nitro-1H-benzimidazol-2-yl)amino]phenyl}-N-(2,2,2-trifluoroethyl)pyrrolo[2,1-f][1,2,4]triazine-6-carboxamide;

4-amino-5-{4-[(5-methoxy-3H-imidazo[4,5-b]pyridin-2-yl)amino]phenyl}-N-(2,2,2-trifluoroethyl)pyrrolo[2,1-1,2,4]triazine-6-carboxamide;

4-amino-5-{4-[(6-iodo-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-{4-[(5-chloro-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-{4-[(6-phenoxy-1H-benzimidazol-2-yl)amino]phenyl}-N-(2,2,2-trifluoroethyl)pyrrolo[2,1-f][1,2,4]triazine-6-carboxamide;

4-amino-5-{4-[(5-methyl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-(4-{[6-(4-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-{4-[(6-methyl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-N-(2,2,2-trifluoroethyl)-5-(4-{[6-(trifluoromethoxy)-1H-benzimidazol-2-yl]amino}phenyl)pyrrolo[2,1-f][1,2,4]triazine-6-carboxamide;

4-amino-5-{4-[(7-fluoro-6-phenoxy-1H-benzimidazol-2-yl)amino]phenyl}-N-(2,2,2-trifluoroethyl)pyrrolo[2,1-f][1,2,4]triazine-6-carboxamide;

4-amino-5-{4-[(5-ethoxy-1H-benzimidazol-2-yl)amino]phenyl}-N-(2,2,2-trifluoroethyl)pyrrolo[2,1-f][1,2,4]triazine-6-carboxamide;

4-amino-5-{4-[7-fluoro-6-(4-methylphenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(4-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-{4-[(1-methyl-1H-benzimidazol-2-yl)amino]phenyl}-N-(2,2,2-trifluoroethyl)pyrrolo[2,1-f][1,2,4]triazine-6-carboxamide;

4-amino-5-{4-[(7-fluoro-6-pyrrolidin-1-yl-1H-benzimidazol-2-yl)amino]phenyl}-N-(2,2,2-trifluoroethyl)pyrrolo[2,1-f][1,2,4]triazine-6-carboxamide;

4-amino-5-{4-[(5-phenoxy-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-(4-{[7-fluoro-6-(2-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(3-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(2-methylphenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(3-methylphenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(isopropylamino)-1H-benzimidazol-2-yl]amino}phenyl)-N-(2,2,2-trifluoroethyl)pyrrolo[2,1-f][1,2,4]triazine-6-carboxamide trifluoroacetate;

5-{4-[(6-acetyl-1-methyl-1H-benzimidazol-2-yl)amino]phenyl}-4-amino-N-(2,2,2-trifluoroethyl)pyrrolo[2,1-f][1,2,4]triazine-6-carboxamide;

4-amino-5-{4-[(6-methyl-9H-purin-8-yl)amino]phenyl}-N-(2,2,2-trifluoroethyl)pyrrolo[2,1-f][1,2,4]triazine-6-carboxamide;

4-amino-5-{4-[(5-morpholin-4-yl-3H-imidazo[4,5-b]pyridin-2-yl)-amino]phenyl}-N-(2,2,2-trifluoroethyl)pyrrolo[2,1-f][1,2,4]triazine-6-carboxamide;

4-amino-5-(4-{[5-(cyclobutylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(cyclohexylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(3,4-dimethylphenoxy)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[(3-fluorophenyl)thio]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-[4-({5-[(cyclohexylmethyl)amino]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-(4-{[5-(isobutylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[(2-methoxyethyl)amino]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-(4-{[5-(tert-butylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(propylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[(2-methoxyethyl)(methyl)amino]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-(4-{[5-(cyclopropylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(3,3-difluoropyrrolidin-1-yl)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-{4-[(5,7-difluoro-1H-benzimidazol-2-yl)amino]-3-fluorophenyl}-N-(2,2,2-trifluoroethyl)pyrrolo[2,1-f][1,2,4]triazine-6-carboxamide;

4-amino-5-{4-[(2,2-difluoro-5H-[1,3]dioxolo[4,5-f]benzimidazol-6-yl)amino]-3-fluorophenyl}-N-(2,2,2-trifluoroethyl)pyrrolo[2,1-f][1,2,4]triazine-6-carboxamide;

4-amino-5-{4-[(6-chloro-1H-benzimidazol-2-yl)amino]-3-fluorophenyl}-N-(2,2,2-trifluoroethyl)pyrrolo[2,1-f][1,2,4]triazine-6-carboxamide;

4-amino-5-{3-fluoro-4-[(5-methyl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-{3-fluoro-4-[(5-morpholin-4-yl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-{3-fluoro-4-[(5-pyrrolidin-1-yl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-[3-fluoro-4-(3H-imidazo[4,5-b]pyridin-2-ylamino)phenyl]-N-(2,2,2-trifluoroethyl)pyrrolo[2,1-f][1,2,4]triazine-6-carboxamide;

4-amino-5-{4-[(5-chloro-6-fluoro-1H-benzimidazol-2-yl)amino]-3-fluorophenyl}-N-(2,2,2-trifluoroethyl)pyrrolo[2,1-f][1,2,4]triazine-6-carboxamide;

4-amino-5-[3-fluoro-4-(1H-thieno[3,4-d]imidazol-2-ylamino)phenyl]-N-(2,2,2-trifluoroethyl)pyrrolo[2,1-f][1,2,4]triazine-6-carboxamide;

4-amino-5-{(4-[(5-benzoyl-1H-benzimidazol-2-yl)amino]-3-fluorophenyl}-N-(2,2,2-trifluoroethyl)pyrrolo[2,1-f][1,2,4]triazine-6-carboxamide;

4-amino-5-[3-fluoro-4-(1H-imidazo[4,5-c]pyridin-2-ylamino)phenyl]-N-(2,2,2-trifluoroethyl)pyrrolo[2,1-f][1,2,4]triazine-6-carboxamide;

4-amino-5-{3-fluoro-4-[(7-methyl-1H-benzimidazol-2-yl)amino]phenyl}-N-(2,2,2-trifluoroethyl)pyrrolo[2,1-f][1,2,4]triazine-6-carboxamide;

4-amino-5-{4-[(5,7-difluoro-1H-benzimidazol-2-yl)amino]phenyl}pyrrolo[2,1-f][1,2,4]triazine-6-carboxylic acid;

4-amino-N-(tert-butyl)-5-{4-[(5,7-difluoro-1H-benzimidazol-2-yl)amino]phenyl}pyrrolo[2,1-f][1,2,4]triazine-6-carboxamide;

4-amino-5-{4-[(5,7-difluoro-1H-benzimidazol-2-yl)amino]phenyl}-N-ethylpyrrolo[2,1-f][1,2,4]triazine-6-carboxamide;

4-amino-5-{4-[(5,7-difluoro-1H-benzimidazol-2-yl)amino]phenyl}-N,N-dimethylpyrrolo[2,1-f][1,2,4]triazine-6-carboxamide;

4-amino-5-{4-[(5,7-difluoro-1H-benzimidazol-2-yl)amino]phenyl}-N-(2-methoxyethyl)pyrrolo[2,1-f][1,2,4]triazine-6-carboxamide;

5-{4-[(5,7-difluoro-1H-benzimidazol-2-yl)amino]phenyl}-6-(morpholin-4-ylcarbonyl)pyrrolo[2,1-f][1,2,4]triazin-4-amine;

4-amino-N-cyclobutyl-5-{4-[(5,7-difluoro-1H-benzimidazol-2-yl)amino]phenyl}pyrrolo[2,1-f][1,2,4]triazine-6-carboxamide;

4-amino-N-cyclohexyl-5-{4-[(5,7-difluoro-1H-benzimidazol-2-yl)amino]phenyl}pyrrolo[2,1-f][1,2,4]triazine-6-carboxamide;

4-amino-5-{4-[(5,7-difluoro-1H-benzimidazol-2-yl)amino]phenyl}-N-(3-methylbutyl)pyrrolo[2,1-f][1,2,4]triazine-6-carboxamide;

4-amino-N-(cyclopropylmethyl)-5-{4-[(5,7-difluoro-1H-benzimidazol-2-yl)amino]phenyl}pyrrolo[2,1-f][1,2,4]triazine-6-carboxamide;

1-[(4-amino-5-{4-[(5,7-difluoro-1H-benzimidazol-2-yl)amino]phenyl}pyrrolo[2,1-f][1,2,4]triazin-6-yl)carbonyl]piperidine-4-carboxamide;

4-amino-5-{4-[(5,7-difluoro-1H-benzimidazol-2-yl)amino]phenyl}-N-(3-pyrrolidin-1-ylpropyl)pyrrolo[2,1-f][1,2,4]triazine-6-carboxamide;

4-amino-5-{4-[(5,7-difluoro-1H-benzimidazol-2-yl)amino]phenyl}-N-(3-morpholin-4-ylpropyl)pyrrolo[2,1-f][1,2,4]triazine-6-carboxamide;

4-amino-5-{4-[(5,7-difluoro-1H-benzimidazol-2-yl)amino]phenyl}-N-[2-(dimethylamino)ethyl]pyrrolo[2,1-f][1,2,4]triazine-6-carboxamide;

4-amino-N-cyclopentyl-5-{4-[(5,7-difluoro-1H-benzimidazol-2-yl)amino]phenyl}pyrrolo[2,1-f][1,2,4]triazine-6-carboxamide;

4-amino-5-{4-[(5,7-difluoro-1H-benzimidazol-2-yl)amino]phenyl}-N-(2-ethoxyethyl)pyrrolo[2,1-f][1,2,4]triazine-6-carboxamide;

4-amino-5-{4-[(5,7-difluoro-1H-benzimidazol-2-yl)amino]phenyl}-N-(2-hydroxycyclohexyl)pyrrolo[2,1-f][1,2,4]triazine-6-carboxamide;

4-amino-5-{4-[(5,7-difluoro-1H-benzimidazol-2-yl)amino]phenyl}-N-(tetrahydro-2H-pyran-4-ylmethyl)pyrrolo[2,1-f][1,2,4]triazine-6-carboxamide;

4-amino-5-{4-[(5,7-difluoro-1H-benzimidazol-2-yl)amino]phenyl}-N-ethyl-N-methylpyrrolo[2,1-f][1,2,4]triazine-6-carboxamide;

4-amino-5-{4-[(5,7-difluoro-1H-benzimidazol-2-yl)amino]phenyl}-N-ethyl-N-isopropylpyrrolo[2,1-f][1,2,4]triazine-6-carboxamide;

5-{4-[(5,7-difluoro-1H-benzimidazol-2-yl)amino]phenyl}-6-{[2-(methoxymethyl)pyrrolidin-1-yl]carbonyl}pyrrolo[2,1-f][1,2,4]triazin-4-amine;

4-amino-5-{4-[(5,7-difluoro-1H-benzimidazol-2-yl)amino]phenyl}-N-isopropyl-N-methylpyrrolo[2,1-f][1,2,4]triazine-6-carboxamide;

4-amino-5-{4-[(5,7-difluoro-1H-benzimidazol-2-yl)amino]phenyl}-N-methyl-N-propylpyrrolo[2,1-f][1,2,4]triazine-6-carboxamide;

4-amino-5-{4-[(5,7-difluoro-1H-benzimidazol-2-yl)amino]phenyl}-N-[2-(dimethylamino)ethyl]-N-methylpyrrolo[2,1-f][1,2,4]triazine-6-carboxamide;

5-{4-[(5,7-difluoro-1H-benzimidazol-2-yl)amino]phenyl}-6-{[(3R)-3-(dimethylamino)pyrrolidin-1-yl]carbonyl}pyrrolo[2,1-f][1,2,4]triazin-4-amine;

5-{4-[(5,7-difluoro-1H-benzimidazol-2-yl)amino]phenyl}-6-(pyrrolidin-1-ylcarbonyl)pyrrolo[2,1-f][1,2,4]triazin-4-amine;

4-amino-5-{4-[(5,7-difluoro-1H-benzimidazol-2-yl)amino]phenyl}-N-ethyl-N-propylpyrrolo[2,1-f][1,2,4]triazine-6-carboxamide;

5-{4-[(5,7-difluoro-1H-benzimidazol-2-yl)amino]phenyl}-6-[(4-methylpiperazin-1-yl)carbonyl]pyrrolo[2,1-f][1,2,4]triazin-4-amine;

4-[(4-amino-5-{4-[(5,7-difluoro-1H-benzimidazol-2-yl)amino]phenyl}pyrrolo[2,1-f][1,2,4]triazin-6-yl)carbonyl]piperazin-2-one;

4-amino-5-{4-[(5,7-difluoro-1H-benzimidazol-2-yl)amino]phenyl}-N-methyl-N-(tetrahydro-2H-pyran-4-ylmethyl)pyrrolo[2,1-f][1,2,4]triazine-6-carboxamide;

4-amino-5-{4-[(7-fluoro-6-phenoxy-1H-benzimidazol-2-yl)amino]phenyl}pyrrolo[2,1-f][1,2,4]triazine-6-carboxylic acid;

4-amino-5-{4-[(7-fluoro-6-phenoxy-1H-benzimidazol-2-yl)amino]phenyl}-N-methylpyrrolo[2,1-f][1,2,4]triazine-6-carboxamide;

4-amino-5-{4-[(7-fluoro-6-phenoxy-1H-benzimidazol-2-yl)amino]phenyl}-N-propylpyrrolo[2,1-f][1,2,4]triazine-6-carboxamide;

4-amino-5-{4-[(7-fluoro-6-phenoxy-1H-benzimidazol-2-yl)amino]phenyl}-N-isopropylpyrrolo[2,1-f][1,2,4]triazine-6-carboxamide;

4-amino-N-cyclopropyl-5-{4-[(7-fluoro-6-phenoxy-1H-benzimidazol-2-yl)amino]phenyl}pyrrolo[2,1-f][1,2,4]triazine-6-carboxamide;

4-amino-N-ethyl-5-{4-[(7-fluoro-6-phenoxy-1H-benzimidazol-2-yl)amino]phenyl}-N-methylpyrrolo[2,1-f][1,2,4]triazine-6-carboxamide;

5-{4-[(7-fluoro-6-phenoxy-1H-benzimidazol-2-yl)amino]phenyl}-6-(piperidin-1-ylcarbonyl)pyrrolo[2,1-f][1,2,4]triazin-4-amine;

5-{4-[(7-fluoro-6-phenoxy-1H-benzimidazol-2-yl)amino]phenyl}-6-(morpholin-4-ylcarbonyl)pyrrolo[2,1-f][1,2,4]triazin-4-amine;

4-amino-N-ethyl-5-{4-[(5-pyrrolidin-1-yl-3H-imidazo[4,5-b]pyridin-2-yl)amino]phenyl}pyrrolo[2,1-f][1,2,4]triazine-6-carboxamide;

4-amino-5-{4-[(7-fluoro-6-phenoxy-1H-benzimidazol-2-yl)amino]phenyl}-N-(2-methoxyethyl)pyrrolo[2,1-f][1,2,4]triazine-6-carboxamide;

4-amino-5-{4-[(7-fluoro-6-phenoxy-1H-benzimidazol-2-yl)-amino]phenyl}-N-isobutylpyrrolo[2,1-f][1,2,4]triazine-6-carboxamide;

4-amino-N-cyclopentyl-5-{4-[(7-fluoro-6-phenoxy-1H-benzimidazol-2-yl)amino]phenyl}pyrrolo[2,1-f][1,2,4]triazine-6-carboxamide;

5-{4-[(7-fluoro-6-phenoxy-1H-benzimidazol-2-yl)amino]phenyl}-6-(pyrrolidin-1-ylcarbonyl)pyrrolo[2,1-f][1,2,4]triazin-4-amine;

4-amino-N-(cyclopropylmethyl)-5-{4-[(7-fluoro-6-phenoxy-1H-benzimidazol-2-yl)amino]phenyl}pyrrolo[2,1-f][1,2,4]triazine-6-carboxamide;

4-amino-5-(4-{[5-(4-methylphenyl)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[3-(methoxymethyl)phenyl]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-N-(tert-butyl)-5-{4-[(6-chloro-3H-imidazo[4,5-b]pyridin-2-yl)amino]-3-fluorophenyl}pyrrolo[2,1-f][1,2,4]triazine-6-carboxamide;

4-amino-N-(tert-butyl)-5-{4-[(2,2-difluoro-5H-[1,3]dioxolo[4,5-f]benzimidazol-6-yl)amino]-3-fluorophenyl}pyrrolo[2,1-f][1,2,4]triazine-6-carboxamide;

4-amino-5-(4-{[5-(trifluoromethyl)-3H-imidazo[4,5-b]pyridin-2-yl]amino}phenyl)pyrrolo[2,1-f][1,2,4]triazine-6-carboxylic acid;

4-amino-N-(2,2,2-trifluoroethyl)-5-(4-{[5-(trifluoromethyl)-3H-imidazo[4,5-b]pyridin-2-yl]amino}phenyl)pyrrolo[2,1-f][1,2,4]triazine-6-carboxamide;

ethyl-4-amino-5-[4-(1H-benzimidazol-2-ylamino)phenyl]pyrrolo[2,1-f][1,2,4]triazine-6-carboxylate;

ethyl-4-amino-5-{4-[(5-methoxy-1H-benzimidazol-2-yl)amino]phenyl}pyrrolo[2,1-f][1,2,4]triazine-6-carboxylate;

or a pharmaceutically acceptable salt thereof.

Depending on their structure, the compounds according to the invention can exist in stereoisomeric forms (enantiomers or diastereomers). The invention therefore relates to the enantiomers or diastereomers and to their respective mixtures. Such mixtures of enantiomers or diastereomers can be separated into stereoisomerically unitary constituents in a known manner.

The invention also relates to tautomers of the depicted compounds, depending on the structure of the respective compound.

DEFINITIONS

Unless otherwise stated, the following definitions apply for the technical expressions used throughout this specification and claims:

"Salts" for the purposes of the invention are preferably pharmaceutically acceptable salts of the compounds according to the invention. For example, see S. M. Berge, et al. "Pharmaceutical Salts," J. Pharm. Sci. 1977, 66, 1-19.

"Pharmaceutically acceptable salts" include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

"Pharmaceutically acceptable salts" also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, diethylamine, ethyldi-iso-propylamine, monoethanolamine, diethanolamine, triethanolamine, dicyclohexylamine, dimethylaminoethanol, procaine, dibenzylamine, N-methylmorpholine, dihydro-abietylamine, arginine, lysine, ethylenediamine and methylpiperidine.

The term 'alkyl' refers to a straight or branched hydrocarbon chain radical consisting solely of carbon and hydrogen atoms, containing solely of carbon and hydrogen atoms, containing no unsaturation, having from one to eight carbon atoms, and which is attached to the rest of the molecule by a single bond, such as illustratively, methyl, ethyl, n-propyl 1-methylethyl (isopropyl), n-butyl, n-pentyl, and 1,1-dimethylethyl (t-butyl).

The term "alkoxy" denotes an alkyl group as defined herein attached via oxygen linkage to the rest of the molecule. Representative examples of those groups are —$OCH_3$, —$OC_2H_5$.

The term "alkoxyalkyl" denotes an alkoxy group as defined herein attached via oxygen linkage to an alkyl group which is then attached to the main structure at any carbon from alkyl group that results in the creation of a stable structure the rest of the molecule. Representative examples of those groups are —$CH_2OCH_3$, —$CH_2OC_2H_5$.

The term "alkylcarbonyl" denotes an alkyl group as defined herein attached via carbonyl linkage to the rest of the molecule. Representative examples of those groups are —$C(O)CH_3$, —$C(O)C_2H_5$.

The term "alkoxycarbonyl" denotes an alkoxy group as defined herein attached via carbonyl linkage to the rest of the molecule. Representative examples of those groups are —$C(O)$—$OCH_3$, —$C(O)$—$OC_2H_5$.

The term "alkylcarbonyloxy" denotes an alkylcarbonyl group as defined herein attached via oxygen linkage to the rest of the molecule. Representative examples of those groups are $O$—$C(O)CH_3$, —$O$—$C(O)C_2H_5$.

The term "alkylamino" denotes an alkyl group as defined herein attached via amino linkage to the rest of the molecule. Representative examples of those groups are —$NHCH_3$, —$N(CH_3)_2$.

The term "cycloalkylamino" denotes a cycloalkyl group as defined herein attached via amino linkage to the rest of the molecule. Representative examples of those groups are —NH-cyclopropyl, —NH-cyclopentyl.

The term "cycloalkylalkylamino" denotes a cycloalkylalkyl group as defined herein attached via amino linkage to the rest of the molecule. Representative examples of those groups are —$NHCH_2$cyclopropyl, —$NHCH_2$cyclopentyl.

The term "alkoxyalkylamino" denotes an alkoxyalkyl group as defined herein attached via amino linkage to the rest of the molecule. Representative examples of those groups are methoxylmethylamino, methoxylethylamino, ethoxyethylamino.

The term "alkylaminocarbonyl" denotes an alkylamino group as defined herein attached via carbonyl linkage to the rest of the molecule. Representative examples of those groups are —$C(O)$—$NHCH_3$, —$C(O)$—$NHCH_2CH_3$, —$C(O)$—$N(CH_3)_2$.

The term "alkylaminosulfonyl" denotes an alkylamino group as defined herein attached via sulfonyl linkage to the rest of the molecule. Representative examples of those groups are —$S(O)_2$—$NHCH_3$, $S(O)_2$—$N(CH_3)_2$.

The term "alkylaminoalkyl" denotes an alkylamino group as defined herein attached via alkyl linkage to the rest of the molecule. Representative examples of those groups are —$CH_2$—$NHCH_3$, —$CH_2$—$N(CH_3)_2$.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g sprio (4,4) non-2-yl.

The term "cycloalkylalkyl" refers to cyclic ring-containing radicals containing in the range of about 3 up to 8 carbon atoms directly attached to alkyl group which are then attached to the main structure at any carbon from alkyl group that results in the creation of a stable structure such as cyclopropylmethyl, cyclobuyylethyl, cyclopentylethyl.

The term "cycloalkenyl" refers to cyclic ring-containing radicals containing in the range of about 3 up to 8 carbon atoms with at least one carbon-carbon double bond such as cyclopropenyl, cyclobutenyl, cyclopentenyl.

The term "aryl" refers to aromatic radicals having in the range of 6 up to 14 carbon atoms such as phenyl, naphthyl, tetrahydronapthyl, indanyl, biphenyl.

The term "arylalkyl" refers to an aryl group as defined herein directly bonded to an alkyl group as defined herein. e.g., —$CH_2C_6H_5$, —$C_2H_4C_6H_5$.

The term "phenyloxy" refers to a phenyl group attached via oxygen linkage to the rest of the molecule.

The term "thiophenyl" refers to a phenyl group attached via sulfur linkage to the rest of the molecule.

The term "halophenyloxy" refers to a phenyloxy group as defined herein further substituted with one or more halogen atoms.

The term "halothiophenyl" refers to a thiophenyl group as defined herein further substituted with one or more halogen atoms.

The term "methylphenyloxy" refers to a phenyloxy group as defined herein further substituted with one or more methyl groups.

The term "alkoxyphenyl" refers to a phenyl group as defined herein further substituted with one or more alkoxy groups.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl cinnolinyl dioxolanyl, indolizinyl, naphthyridinyl, perhydroazepinyl, phenazinyl, phenothiazinyl, phenoxazinyl, phthalazil, pyridyl, pteridinyl, purinyl, quinazolinyl, quinoxalinyl, quinolinyl, isoquinolinyl, tetrazoyl, imidazolyl tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl pyridazinyl, oxazolyl oxazolinyl oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl.

The term "heteroaryl" refers to heterocyclic ring radical as defined herein which are aromatic. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined herein directly bonded to alkyl group. The heteroarylalkyl radical may be attached to the main structure at any carbon atom from alkyl group that results in the creation of a stable structure.

The term "heterocyclyl" refers to a heterocylic ring radical as defined herein. The heterocylyl ring radical may be attached to the main structure at any heteroatom or carbon atom that results in the creation of a stable structure.

The term "heterocyclylalkyl" refers to a heterocylic ring radical as defined herein directly bonded to alkyl group. The heterocyclylalkyl radical may be attached to the main structure at carbon atom in the alkyl group that results in the creation of a stable structure.

The term "carboxyl" refers to an oxygen atom bound to a carbon atom of the molecule by a double bond.

The term "halogen" refers to radicals of fluorine, chlorine, bromine and iodine.

A * symbol next to a bond denotes the point of attachment in the molecule.

Throughout this document, for the sake of simplicity, the use of singular language is given preference over plural language, but is generally meant to include the plural language if not otherwise stated. E.g., the expression "A method of treating a disease in a patient, comprising administering to a patient an effective amount of a compound of formula (I)" is meant to include the simultaneous treatment of more than one disease as well as the administration of more than one compound of formula (I).

Preparatory Methods of the Invention

In another embodiment, the present invention provides a process for preparing a compound of formula (I), comprising [A] reacting a compound of formula (II)

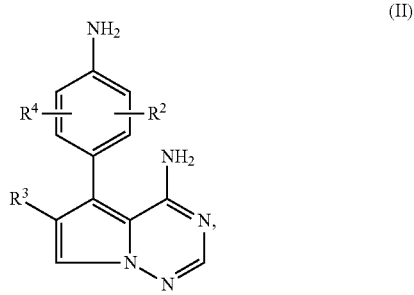

(II)

wherein $R^2$, $R^3$ and $R^4$ have the meaning indicated above, with a diamino compound of formula (III)

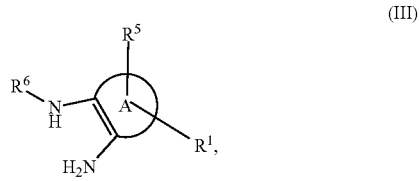

(III)

wherein $R^1$, $R^5$, and $R^6$ have the meaning indicated above in the presence of a one carbon source such as thiocarbonyldiamidazole, followed by cyclization with a coupling agent, such as N,N'-diisopropylcarbodiimide; or

[B] coupling a compound of formula (II), wherein $R^2$, $R^3$ and $R^4$ have the meaning indicated above, with a 2-chlorobenzimidazole of formula (IV),

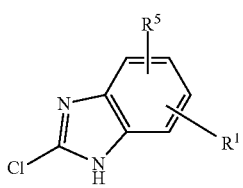

wherein $R^1$ and $R^5$ have the meaning indicated above.

In a preferred embodiment of method [A], the compound of formula (III) has the formula (IIIa)

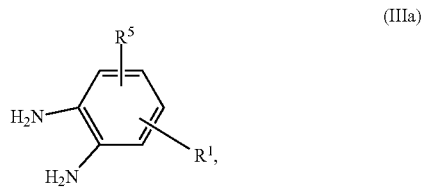

wherein $R^1$ and $R^5$ have the meaning indicated above.

It is also to be understood that starting materials are commercially available or readily prepared by standard methods well known in the art. Such methods include, but are not limited to the transformations listed herein.

If not mentioned otherwise, the reactions are usually carried out in inert organic solvents that do not change under the reaction conditions. These include ethers, such as diethyl ether, 1,4-dioxane or tetrahydrofuran, halogenated hydrocarbons, such as dichloromethane, trichloromethane, carbon tetrachloride, 1,2-di-chloroethane, trichloroethane or tetrachloroethane, hydrocarbons, such as benzene, toluene, xylene, hexane, cyclohexane or mineral oil fractions, alcohols, such as methanol, ethanol or iso-propanol, nitromethane, dimethylformamide or acetonitrile. It is also possible to use mixtures of the solvents.

The reactions are generally carried out in a temperature range of from 0° C. to 150° C., preferably from 0° C. to 70° C. The reactions can be carried out under atmospheric, elevated or under reduced pressure (for example from 0.5 to 5 bar). In general, they are carried out under atmospheric pressure of air or inert gas, typically nitrogen.

Methods for preparing pyrrolotriazines are also disclosed in published U.S. application Ser. No. 10/289,010 (Publication No. US 2003-0186982 A1), U.S. Pat. No. 6,670,357 (U.S. application Ser. No. 10/036,293), all of which are hereby incorporated by reference in their entirety, as well as WO 2003/042172, WO 2004/009542, WO2004/009601, WO 2004/009784 and WO 2004/013145.

The compounds of the invention may be prepared by use of known chemical reactions and procedures. Nevertheless, the following general preparative methods are presented to aid the reader in synthesizing said compounds, with more detailed particular examples being presented below in the experimental section describing the examples. The preparation of a compound of the present invention can be illustrated by means of the following synthetic scheme.

General Methods of Preparation of Invention Compounds

Compounds of the present invention of Formula (I) can be conveniently prepared from the corresponding amino compounds of Formula (II) by straightforward means as described in the Reaction Schemes below or by means well known to those skilled in the art. In these Reaction Schemes, unless otherwise specifically defined, the meanings of $R^1$-$R^6$ are identical to those described above.

Reaction Scheme 1 illustrates the general method of preparing Formula (I) compounds from the corresponding amino compounds of Formula (II) by standard methods of benzimidazole formation. In this scheme, a Formula (II) compound is allowed to react with a one-carbon source such as 1,1'-thicarbonyldiimidazole in a polar aprotic solvent such as DMF to give the compound of Formula (V). This compound, without isolation, may then be treated a diamine of Formula (III) to afford the compound of Formula (VI), which in turn is treated with a coupling reagent such as N,N'-diisopropylcarbodiimide to afford the desired compound of Formula (I). Alternatively, the compound of Formula (I) can be obtained by reacting, at an elevated temperature, a Formula (II) compound with a compound of Formula (IV) in the presence of HCl and a polar protic solvent such as n-butanol. It should be recognized that compounds of Formula (III) and Formula (IV) may be commercially available or synthesized from readily available starting materials using synthetic routes well known in the art. Alternatively, compounds of Formula (III) may be prepared as described below in Reaction Scheme 6.

Reaction Scheme 1

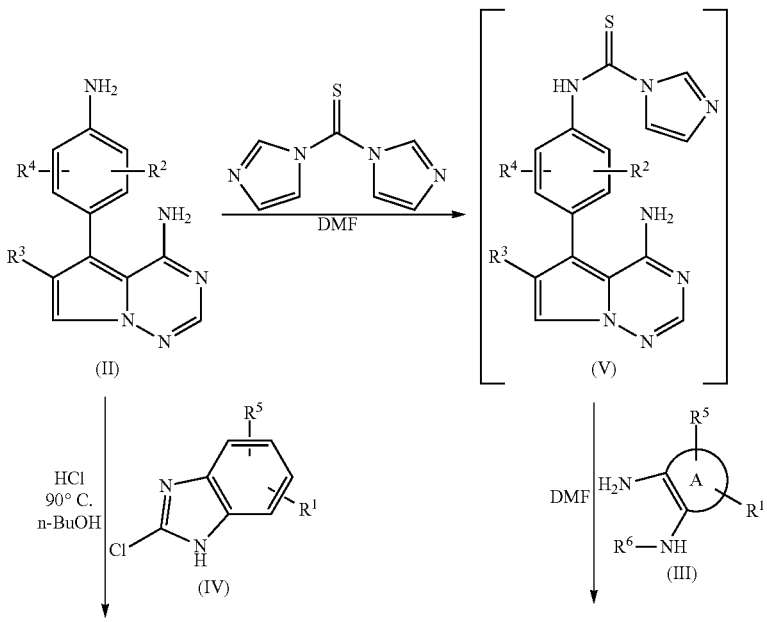

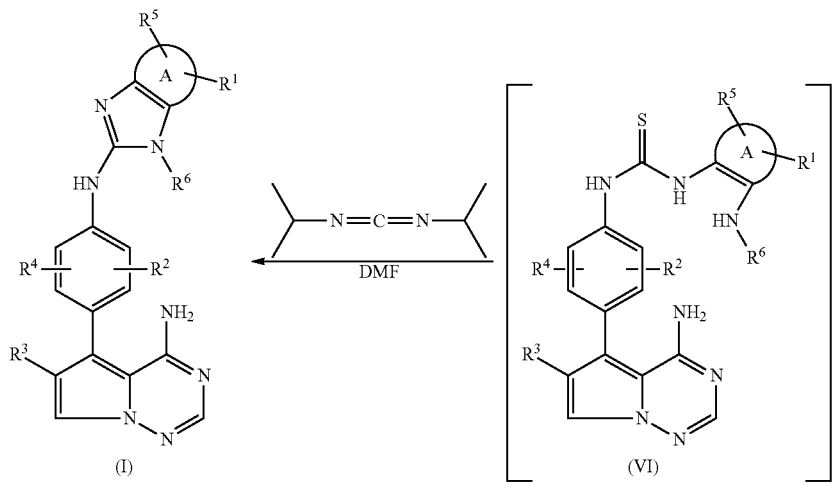

The compound of Formula (II) may be obtained using the synthetic routes described in Reaction Scheme 2. In one variation, the nitro group of Compound (VII) can be reduced (for example, with iron in the presence of ammonium chloride and carefully controlled heating) to afford an aniline of Formula (VIII). Compound (VIII) can then be reacted with an aminating reagent (IX) in the presence of a base such as sodium hydride to afford a hydrazine of Formula (X). Hydrazine (X) can then be reacted with either formamidine or formamidine acetate and heated to induce cyclization to a pyrrolotriazine of Formula (II). In a second variation, the pyrrole of Formula (VII) is reacted with aminating reagent (IX) to afford the N-amino nitrile of Formula (XI). Reaction of (XI) with a formamide equivalent gives the pyrrolotriazine intermediate of Formula (XII). Selective reduction of the nitro substituent of the phenyl ring is accomplished in the final step using a catalyst such as Raney-Nickel in THF, providing Intermediate (II).

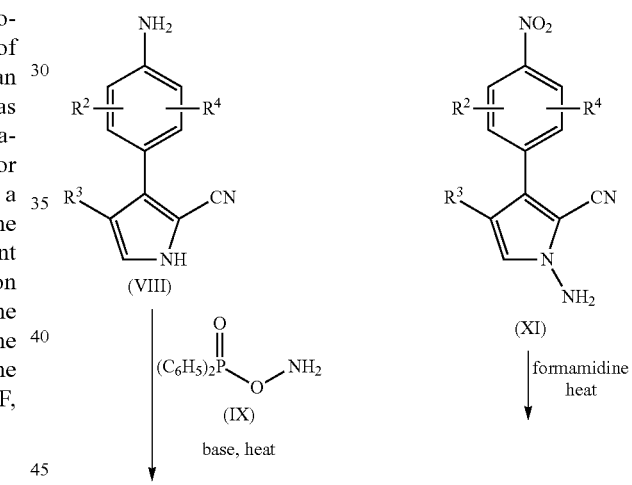

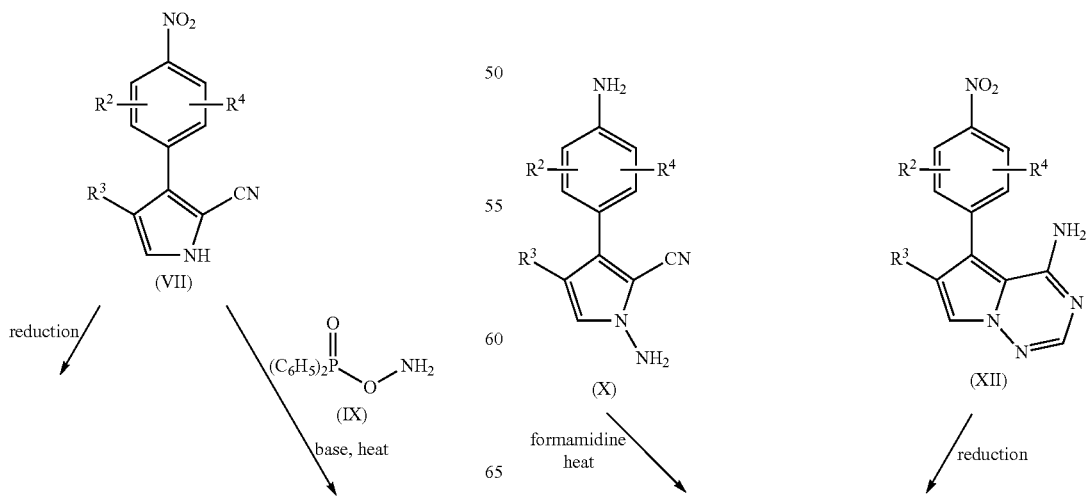

Reaction Scheme 2

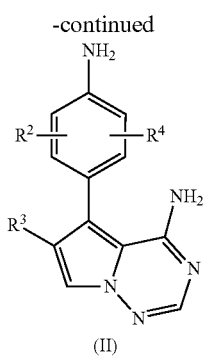

Additionally, compounds of Formula (Ia), (IIa), and (VIIa), where $R^3$ is an ester group, may be easily converted to compounds of Formula (Ib), (IIb), and (VIIb) respectively, where $R^3$ is an amide moiety, as illustrated in Reaction Scheme 3. The ester is first converted to its corresponding carboxylic acid through base hydrolysis and then amide bond formation under standard peptide coupling techniques gives the desired products. Alternatively, the carboxylic acid may be converted to its corresponding acid chloride, which may then be reacted with an amine to again give the desired amides.

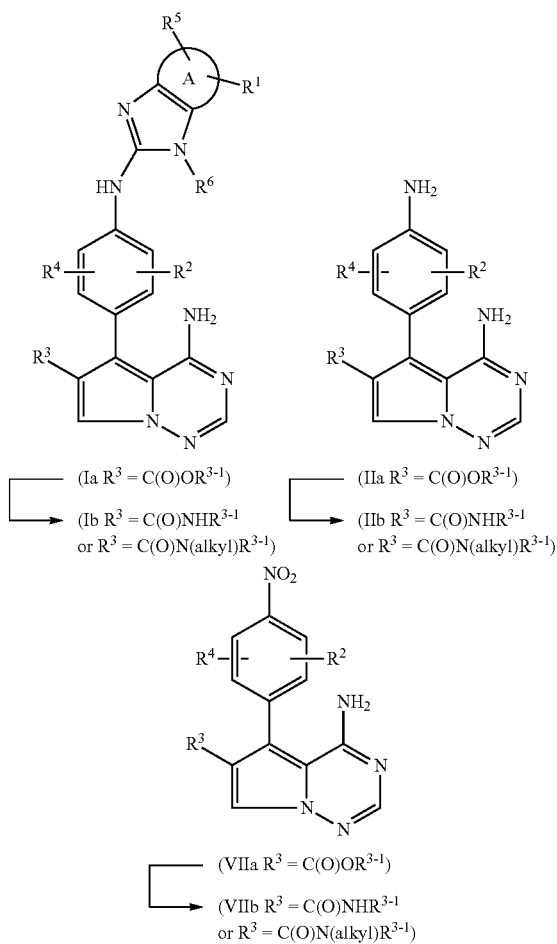

Steps: 1) ester hydrolysis; 2) peptide coupling with $NH_2R^{3-1}$ or $HN(alkyl)R^{3-1}$ or 1) ester hydrolysis; 2) acid chloride formation; 3) coupling with $NH_2R^{3-1}$ or $HN(alkyl)R^{3-1}$ The preparation of intermediate (VII), shown above as starting material for Reaction Scheme 2, can be carried out as illustrated below in Reaction Scheme 4 ($R^3=CO_2CH_2CH_3$). A 4-nitrocinnamate of Formula (XIII) is allowed to react with the isocyanide reagent of Formula (XIV) in the presence of a strong base such as lithium hexamethyldisilazide (LHMDS) in an aprotic solvent such as THF, to give the substituted pyrrole of Formula (XV). Formylation of (XV) under Vilsmeier conditions (e.g., DMF, phosphorous oxychloride) gives 2-formylpyrrole of Formula (XVI). The aldehyde group in Compound (XVI) is reacted with hydroxylamine hydrochloride to form an intermediate oxime, which is then dehydrated in situ, using a reagent such as acetic anhydride to afford the desired nitrile of Formula (VIIa).

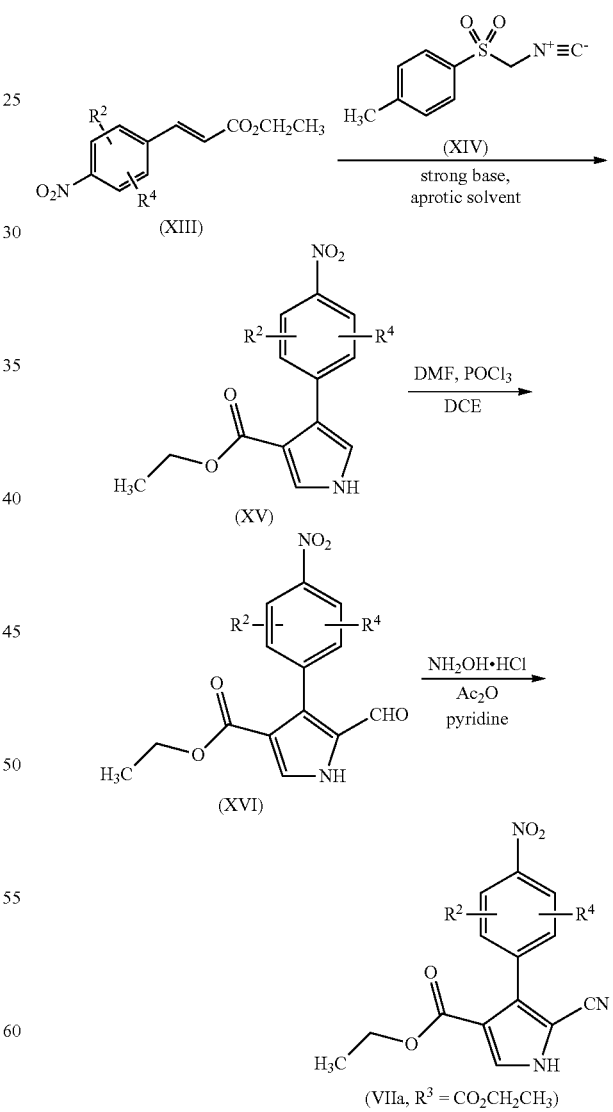

An alternate synthesis of Compound (VIIa) is shown in Reaction Scheme 4. The route starts with an appropriately substituted 4-nitrobenzoic acid of Formula (XVII). The acid is converted to an acid chloride, typically with thionyl chloride or oxalyl chloride, and then this is coupled with the magnesium salt of ethylpotassium malonate (XVIII) to afford a β-ketoester of Formula (XIX). This compound is condensed with N,N-dimethylformamide dimethyl acetal to afford an α,β-unsaturated ketone of Formula (XX) that can then be reacted with 2-aminomalonamide (XXI) in the presence of acid (for example acetic acid and trifluoroacetic acid) and heating to form, after cyclization, a pyrrole of Formula (XXII). The primary amide group found in the pyrrole of Formula (XXII) can be dehydrated (for example, in the presence of phosphorous oxychloride) to afford a 5-cyanopyrrole of Formula (VIIa).

methods described in the literature. Alternatively, some may also be made using the methods described in Reaction Scheme 6. In one variation a 3-halo-5-nitroaniline of Formula (XXIII), where X is fluorine or chlorine, is reacted with a nucleophile, $R^1$—H, where the nucleophile may be an amine, alcohol or thiol, in the presence of a weak base such as potassium carbonate to afford a 5-nitro aniline of Formula (XXIV). The nitro group may then be reduced (for example with tin chloride or under a hydrogen atmosphere in the presence of Raney nickel catalysis) to produce a diamine of Formula (IIIb). Similarly, a 1-amino-2-nitro-6-halopyridine of Formula (XXV) may be reacted first with a nucleophile, $R^1$—H, to afford Intermediate (XXVI) and then reduced (for example with iron and acetic acid) to produce compounds of Formula (IIIc).

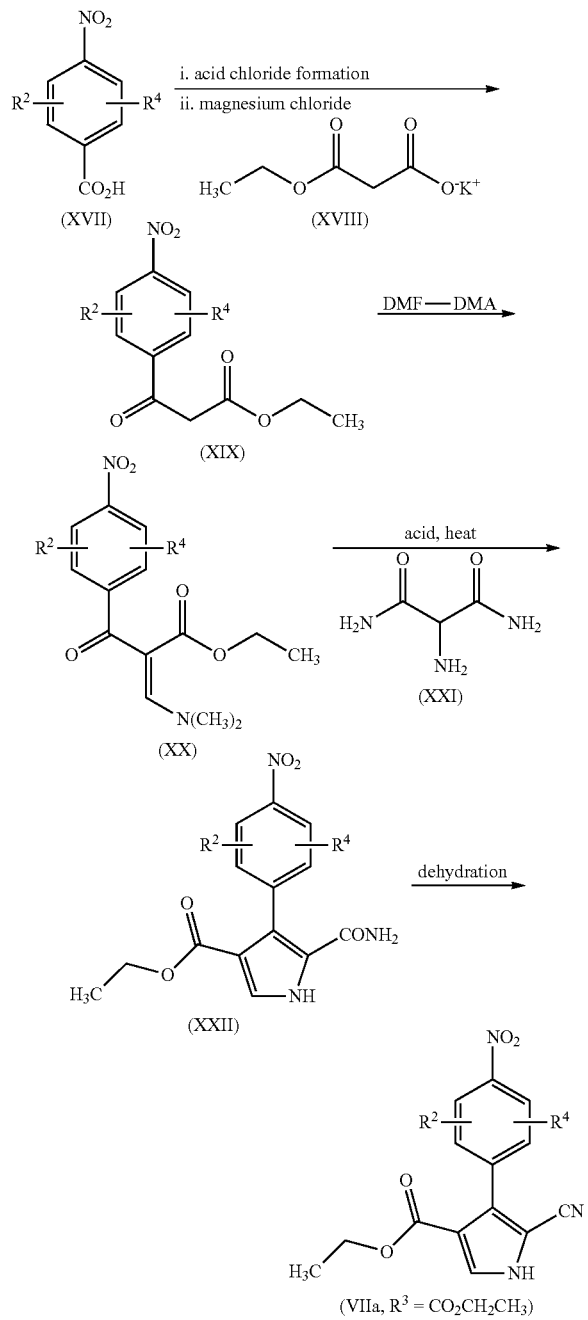

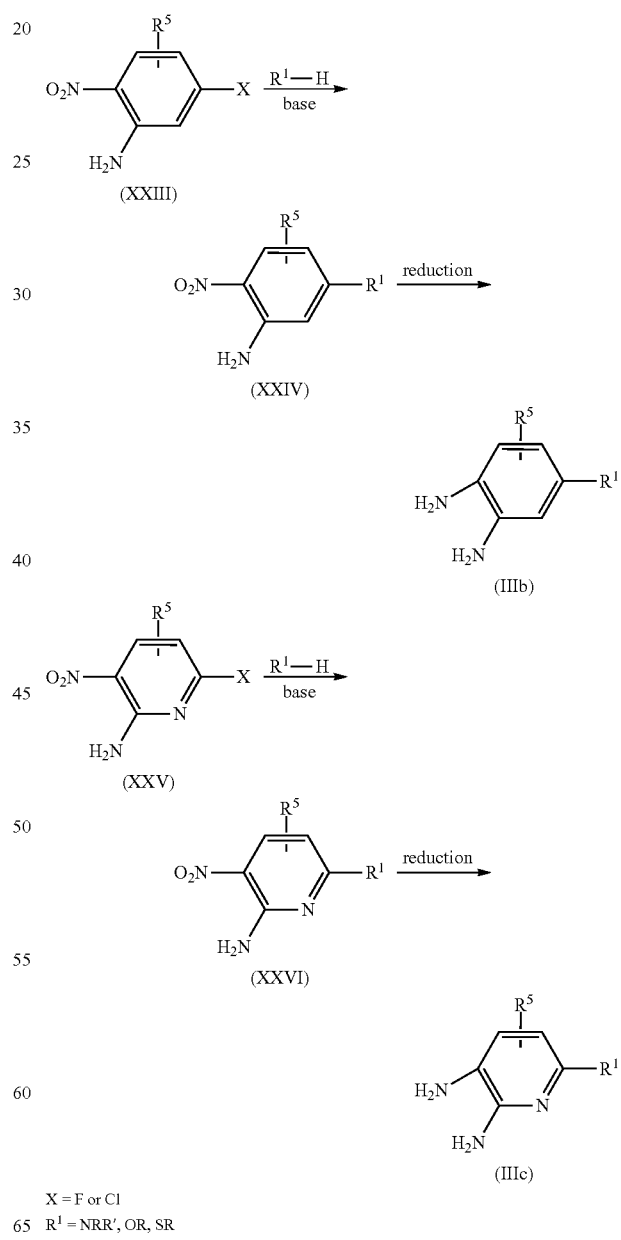

Diamines of Formula (III) shown above in Reaction Scheme 1 may be purchased or conveniently made using Pharmaceutical Compositions of the Compounds of the Invention This invention also relates to pharmaceutical compositions containing one or more compounds of the present invention. These compositions can be utilized to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, or vaginally.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:
50 mg/mL of the desired, water-insoluble compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Disorders

The present invention relates to a method for using the compounds of the present invention and compositions thereof, to treat mammalian disorders, in particular hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations. The desired mode of treatment and number of doses of a compound of the present invention or a pharmaceutically acceptable salt or ester or composition thereof can be ascertained by those skilled in the art using conventional treatment tests.

EXAMPLES

Abbreviations and Acronyms

A comprehensive list of the abbreviations used by organic chemists of ordinary skill in the art appears in The ACS Style Guide (third edition) or the Guidelines for Authors for the *Journal of Organic Chemistry*. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:
Ac acetyl
atm atmosphere
br s broad singlet
BuOH butanol
C Celsius
Celite® diatomaceous earth filter agent ®Celite Corp.
$CH_2Cl_2$ dichloromethane
d doublet
dd doublet of doublets
ddd doublet of doublet of doublets
DCE 1,1-dichlroethane
DMF N,N-dimethylformamide
DMF-DMA N,N-dimethylformamide dimethyl acetal
DMSO dimethylsulfoxide
ES-MS electrospray mass spectroscopy
EtOAc ethyl acetate
g gram
h hour, hours
$^1$H NMR proton nuclear magnetic resonance
HPLC high performance liquid chromatography
J coupling constant (NMR spectroscopy)
L liter
M mol $L^{-1}$ (molar)
m multiplet
MHz megahertz
min minute, minutes
mL milliliter
μM micromolar
mol mole
MS mass spectrum, mass spectrometry
m/z mass-to-charge ratio
N equivalents $L^{-1}$ (normal)
NMR Nuclear Magnetic Resonance
pH negative logarithm of hydrogen ion concentration
$^{31}$P NMR phosphorous nuclear magnetic resonance
$POCl_3$ phosphorous oxychloride
q quartet
RT retention time (HPLC)
rt room temperature
s singlet
t triplet
THF tetrahydrofuran The percentage yields reported in the following examples are based on the starting component that was used in the lowest molar amount. Air and moisture sensitive liquids and solutions were transferred via syringe or cannula, and introduced into reaction vessels through rubber septa. Commercial grade reagents and solvents were used without further purification. The term "concentrated under reduced pressure" refers to use of a Buchi rotary evaporator at approximately 15 mm of Hg. All temperatures are reported uncorrected in degrees Celsius (° C.). Thin layer chromatography (TLC) was performed on pre-coated glass-backed silica gel 60 A F-254 250 μm plates.

The structures of compounds of this invention were confirmed using one or more of the following procedures.
NMR NMR spectra were acquired for each compound and were consistent with the structures shown.

Routine one-dimensional NMR spectroscopy was performed on either 300 or 400 MHz Varian® Mercury-plus spectrometers. The samples were dissolved in deuterated solvents. Chemical shifts were recorded on the ppm scale and were referenced to the appropriate solvent signals, such as 2.49 ppm for DMSO-d6, 1.93 ppm for CD3CN, 3.30 ppm for CD3OD, 5.32 ppm for CD2Cl2 and 7.26 ppm for CDCl3 for 1H spectra.
GC/MS Electron impact mass spectra (EI-MS) were obtained with a Hewlett Packard 5973 mass spectrometer equipped Hewlett Packard 6890 Gas Chromatograph with a J & W HP-5 column (0.25 uM coating; 30 m×0.32 mm). The ion source was maintained at 250° C. and spectra were scanned from 50-550 amu at 0.34 sec per scan.
LC/MS Unless otherwise noted, all retention times are obtained from the LC/MS and correspond to the molecular ion. High pressure liquid chromatography-electrospray mass spectra (LC/MS) were obtained using one of the following:
Method A (LCQ)

Hewlett-Packard 1100 HPLC equipped with a quaternary pump, a variable wavelength detector set at 254 nm, a Waters Sunfire C18 column (2.1×30 mm, 3.5 μm), a Gilson autosampler and a Finnigan LCQ ion trap mass spectrometer with electrospray ionization. Spectra were scanned from 120-1200 amu using a variable ion time according to the number of ions in the source. The eluents were A: 2% acetonitrile in water with 0.02% TFA, and B: 2% water in acetonirile with 0.018% TFA. Gradient elution from 10% B to 95% B over 3.5 minutes at a flow rate of 1.0 mL/min was used with an initial hold of 0.5 minutes and a final hold at 95% B of 0.5 minutes. Total run time was 6.5 minutes.
Method B (LCQ5)

Agilent 1100 HPLC system. The Agilent 1100 HPLC system was equipped with an Agilent 1100 autosampler, quaternary pump, a variable wavelength detector set at 254 nm. The HPLC column used was a Waters Sunfire C-18 column (2.1× 30 mm, 3.5 μm). The HPLC eluent was directly coupled without splitting to a Finnigan LCQ DECA ion trap mass spectrometer with electrospray ionization. Spectra were scanned from 140-1200 amu using a variable ion time according to the number of ions in the source using positive ion mode. The eluents were A: 2% acetonitrile in water with 0.02% TFA, and B: 2% water in acetonitrile with 0.02% TFA. Gradient elution from 10% B to 90% B over 3.0 minutes at a flow rate of 1.0 mL/min was used with an initial hold of 1.0 minutes and a final hold at 95% B of 1.0 minutes. Total run time was 7.0 minutes.

Method C (LTQ)

Agilent 1100 HPLC system. The Agilent 1100 HPLC system was equipped with an Agilent 1100 autosampler, quaternary pump, and a diode array. The HPLC column used was a Waters Sunfire C18 column (2.1×30 mm, 3.5 µm). The HPLC eluent was directly coupled with a 1:4 split to a Finnigan LTQ ion trap mass spectrometer with electrospray ionization. Spectra were scanned from 50-800 amu using a variable ion time according to the number of ions in the source using positive or negative ion mode. The eluents were A: water with 0.1 formic acid, and B: acetonitrile with 0.1% formic acid. Gradient elution from 10% B to 90% B over 3.0 minutes at a flowrate of 1.0 mL/min was used with an initial hold of 2.0 minutes and a final hold at 95% B of 1.0 minutes. Total run time was 8.0 minutes.

Method D (Sunfire4_6×50_100a_5a_5 min_4_0 ml)

HPLC—electrospray mass spectra (HPLC ES-MS) were obtained using a Gilson HPLC system equipped with two Gilson 306 pumps, a Gilson 215 Autosampler, a Gilson diode array detector, a Waters Sunfire column (4.6×50 mm, 5 µm), and a Micromass ZMD single quadrupole mass spectrometer with z-spray electrospray ionization. Spectra were scanned from 120-1000 amu over 2 seconds. The eluents were A: water with 0.02% TFA and B: Acetonitrile with 0.02% TFA. Gradient elution at a flow rate of 4.0 mL/min was used with the following protocol: 100% A for 1.0 minutes, 100% A ramped to 95% B over 3.0 minutes, held at 95% B for 0.8 minutes, and then 95% B ramped to 100% A over 0.1 minute. Total run time was 5.0 minutes.

Preparative HPLC:

Preparative HPLC was carried out in reversed phase mode, typically using a Gilson HPLC system equipped with two Gilson 322 pumps, a Gilson 215 Autosampler, a Gilson diode array detector, and a C-18 column (e.g. YMC Pro 20×150 mm, 120 A). Gradient elution was used with solvent A as water with 0.1% TFA, and solvent B as acetonitrile with 0.1% TFA. Following injection onto the column as a solution, the compound was typically eluted with a mixed solvent gradient, such as 10-90% Solvent B in Solvent A over 15 minutes with flow rate of 25 mL/min. The fraction(s) containing the desired product were collected by UV monitoring at 254 or 220 nm.

Preparative MPLC:

Preparative medium pressure liquid chromatography (MPLC) was carried out by standard silica gel "flash chromatography" techniques (e.g., Still, W. C. et al. *J. Org. Chem.* 1978, 43, 2923-5), or by using silica gel cartridges and devices such as the Biotage Flash systems. A variety of eluting solvents were used, as described in the experimental protocols.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

Synthetic transformations that may be employed in the synthesis of compounds of this invention and in the synthesis of intermediates involved in the synthesis of compounds of this invention are known by or accessible to one skilled in the art. Collections of synthetic transformations may be found in compilations, such as:

J. March. *Advanced Organic Chemistry*, 4th ed.; John Wiley: New York (1992)

R. C. Larock. *Comprehensive Organic Transformations*, 2nd ed.; Wiley-VCH: New York (1999)

F. A. Carey; R. J. Sundberg. *Advanced Organic Chemistry*, 2nd ed.; Plenum Press: New York (1984)

T. W. Greene; P. G. M. Wuts. *Protective Groups in Organic Synthesis*, 3rd ed.; John Wiley: New York (1999)

L. S. Hegedus. *Transition Metals in the Synthesis of Complex Organic Molecules*, 2nd ed.; University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley. New York; *Reagents for Organic Synthesis*: John Wiley: New York; *The Total Synthesis of Natural Products*; John Wiley: New York; *The Organic Chemistry of Drug Synthesis*; John Wiley: New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts*, which may be searched using either CAS OnLine or SciFinder, *Handbuch der Organischen Chemie* (Beilstein), which may be searched using SpotFire, and REACCS.

Intermediates

Intermediate A

Preparation of ethyl 4-amino-5-(4-nitrophenyl)pyrrolo[2,1-f][1,2,4]triazine-6-carboxylate

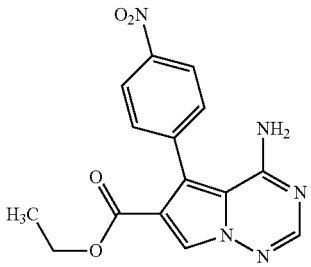

Step 1: Preparation of ethyl 4-(4-nitrophenyl)-1H-pyrrole-3-carboxylate

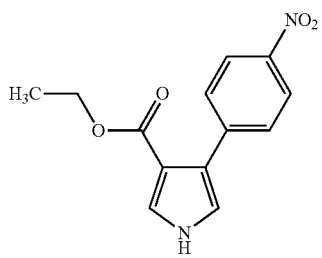

To a cooled (−77° C.) solution of 1M lithium hexamethyldisilazide in THF (102.4 mL, 102.4 mmol) was added 1-[(isocyanomethyl)sulfonyl]-4-methylbenzene (20.0 g, 102.4 mmol) as a solution in THF (100 mL) dropwise (30 min). The solution was allowed to stir for 15 min, and then ethyl (2E)-3-(4-nitrophenyl)acrylate (22.66 g, 102.4 mmol) was added dropwise (1 h) as a solution in THF (250 mL). The reaction was allowed to warm to rt over 17 h and the aqueous saturated sodium bicarbonate solution (200 mL) was added. The product was extracted with ethyl acetate (3×300 mL), and then the combined organic extracts were washed with water (100 mL), dried over magnesium sulfate, and concentrated under reduced pressure. The residue was purified by silica gel chromatography using 0-5% ethylacetate/dichlromethane to afford the desired product (16.65 g, 62%). $^1$H-NMR (300 MHz, DMSO-$d_6$) δ 11.78 (br s, 1H), 8.15-8.19 (m, 2H), 7.73-7.76 (m, 2H), 7.55-7.79 (m, 1H), 7.19-7.24 (m, 1H), 4.16 (q, J=7.1 Hz, 2H), 1.21 (t, J=7.1 Hz, 3H); HPLC (Method A) 2.90 min; TLC $R_f$=0.47 (95:5 v/v CH$_2$Cl$_2$-EtOAc).

Step 2: Preparation of ethyl 5-formyl-4-(nitrophenyl)-1H-pyrrole-3-carboxylate

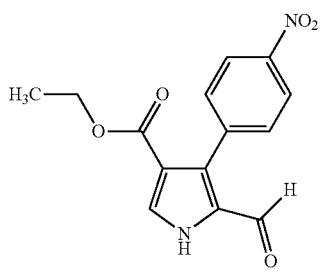

Phosphorous oxychloride (18.12 mL, 194.4 mmol) was slowly to a cooled (0° C.) solution of DMF (14.96 mL, 194.4 mmol) in dichlorethane (100 mL). The mixture was allowed to warm to it while vigorously stirring over 30 min. The slurry was again cooled (0° C.) and ethyl 4-(4-nitrophenyl)-1H-pyrrole-3-carboxylate (46.00 g, 176.8 mmol) was added as a suspension in dichloroethane (500 mL). After stirring for 1 h the reaction was warmed to it and stirred for an additional 17 h. Sodium acetate (79.75 g, 972.2 mmol) in water (600 mL) was added and the solution was heated (80° C.) for 1 h. Upon cooling to it the layers were separated and the aqueous layer was back extracted with dichlormethane (2×150 mL). The combined organic layers were dried over magnesium sulfate and concentrated to dryness. The crude material was heated to reflux in toluene (2 L) and to the hot solution was added hexanes (200 mL). The solution was allowed to slowly cool, and over the following 2 days crystals formed. The crystals were collected, washed with diethyl ether (500 mL), and dried under vacuum to afford the desired product (25.53 g, 50%). $^1$H-NMR (300 MHz, DMSO-$d_6$) δ 12.94 (br s, 1H), 9.29 (d, J=0.8 Hz, 1H), 8.25 to 8.22 (m, 2H), 7.81 (d, J=2.7 Hz, 1H), 7.74 to 7.71 (m, 2H), 4.12 to 4.06 (q, J=7.1 Hz, 2H), 1.15 to 1.11 (t, J=7.0 Hz, 3H); HPLC RT 2.75 min (Method A); TLC $R_f$=0.16 (95:5 v/v CH$_2$Cl$_2$-EtOAc).

Step 3: Preparation of ethyl 5-cyano-4-(nitrophenyl)-1H-pyrrole-3-carboxylate

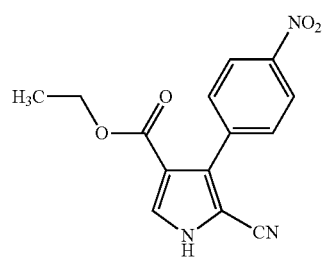

To a solution of ethyl 5-formyl-4-(nitrophenyl)-1H-pyrrole-3-carboxylate (24.55 g, 85.17 mmol) in pyridine (400 mL) was added hydroxylamine hydrochloride (6.51 g, 93.7 mmol). The solution was stirred at rt for 2 h, and then acetic anhydride (17.68 mL, 187.4 mmol) was added. The solution was heated (80° C.) for 17 h and then cooled to rt. The reaction mixture was partially concentrated in vacuo and then diluted with ethyl acetate (300 mL) and water (300 mL). The layers were separated and the aqueous layer was back extracted with ethyl acetate (2×100 mL). The combined organic layers were dried over sodium sulfate and concentrated to dryness. The crude material was then triturated with dichloromethane-diethyl ether (1:1 v/v, 300 mL). The solid was collected, washed with diethyl ether (150 mL), and dried under vacuum to afford the desired product (18.94 g, 78%). $^1$H-NMR (300 MHz, DMSO-$d_6$) δ 13.24 (br s, 1H), 8.25-8.32 (m, 2H), 7.92 (s, 1H), 7.69-7.76 (m, 2H), 4.13 (q, J=7.2 Hz, 2H), 1.16 (t, J=7.0 Hz, 3H); HPLC RT (Method A) 2.97 min; TLC $R_f$=0.20 (95:5 v/v CH$_2$Cl$_2$-EtOAc).

Step 4: Preparation of (aminooxy)(diphenyl)phosphine oxide

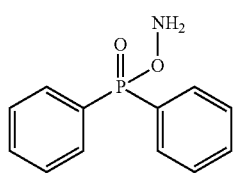

To hydroxylamine hydrochloride (15.86 g, 228.2 mmol) in water (35 mL) cooled in an ice-salt bath was added 7.1 N aqueous sodium hydroxide (27.4 mL, 194.4 mmol) followed by 1,4-dioxane (100 mL). The solution was vigorously stirred for 15 min and then chlorodiphenylphosphine oxide (20.00 g, 84.52 mmol) was added as a solution in 1,4-dioxane (100 mL). The solution was stirred an additional 15 min as a white precipitate formed. The precipitate was collected and then suspended in cold (0°) 0.25 N aqueous sodium hydroxide (250 mL). The mixture was stirred for 1 h and then the solid was collected, washed with water (100 mL), and thoroughly dried under vacuum to afford the desired intermediate (7.09 g, 36%) as a white solid. $^1$H-NMR (300 MHz, DMSO-$d_6$) δ 7.65-7.74 (m, 4H), 7.38-7.42 (m, 6H); $^{31}$P-NMR (DMSO-$d_6$) δ 23.11 (br s, 1P).

Step 5: Preparation of ethyl 1-amino-5-cyano-4-(nitrophenyl)-1H-pyrrole-3-carboxylate

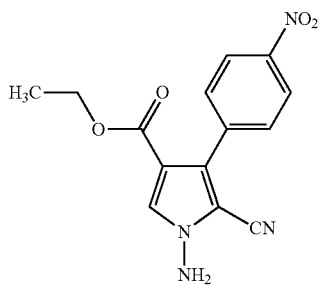

Sodium hydride (60% dispersion in mineral oil, 3.02 g, 75.6 mmol) was added to a solution ethyl 5-cyano-4-(nitrophenyl)-1H-pyrrole-3-carboxylate (17.97 g, 63.00 mmol) in DMF (625 mL). The solution was stirred at it for 15 min and then (aminooxy)(diphenyl)phosphine oxide (17.63 g, 75.59 mmol) was added, and the solution was heated (80° C.) for 17 h. Upon cooling to it aqueous saturated sodium bircarbonate solution (500 mL) was added followed by ethyl acetate (400 mL). The layers were separated and the aqueous layer was back extracted with ethyl acetate (2×200 mL). The combined organic layers dried over sodium sulfate and concentrated to dryness. The crude material was triturated with dichloromethane-hexanes (1:1 v/v 400 mL). The solid was collected, washed with hexanes (100 mL), and dried under vacuum. The material was suspended in ethyl acetate (500 mL) and, heated to reflux for 15 min, and then filtered. The filtrate was concentrated in vacuo to afford the desired product (14.15 g, 75%). $^1$H-NMR (300 MHz, DMSO-$d_6$) δ 8.25-8.31 (m, 2H), 7.73 (s, 1H), 7.67-7.73 (m, 2H), 6.71 (br s, 2H), 4.12 (q, J=7.1 Hz, 2H), 1.16 (t, J=7.1 Hz, 3H); HPLC RT (Method A) 2.91 min; TLC $R_f$=0.30 (95:5 v/v $CH_2Cl_2$-EtOAc).

Step 6: Preparation of the Title Compound

A solution of formamide (74.9 mL, 1.88 mol) and ethyl 1-amino-5-cyano-4-(nitrophenyl)-1H-pyrrole-3-carboxylate (14.15 g, 47.12 mmol) was heated (195° C.) for 2 h and the cooled to rt. Stirring was continued for 17 h and the resulting solid was collected and washed with ethyl acetate (2×100 mL) and water (100 mL). The solid was dried under vacuum to afford the desired product (10.20 g, 66%). $^1$H-NMR (300 MHz, DMSO-$d_6$) δ 8.23-8.29 (m, 2H), 8.20 (s, 1H), 8.05 (br s, 1H), 7.97 (s, 1H), 7.62 to 7.70 (m, 2H), 5.52 (br s, 1H), 4.08 (q, J=7.1 Hz, 2H), 1.09 (t, J=7.1 Hz, 3H); ES-MS m/z 328.1 (MH)$^+$; HPLC RT (Method A) 2.51 min; TLC $R_f$=0.20 (3:1 v/v $CH_2Cl_2$-EtOAc).

Intermediate B

Preparation of ethyl 4-amino-5-(4-aminophenyl)pyrrolo[2,1-f][1,2,4]triazine-6-carboxylate

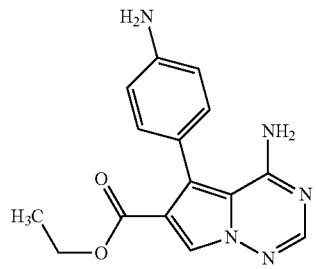

Raney nickel was added to a flask containing ethanol (20 mL). The catalyst was triturated with ethanol (3×20 mL) and the a suspension of ethyl 4-amino-5-(4-nitrophenyl)pyrrolo [2,1-f][1,2,4]triazine-6-carboxylate (4.0 g, 12.2 mmol) in ethanol (600 mL) and THF (200 mL) was added. The reaction was then placed under a hydrogen atmosphere (1 atm) and allowed to stir at rt overnight. The reaction was filtered through a pad of Celite® using a mixture of ethanol and THF (3:1) to rinse. The filtrate was concentrated in vacuo to afford the desired product (3.60 g, 96%). $^1$H-NMR (DMSO-$d_6$) δ 8.05 (s, 1H), 8.04 (br s, 2H), 7.88 (s, 1H), 7.01 (d, J=8.0 Hz, 2H), 6.61 (d, J=8.0 Hz, 2H), 5.31 (br s, 2H), 4.07 (q, J=7.3 Hz, 2H), 1.12 (t, J=7.3 Hz, 3H); ES-MS m/z 298.2 (MH)$^+$; HPLC RT (Method A) 1.64 min; TLC $R_f$=0.30 (Acetone/$CH_2Cl_2$ 1:3).

Intermediate C

Preparation of 4-amino-5-(4-aminophenyl)-N-(2,2,2-trifluoroethyl)pyrrolo[2,1-f][1,2,4]triazine-6-carboxamide

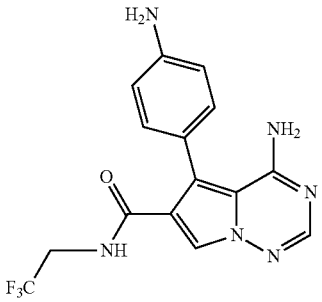

Step 1: Preparation of 4-amino-5-(4-nitrophenyl) pyrrolo[2,1-f][1,2,4]triazine-6-carboxylic acid

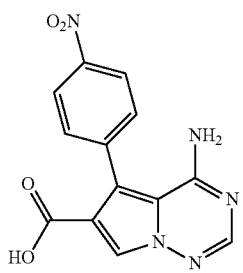

A suspension of ethyl 4-amino-5-(4-nitrophenyl)pyrrolo [2,1-f][1,2,4]triazine-6-carboxylate (1.04 g, 3.18 mmol) in ethanol (10 mL), THF (5 mL) and 1N aqueous sodium hydroxide solution (5.56 mL, 5.56 mmol) was heated (80° C.) for 6 h. The homogeneous solution was cooled to rt and treated dropwise with 1N hydrochoric acid (5.56 mL). The

Step 2: Preparation of 4-amino-5-(4-nitrophenyl)-N-(2,2,2-trifluoroethyl)pyrrolo[2,1-f][1,2,4]triazine-6-carboxamide

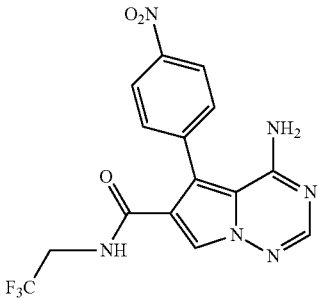

A solution 4-amino-5-(4-nitrophenyl)pyrrolo[2,1-f][1,2,4]triazine-6-carboxylic acid (495 mg, 1.73 mmol) in thionyl chloride (15 mL) was heated (50° C.) for 3 h. Upon cooling to rt the reaction mixture was concentrated to dryness. The resulting acid chloride intermediate was combined with 2,2,2-trifluoro-ethylamine hydrochloride salt (587 mg, 4.33 mmol), triethylamine (1.15 ml, 8.66 mmol), and THF (8 mL). The reaction was stirred for 16 h and then concentrated in vacuo. The residue was dissolved in ethyl acetate (50 mL) and then washed with water. The organic layer was dried over sodium sulfate and concentrated in vacuo. The residue was tritureated with ethyl acetate and methanol to afford the desired product (490 mg, 74%). $^1$H-NMR (300 MHz, DMSO-$d_6$) δ 8.77 (t, J=6.2 Hz, 1H), 8.29 (s, 1H), 8.23 (d, J=8.9 Hz, 2H), 7.97 (s, 1. H), 7.59 (d, J=8.9 Hz, 2H), 3.91-3.99 (m, 2H); ES-MS m/z 381.1 (MH)$^+$; HPLC RT (Method B) 2.33 min.

Step 3: Preparation of the Title Compound

The procedure used for the preparation of Intermediate B was used to prepare the title compound by substituting 4-amino-5-(4-nitrophenyl)-N-(2,2,2-trifluoroethyl)pyrrolo[2,1-f][1,2,4]triazine-6-carboxamide for Intermediate A. $^1$H-NMR (300 MHz, CD$_3$OD) δ 8.00 (s, 1H), 7.81 (s, 1H), 7.17 (d, J=8.5 Hz, 2H), 6.84 (d, J=8.6 Hz, 2H), 3.85-4.03 (m, 2H); ES-MS 315.2 (MH)$^+$; HPLC RT (Method A) 1.14 min.

Intermediate D

Preparation of ethyl 4-amino-5-(4-amino-3-fluorophenyl)pyrrolo[2,1-f][1,2,4]triazine-6-carboxylate

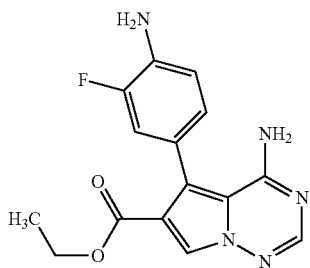

Step 1: Preparation of ethyl 3-(3-fluoro-4-nitrophenyl)-3-oxopropanoate

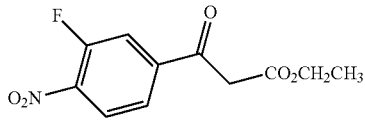

Thionyl chloride (96.4 g, 810 mmol) was added dropwise (30 min) to a solution of 3-fluoro-4-nitrobenzoic acid (100 g, 540 mmol) in 1,2-dichloroethane (500 mL) and DMF (1 mL). The reaction was warmed (70° C.) for 4 h and cooled to rt. Volatiles were evaporated under reduced pressure to afford the intermediate acid chloride. This material was dissolved in THF (500 mL) and then filtered to remove residual solids.

Magnesium chloride was added to a cooled (10° C.) suspension of ethylpotassium malonate (276 g, 1620 mmol) and triethylamine (164 g, 1620 mmol) in THF (1500 mL). This mixture was stirred vigorously (overhead stirrer) for 12 h at rt, and then cooled (0° C.). The filtered acid chloride solution in THF was added dropwise (30 min). The reaction was allowed to warm to rt, stirred for 12 h and then cooled (10° C.). 4 N hydrochloric acid (1 L) was added slowly, while maintaining the reaction temperature below 20° C. The quenched reaction was diluted with water (1 L) and then extracted with ethyl acetate (3×1 L). The combined organic extracts were washed with saturated aqueous sodium bicarbonate solution (2×1 L), water (1 L) and brine (1 L), dried over sodium sulfate, and evaporated under reduced pressure to afford the desired product (134 g, 97%) as a mixture of tautomers. $^1$H-NMR (300 MHz, DMSO-$d_6$) Tautomer 1: δ 12.24 (s, 1H), 7.85-8.32 (m, 3H), 6.22 (s, 3H), 4.25 (q, J=7.0 Hz, 2H), 1.26, (t, J=7.0 Hz, 3H); Tautomer 2: δ 7.90-8.38 (m, 3H), 4.30 (s, 2H), 4.11 (q, J=7.1 Hz, 2H), 1.17 (t, J=7.1 Hz, 3H); ES-MS m/z 254.1 (M-H)$^-$; HPLC RT (Method C) 3.14 min.

Step 2: Preparation of ethyl 2-(3-fluoro-4-nitrobenzoyl)-3-(dimethylamino)acrylate

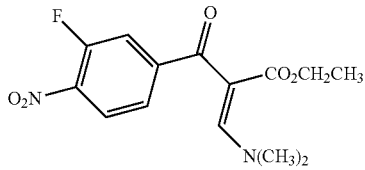

N,N-Dimethylformamide dimethyl acetal (100 g, 810 mmol) was added dropwise (10 min) to a cooled (0° C.) solution of ethyl 3-(3-fluoro-4-nitrophenyl)-3-oxopropanoate (138 g, 540 mmol) in toluene (540 mL). The reaction was warmed (50° C.) for 2.5 h and then the volatiles were evaporated under reduced pressure to afford the desired product (167 g, 100%), which was sufficiently pure (>95% by NMR) to proceed without further purification. $^1$H NMR (300 MHz, DMSO-$d_6$) δ 8.24-8.29 (m, 1H), 7.92 (s, 1H), 7.60-7.74 (m, 1H), 7.58-7.62 (m, 1H), 3.97 (q, J=7.0 Hz, 2H), 3.44 (s, 3H), 2.81 (s, 3H), 0.99 (t, J=7.0 Hz, 3H); ES-MS m/z 310.9 (MH)$^+$; HPLC RT (Method B) 2.87 min.

Step 3: Preparation of ethyl 5-carbamoyl-4-(3-chloro-4-nitrophenyl)-1H-pyrrole-3-carboxylate

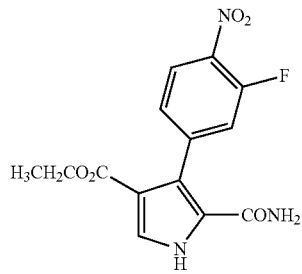

2-Aminomalonamide (36.5 g, 312 mmol) was added to a stirred solution of ethyl 2-(3-fluoro-4-nitrobenzoyl)-3-(dimethylamino)acrylate (74.4 g, 240 mmol) in acetic acid (300 mL). The suspension was warmed (80° C.) for 2 h and then the acetic acid was evaporated under reduced pressure. The residue was dissolved in trifluoroacetic acid (300 mL) and the resulting solution was warmed (60° C.) for 4 h. The trifluoroacetic acid was evaporated under reduced pressure and the solid was washed with cold ethanol (2×50 mL) and diethyl ether (3×50 mL) to afford the desired product (58.8 g, 76%). $^1$H NMR (300 MHz, DMSO-$d_6$) δ 12.35 (s, 1H), 8.12 (dd, J=8.3, 8.3 Hz, 1H), 7.63 (s, 1H), 7.52 (d, J=12.3 Hz, 1H), 7.25-7.50 (m, 2H), 6.74 (s, 1H), 4.06 (q, J=7.1 Hz, 2H), 1.11 (t, J=7.1 Hz, 3H); ES-MS m/z 322.0 (MH)$^+$; HPLC RT (Method B) 2.79 min.

Step 4: Preparation of ethyl 5-cyano-4-(3-fluoro-4-nitrophenyl)-1H-pyrrole-3-carboxylate

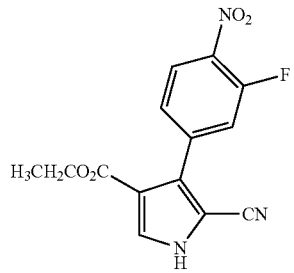

Phosphorous oxychloride (87.0 g, 565 mmol) was added to a suspension of ethyl 5-carbamoyl-4-(3-chloro-4-nitrophenyl)-1H-pyrrole-3-carboxylate (121 g, 377 mmol) in toluene (750 mL) equipped with an overhead stirrer. The suspension was heated (80° C.) and stirred for 6 h with the periodic addition of toluene (200 mL total) to rinse solids from the sides of the flask, and then the volatiles were evaporated under reduced pressure. The residue was suspended in toluene (500 mL) and this was evaporated to remove remaining phosphorous oxychloride (this operation was done two times). Cold water (750 mL) was added and the mixture was adjusted to pH 8 using 5 N aqueous sodium hydroxide. The solid was collected by filtration and dried to afford the desired product (110 g, 96%); $^1$H NMR (300 MHz, DMSO-$d_6$) δ 12.90 (s, 1H), 7.75 (s, 1H), 7.07 (dd, J=8.2, 8.2 Hz, 1H), 7.77 (dd, J=12.4, 1.8 Hz, 1H), 7.51-7.62 (m, 1H), 4.16 (q, J=7.1 Hz, 2H), 1.19 (t, J=7.1 Hz, 3H); ES-MS m/z 304.1 (MH)$^+$; HPLC RT (Method A) 3.19 min.

Step 5: Preparation of ethyl 4-(4-amino-3-fluorophenyl)-5-cyano-1H-pyrrole-3-carboxylate

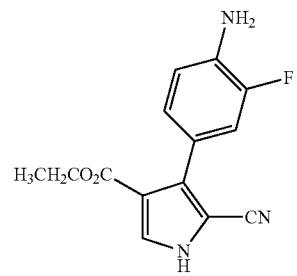

Iron (Alrich cat#20930-9, 24.9 g, 445 mmol) and ammonium chloride (4.80 g, 89.7 mmol) were added to a suspension of ethyl 5-cyano-4-(3-fluoro-4-nitrophenyl)-1H-pyrrole-3-carboxylate (45.0 g, 148 mmol) in ethanol (540 mL) and water (180 mL) equipped with an overhead stirrer. The reaction was warmed (70° C.) for 2 h, and then cooled to rt. The mixture was diluted with methanol (500 mL) and then filtered through a well-packed pad of Celite®. The filter cake was thoroughly rinsed with methanol (1 L) and acetonitrile (2 L) and the combined filtrate was evaporated. The residue was dissolved in ethyl acetate (1.5 L) then washed with water (500 mL) and brine (500 mL). The organic layer was dried over sodium sulfate and evaporated under reduced pressure to afford the desired product (38.0 g, 94%) containing trace impurities (<5%). The material was used in the next step without further purification. $^1$H NMR (300 MHz, DMSO-$d_6$) δ 13.36 (s, 1H), 8.25 (dd, J=12.8, 2.0 Hz, 1H), 6.92-6.97 (m, 1H), 6.72-6.79 (m, 1H), 5.35 (s, 2H), 4.10 (q, J=7.0 Hz, 2H), 1.16 (t, J=7.0 Hz, 3H); ES-MS m/z 274.3 (MH)$^+$; HPLC RT (Method A) 2.62 min.

Step 6: Preparation of ethyl 1-amino-4-(4-amino-3-fluorophenyl)-5-cyano-1H-pyrrole-3-carboxylate

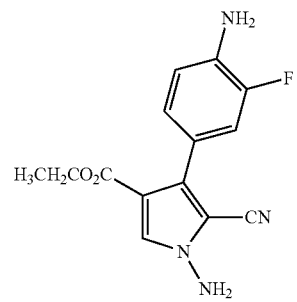

Sodium hydride (60% dispersion in oil, 1.7 g, 43 mmol) was added in portions to a solution of ethyl 4-(4-amino-3-fluorophenyl)-5-cyano-1H-pyrrole-3-carboxylate (9.0 g, 33 mmol) in DMF (290 mL). The suspension was stirred for 30 min and then (aminooxy)(diphenyl)phosphine oxide (9.9 g, 43 mmol) was added. The reaction was warmed (60° C.) for 4 h and then cooled to rt. The reaction was quenched by slow addition of water (10 mL) and the solvents were evaporated under reduced pressure. The residue was dissolved in ethyl acetate (500 mL) and the solution was washed with saturated aqueous sodium bicarbonate solution (2×250 mL) and brine (250 mL). The organic layer was dried over sodium sulfate and evaporated. The residue was triturated with diethyl ether to give the desired product (7.8 g, 82%); $^1$H NMR (300 MHz, DMSO-$d_6$) δ 7.57 (s, 1H), 7.05 (dd, J=12.7, 2.0 Hz, 1H), 6.91-6.95 (m, 1H), 6.75 (dd, J=9.5, 8.4 Hz, 1H), 6.57 (s, 2H), 5.36 (s, 2H), 4.09 (q, J=7.0 Hz, 2H), 1.16 (t, J=7.0 Hz, 3H); ES-MS m/z 289.0 (MH)$^+$; HPLC RT (Method B) 2.61 min.

Step 7: Preparation of the Title Compound

Formamidine acetate (22.4 g, 215 mmol) was added to a suspension of ethyl 1-amino-4-(4-amino-3-fluorophenyl)-5-cyano-1H-pyrrole-3-carboxylate (6.2 g, 21.5 mmol) in n-butanol (100 mL). The reaction was heated (100° C.) for 16 h and then cooled to rt. The solvent was removed under reduced pressure and then ethanol (50 mL) and water (200 mL) were added. The mixture was stirred for 30 min and the resulting precipitate was collected by filtration. The solid was washed with water (2×50 mL) and dried to afford desired product (5.80 g, 85%); $^1$H NMR (300 MHz, DMSO-$d_6$) δ 8.08 (s, 1H), 8.00-8.10 (br s, 1H), 7.90 (s, 1H), 7.03 (dd, J=12.3, 1.9 Hz, 1H), 6.77-6.88 (m, 2H), 5.36 (s, 2H), 5.21-5.31 (br s, 1H), 4.06 (q, J=7.1 Hz, 2H), 1.11 (t, J=7.1 Hz, 3H); ES-MS m/z 316.4 (MH)$^+$; HPLC RT (Method B) 2.39 min.

Intermediate E

Preparation of 4-amino-5-(4-amino-3-fluorophenyl)-N-(2,2,2-trifluoroethyl)pyrrolo[2,1-f][1,2,4]triazine-6-carboxamide

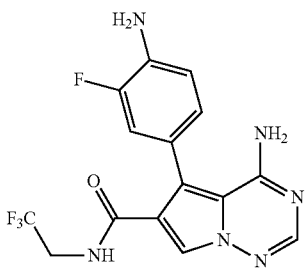

Step 1: Preparation of 4-amino-5-(4-amino-3-fluorophenyl)pyrrolo[2,1-f][1,2,4]triazine-6-carboxylic acid

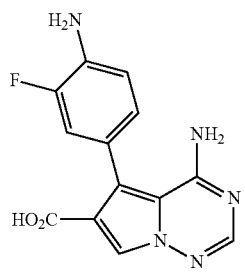

1 N aqueous sodium hydroxide (253 mL, 253 mmol) was added to a suspension of ethyl 4-amino-5-(4-amino-3-fluorophenyl)pyrrolo[2,1-f][1,2,4]triazine-6-carboxylate (40.0 g, 127 mmol) in THF (400 mL) and ethanol (400 mL). The reaction mixture was heated (65° C.) for 16 h and then cooled to rt. Hydrogen chloride (4 N in 1,4-dioxane, 70 mL, 280 mmol) was added and the volatiles were removed under reduced pressure. The residue was washed with water (200 mL) and then triturated with acetone and diethyl ether to give the desired product (36.3 g 99%) containing trace impurities. $^1$H NMR (300 MHz, DMSO-$d_6$) δ 12.20-12.30 (br s, 1H), 8.03 (s, 1H), 7.94-8.05 (br s, 1H), 7.89 (s, 1H), 7.02 (dd, J=12.4, 2.0 Hz, 1H), 6.73-6.92 (m, 2H), 5.22-5.47 (br s, 1H), 5.12-5.25 (br s, 1H); ES-MS m/z 288.0 (MH)$^+$; HPLC RT (Method A) 1.13 min.

Step 2: Preparation of the Title Compound 4-amino-5-(4-amino-3-fluorophenyl)pyrrolo[2,1-f][1,2,4]triazine-6-carboxylic acid (24.6 g, 85.6 mmol) was added to a mixture of 2,2,2-trifluoro-1-aminoethane (42.4 g, 428 mmol), benzotriazolyloxytris(dimethylamino)phosphonium PF6 (56.8 g, 128 mmol) and 4-methylmorpholine (43.3 g, 428 mmol) in DMF (500 mL). The reaction mixture was stirred at rt for 16 h. The resulting precipitate was isolated by filtration and then washed with acetone and diethyl ether to give the desired product (22 g, 70%); $^1$H NMR (300 MHz, DMSO-$d_6$) δ 8.37 (dd, J=8.5, 8.5 Hz, 1H), 8.12 (s, 1H), 7.94 (s, 1H), 7.92-8.03 (br s, 1H), 7.89 (s, 1H), 6.99 (dd, J=12.2, 1.8 Hz, 1H), 6.85 (dd, J=12.2, 1.8 Hz, 1H), 6.74-6.6.82 (m, 1H), 5.35 (s, 2H), 5.13-3.22 (br s, 1H), 3.87-4.01 (m, 2H); ES-MS m/z 369.2 (MH)$^+$; HPLC RT (Method B) 2.05 min.

Intermediate F

Preparation of ethyl 4-amino-5-{4-[(5,7-difluoro-1H-benzimidazol-2-yl)amino]phenyl}pyrrolo[2,1-f][1,2,4]triazine-6-carboxylate

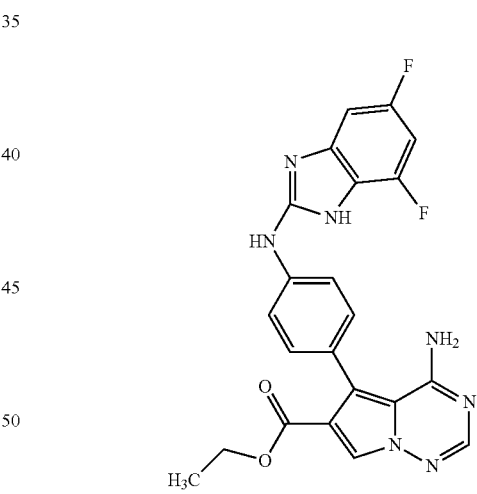

To a solution of 4-amino-5-(4-aminophenyl)-N-(2,2,2-trifluoroethyl)pyrrolo[2,1-f][1,2,4]triazine-6-carboxamide (200 mg, 0.673 mmol) in DMF (5 mL) and THF (5 mL) was added 1,1'-thiocarbonyldiimidazole (125 mg, 0.706 mmol). The reaction was stirred at it for 3 hr and then 1,2-diamino-3,5-difluorobenzene (101 mg, 0.706 mmol) was added. Stirring was continued overnight and then N,N'-diisopropylcarbodiimide (0.527 ml, 3.36 mmol) was added dropwise. The reaction was again allowed to stir overnight and then the mixture was concentrated under reduced pressure. The crude residue was purified by HPLC using 25-85% acetonitrile/water to give the desired product (205 mg, 68%); $^1$H NMR (300 MHz, DMSO-$d_6$) δ 11.31-11.40 (br s, 1H), 9.75-9.83 (br s, 1H), 8.14 (s, 1H), 8.02-8.13 (br s, 1H), 7.93 (s, 1H), 7.82

(d, J=8.6 Hz, 2H), 7.35 (d, J=8.6 Hz, 2H), 6.94-7.05 (br d, 1H), 6.86 (ddd, J=10.7, 10.7, 2.2 Hz, 1H), 5.15-5.46 (br s, 1H), 4.08 (q, J=7.1 Hz, 2H), 1.10 (t, J=7.1 Hz, 3H); ES-MS m/z 450.1 (MH)+; HPLC RT (Method A) 2.48 min.

Intermediate G

Preparation of ethyl 4-amino-5-{-4-[(7-fluoro-6-phenoxy-1H-benzimidazol-2-yl)amino]phenyl}pyrrolo[2,1-f][1,2,4]triazine-6-carboxylate

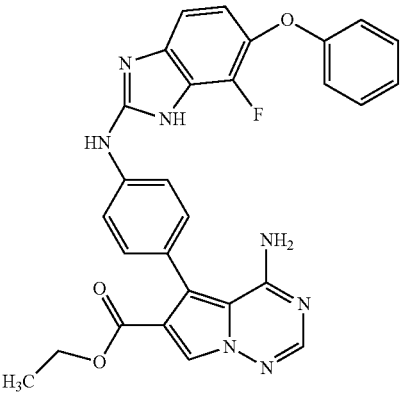

The procedure used for the preparation of Intermediate F was used to prepare the title compound by substituting 1,2-diamino-3,5-difluorobenzene for 3-fluoro-4-phenoxybenzene-1,2-diamine. $^1$H NMR (300 MHz, DMSO-d$_6$) δ 11.32 (s, 1H), 9.86 9 s, 1H), 7.13 (s, 1H), 8.03-8.12 (br s, 1H), 7.93 (s, 1H), 7.83 (d, J=8.6 Hz, 2H), 7.28-7.40 (m, 4H), 7.13 (d, J=8.4 Hz, 1H), 7.02 (dd, J=7.5, 7.5 Hz, 1H), 6.89 (d, J=8.0 Hz, 1H), 6.84 (dd, J=7.8, 7.8 Hz, 1H), 4.08 (q, J=7.1 Hz, 2H), 1.10 (t, J=7.1 Hz, 3H); ES-MS m/z 524.3 (MH)+; HPLC RT (Method B) 2.89 min.

Intermediate H

Preparation of ethyl 4-amino-5-(4-{[5-(trifluoromethyl)-3H-imidazo[4,5-b]pyridin-2-yl]amino}phenyl)pyrrolo[2,1-f][1,2,4]triazine-6-carboxylate

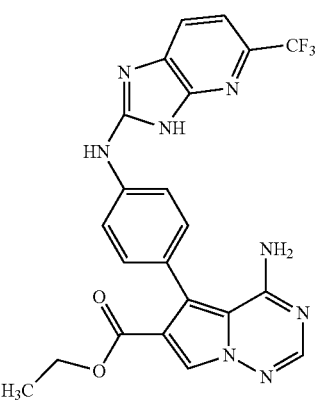

The procedure used for the preparation of Intermediate F was used to prepare the title compound by substituting 6-(trifluoromethyl)pyridine-2,3-diamine for 1,2-diamino-3,5-difluorobenzene. $^1$H NMR (300 MHz, DMSO-d$_6$) δ 11.5 (br s, 1H), 10.25 (br s, 2H), 8.15 (s, 2H), 7.85-7.95 (m, 3H), 7.35-7.42 (m, 2H), 7.15 (s, 1H), 5.1 (br s, 1H), 4.07 (q, J=7.2 Hz, 2H), 1.06 (t, J=7.1 Hz, 3H). ES-MS m/z 483.2 (MH)+; HPLC RT (Method B) 2.83 min.

Intermediate I

Preparation of 4-amino-5-(4-amino-3-fluorophenyl)-N-tert-butylpyrrolo[2,1-f][1,2,4]triazine-6-carboxamide

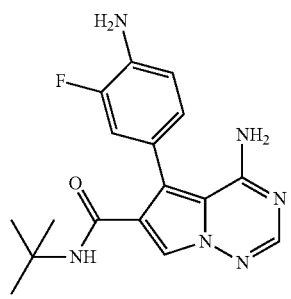

The procedure used for the preparation of Intermediate D was used to prepare the title compound by substituting t-butylamine for 2,2,2-trifluoro-1-aminoethane. $^1$H NMR (300 MHz, DMSO-d$_6$) δ 7.96 (s, 1H), 7.87 (s, 1H), 7.07 (dd, J=12.3, 1.9 Hz, 1H), 6.92 (dd, J=8.1, 1.9 Hz, 1H), 6.81-6.6.89 (m, 1H), 5.44 (s, 2H), 1.16 (s, 9H); ES-MS m/z 343.1 (MH)+; HPLC RT (Method A) 2.11 min.

Intermediate J

Preparation of 3-fluoro-4-phenoxybenzene-1,2-diamine

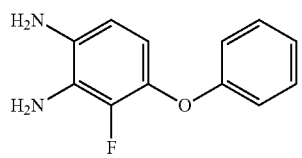

Step 1: Preparation of 2-fluoro-6-nitro-3-phenoxyaniline

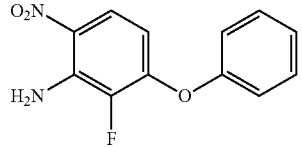

To a solution of 2,3-difluoro-6-nitroaniline (200 mg, 1.15 mmol) in DMF (10 ml) was added phenol (108 mg, 1.15 mmol) and potassium carbonate (317 mg, 2.30 mmol). The reaction was heated (120° C.) overnight and then cooled to rt. The reaction was diluted with ethyl acetate (200 mL) and then washed with water (2×100 mL) and brine (100 mL). The organic layer was dried over sodium sulfate, filtered and concentrated under reduced pressure. The residue was purified by silica gel chromatography using 0-50% ethylacetate/hexane to afford the desired product (267 mg, 94%) $^1$H NMR (300 MHz, DMSO-$d_6$) δ 7.85 (dd, J=9.8, 2.2 Hz, 1H), 7.34-7.49 (m, 4H), 7.19-7.27 (m, 1H), 7.08-7.16 (m, 2H), 6.21 (dd, J=9.7, 7.8 Hz, 1H); HPLC RT (Method A) 3.48 min.

Step 2: Preparation of the Title Compound

To a solution of 2-fluoro-6-nitro-3-phenoxyaniline (260 mg, 1.05 mmol) in methanol (20 ml) was added tin(II)chloride (1.18 g, 5.24 mmol). The reaction was heated to reflux overnight and then cooled to rt. The mixture was concentrated under reduced pressure and the residue was dissolved in ethyl acetate (50 mL). The solution was poured into an aqueous saturated sodium bicarbonate solution (150 mL), causing a precipitate to crash out. The mixture was filtered using ethyl acetate to rinse. The filtrate was washed with water and brine, dried over sodium sulfate, and then concentrated under reduced pressure. The residue was purified by silica gel chromatography using 0-70% ethyl acetate/hexane to yield the desired product (195 mg, 85%) $^1$H NMR (300 MHz, DMSO-$d_6$) δ 7.22-7.31 (m, 2H), 6.94-7.01 (m, 1H), 6.82 (d, J=7.8 Hz, 2H), 6.31 (dd, J=8.5, 1.5 Hz, 1H), 6.20 (dd, J=8.5, 8.5 Hz, 1H); ES-MS m/z 219.3 (MH)$^+$; HPLC RT (Method A) 2.40 min.

By using the method described above for Intermediate J, and by substituting the appropriate starting materials, Intermediates K-R found in the table below were similarly prepared.

TABLE 1

| Int | Name | Structure | LC-MS m/z (MH)$^+$ RT (min) [Method] |
|---|---|---|---|
| K | 3-fluoro-4-(4-methylphenoxy)-benzene-1,2-diamine | 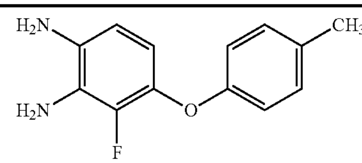 | 233.3 2.61 [Method B] |
| L | 3-fluoro-4-(4-fluorophenoxy)-benzene-1,2-diamine | 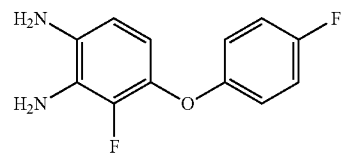 | 237.3 2.51 [Method B] |
| M | 3-fluoro-4-(2-fluorophenoxy)-benzene-1,2-diamine | 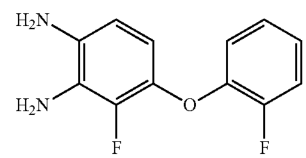 | 237.2 2.57 [Method A] |
| N | 3-fluoro-4-(3-fluorophenoxy)-benzene-1,2-diamine | 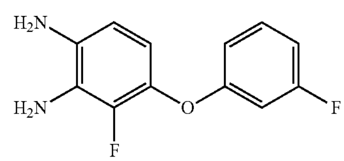 | 237.2 2.76 [Method A] |
| O | 3-fluoro-4-(2-methylphenoxy)-benzene-1,2-diamine | 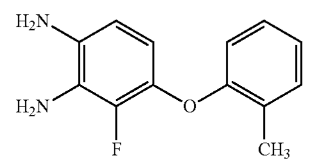 | 233.2 2.41 [Method A] |
| P | 3-fluoro-4-(2-methylphenoxy)-benzene-1,2-diamine | 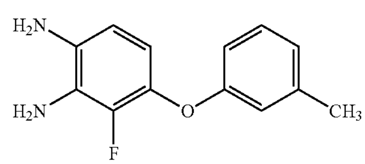 | 233.3 2.65 [Method B] |
| Q | 3-fluoro-$N^4$-isopropylbenzene-1,2,4-triamine | 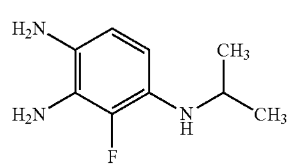 | 184.1 1.09 [Method B] |

Intermediate R

Preparation of 3-fluoro-4-pyrrolidin-1-ylbenzene-1,2-diamine

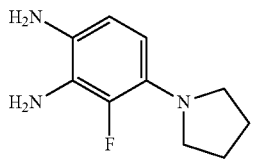

Step 1: Preparation of 2-fluoro-6-nitro-3-pyrrolidin-1-ylaniline

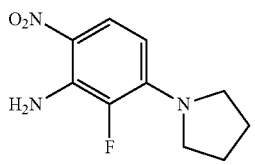

The procedure used for Step 1 in the preparation of Intermediate J was used to prepare 2-fluoro-6-nitro-3-pyrrolidin-1-ylaniline by substituting phenol for pyrrolidine. $^1$H NMR (300 MHz, DMSO-$d_6$) δ 7.68 (dd, J=9 k. 8, 1.4 Hz, 1H), 7.04 (s, 2H), 6.13 (dd, J=9.9, 8.5 Hz, 1H), 3.31-3.53 (m, 4H), 1.85-1.92 (m, 4H); ES-MS m/z 226.0 (MH)$^+$; HPLC RT (Method A) 3.22 min.

Step 2: Preparation of the Title Compound

To a mixture of 2-fluoro-6-nitro-3-pyrrolidin-1-ylaniline (285 mg, 1.26 mmol) in ethanol (20 ml) was added a slurry of Raney nickel (approximately 100 mg) in ethanol. The mixture was stirred under a hydrogen atmosphere (1 atm) at rt overnight. The reaction was purged of hydrogen, flushed with nitrogen and then filtered through a pad of Celite® using ethanol to rinse. The filtrate was concentrated under reduced pressure to afford crude product (43 mg, 17%) which was used without purification. $^1$H NMR (300 MHz, DMSO-$d_6$) δ 6.19 (dd, J=8.4, 1.5 Hz, 1H), 5.89 (dd, J=8.4, 8.4 Hz, 1H), 4.30 (s, 2H), 4.20 (s, 2H), 2.94-3.07 (m, 4H), 1.72-1.89 (m, 4H); ES-MS m/z 196.3 (MH)$^+$; HPLC RT (Method B) 1.08 min.

Intermediate S

Preparation of 4-(4-fluorophenoxy)benzene-1,2-diamine

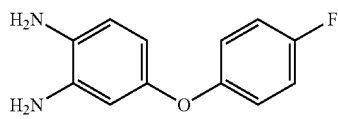

The procedure used for the preparation of Intermediate J was used to prepare the title compound by substituting 4-chloro-6-nitroaniline for 2,3,-difluoro-6-nitroaniline and 4-fluorophenol for phenol. $^1$H-NMR (300 MHz, DMSO-$d_6$) δ 7.06-7.15 (m, 2H), 6.82-6.90 (m, 2H), 6.47 (d J=8.2 Hz, 1H), 6.21 (d, J=2.7 Hz, 1H), 6.06 (dd, J=8.4, 2.7 Hz, 1H), 4.64 (s, 2H), 4.31 (s, 2H); ES-MS m/z 219.2 (MH)$^+$; HPLC RT (Method A) 1.07 min.

EXAMPLES

Example 1

Preparation of 4-amino-5-[4-(1H-benzimidazol-2-ylamino)phenyl]-N-(2,2,2-trifluoroethyl)pyrrolo[2,1-f][1,2,4]triazine-6-carboxamide

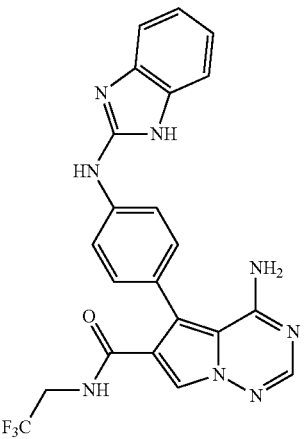

To a solution of 4-amino-5-(4-aminophenyl)-N-(2,2,2-trifluoroethyl)pyrrolo[2,1-f][1,2,4]triazine-6-carboxamide (100 mg, 0.285 mmol) in DMF (2.5 mL) was added 1,1'-thiocarbonyldiimidazole (53.4 mg, 0.299 mmol) at rt, under an inert atmosphere. The mixture was stirred at rt overnight. The following day, 1,2-phenylenediamine (32.4 mg, 0.299 mmol) was added and the mixture was stirred at rt for an additional 18 h. The following day, N,N'-diisopropylcarbodiimide (0.22 mL, 1.42 mmol) was added and the mixture was stirred at rt for additional 18 h. The mixture was then concentrated under reduced pressure and the residue was submitted to silica gel column chromatography using 2 to 8% MeOH/CH$_2$Cl$_2$ as the eluent. The desired product was obtained as yellowish solid (55 mg, 41%). $^1$H-NMR (300 MHz, DMSO-$d_6$) δ 11.00 (s, 1H), 9.60 (s, 1H), 8.51 (s, 1H), 8.20 (s, 1H), 8.00-8.20 (br s, 2H), 7.80-7.90 (m, 2H), 7.20-7.40 (m, 4H), 7.00 (d, J=4.3 Hz, 2H), 3.80-4.00 (m, 2H); ES-MS m/z 467.3 (MH)$^+$; HPLC RT (Method A) 2.30 min.

Example 2

Preparation of 4-amino-5-{4-[(6-cyano-1H-benzimidazol-2-yl)amino]phenyl}-N-(2,2,2-trifluoroethyl)pyrrolo[2,1-f][1,2,4]triazine-6-carboxamide

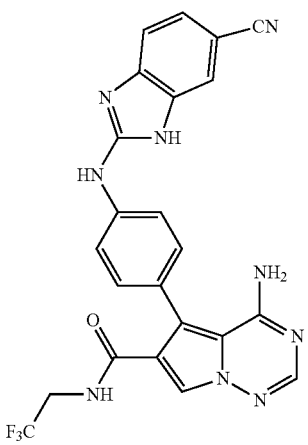

The procedure used for the preparation of Example 1 was used to prepare the title compound by substituting 3,4-diaminobenzonitrile for 1,2-phenylenediamine. ¹H-NMR (300 MHz, DMSO-d₆) δ 10.00 (s, 1H), 8.50 (s, 1H), 8.20 (s, 1H), 7.90 (s, 1H), 7.80 (d, J=6.3 Hz, 2H), 7.70 (s, 1H), 7.30-7.45 (m, 4H), 5.00 (br s, 2H), 3.80-4.00 (m, 2H); ES-MS m/z 492.1 (MH)⁺; HPLC RT (Method A) 2.24 min.

Example 3

Preparation of 4-amino-5-{4-[(7-hydroxy-1H-benzimidazol-2-yl)amino]phenyl}-N-(2,2,2-trifluoroethyl)pyrrolo[2,1-f][1,2,4]triazine-6-carboxamide

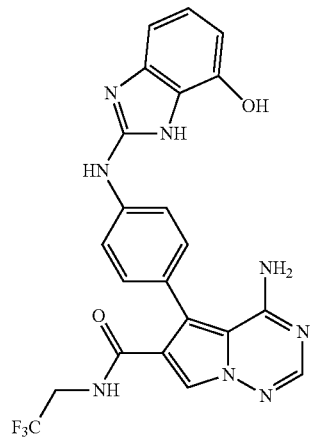

The procedure used for the preparation of Example 1 was used to prepare the title compound by substituting 2,3-diaminophenol for 1,2-phenylenediamine. ¹H-NMR (300 MHz, DMSO-d₆) δ 10.42 (s, 1H), 8.40 (s, 1H), 8.20 (s, 1H), 7.95 (s, 1H), 7.90 (d, J=7.9 Hz, 2H), 7.22 (d, J=7.5 Hz, 2H), 6.80-6.90 (m, 1H), 6.75 (d, J=7.6 Hz, 1H), 6.40 (d, J=7.7 Hz, 1H), 5.25 (br s, 2H), 3.80-4.00 (m, 2H); ES-MS m/z 483.1 (MH)⁺; HPLC RT (Method A) 2.49 min.

Example 4

Preparation of 4-amino-5-{4-[(6-chloro-1H-benzimidazol-2-yl)amino]phenyl}-N-(2,2,2-trifluoroethyl)pyrrolo[2,1-f][1,2,4]triazine-6-carboxamide

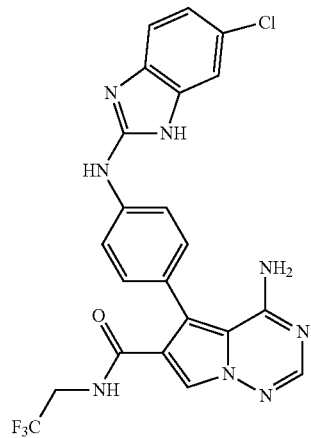

The procedure used for the preparation of Example 1 was used to prepare the title compound by substituting 4-chloro-o-phenylenediamine for 1,2-phenylenediamine. ¹H-NMR (300 MHz, DMSO-d₆) δ 9.78 (s, 1H), 8.49 (dd, J=6.4, 6.4 Hz, 1H), 8.20 (s, 1H), 7.95 (s, 1H), 7.81 (d, J=8.4 Hz, 2H), 7.22-7.40 (m, 3H), 6.98-7.05 (m, 2H), 5.12 (br s, 1H), 3.91-4.00 (m, 2H); ES-MS m/z 501.1 (MH)⁺; HPLC RT (Method A) 2.56 min.

Example 5

Preparation of 4-amino-N-(2,2,2-trifluoroethyl)-5-(4-{[6-(trifluoromethyl)-1H-benzimidazol-2-yl]amino}phenyl)pyrrolo[2,1-f][1,2,4]triazine-6-carboxamide

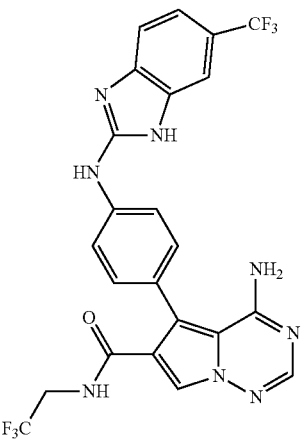

The procedure used for the preparation of Example 1 was used to prepare the title compound by substituting 4-(trifluoromethyl)-1,2-phenylenediamine for 1,2-phenylenediamine. ¹H-NMR (300 MHz, DMSO-d₆) δ 9.90 (s, 1H), 8.51 (dd, J=6.4, 6.4 Hz, 1H), 8.21 (s, 1H), 7.95 (s, 1H), 7.83 (d, J=8.4 Hz, 2H), 7.63 (s, 1H), 7.51 (d, J=8.4 Hz, 1H), 7.35-7.40 (m, 3H), 5.15 (br s, 1H), 3.92-4.05 (m, 2H); ES-MS m/z 535.0 (MH)⁺; HPLC RT (Method A) 2.46 min.

Example 6

Preparation of 4-amino-5-{4-[(5,7-difluoro-1H-benzimidazol-2-yl)amino]phenyl}-N-(2,2,2-trifluoroethyl)pyrrolo[2,1-f][1,2,4]triazine-6-carboxamide

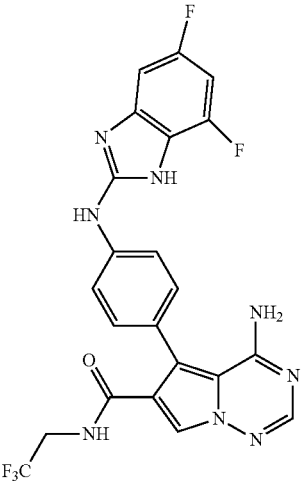

The procedure used for the preparation of Example 1 was used to prepare the title compound by substituting 3,5-difluoro-1,2-phenylenediamine for 1,2-phenylenediamine. $^1$H-NMR (300 MHz, DMSO-d$_6$) δ 9.80 (s, 1H), 8.52 (dd, J=6.4, 6.4 Hz, 1H), 8.21 (s, 1H), 7.95 (s, 1H), 7.82 (d, J=7.2 Hz, 2H), 7.38 (d, J=7.2 Hz, 2H), 7.05 (d, J=9.2 Hz, 1H), 6.85-6.90 (m, 1H), 5.18 (br s, 1H), 3.95-4.05 (m, 2H); ES-MS m/z 502.9 (MH)$^+$; HPLC RT (Method A) 2.33 min.

Example 7

Preparation of 4-amino-5-{4-[(6-fluoro-1H-benzimidazol-2-yl)amino]phenyl}-N-(2,2,2-trifluoroethyl)pyrrolo[2,1-f][1,2,4]triazine-6-carboxamide

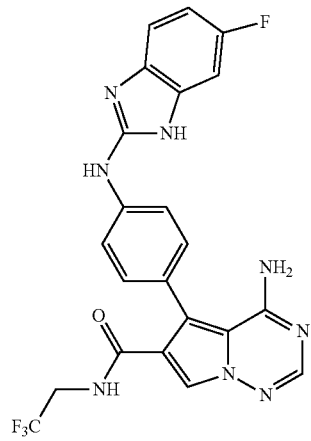

The procedure used for the preparation of Example 1 was used to prepare the title compound by substituting 4-fluoro-1,2-phenylenediamine for 1,2-phenylenediamine. $^1$H-NMR (300 MHz, DMSO-d$_6$) δ 9.71 (s, 1H), 8.48 (dd, J=8.4, 8.4 Hz, 1H), 8.19 (s, 1H), 7.91 (s, 1H), 7.80 (d, J=8.4 Hz, 2H), 7.32 (d, J=8.4 Hz, 2H), 7.25 (br s, 1H), 7.15 (d, J=8.8 Hz, 1H), 6.80 (dd, J=8.4, 8.4 Hz, 1H), 5.15 (br s, 1H), 3.91-4.02 (m, 2H); ES-MS m/z 485.0 (MH)$^+$; HPLC RT (Method A) 2.22 min.

Example 8

Preparation of 4-amino-5-{4-[(6-methoxy-1H-benzimidazol-2-yl)amino]phenyl}-N-(2,2,2-trifluoroethyl)pyrrolo[2,1-f][1,2,4]triazine-6-carboxamide

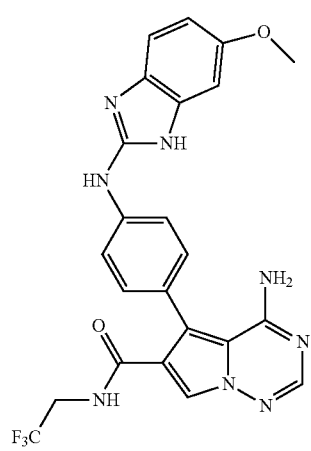

The procedure used for the preparation of Example 1 was used to prepare the title compound by substituting 4-methoxy-1,2-phenylenediamine for 1,2-phenylenediamine.

$^1$H-NMR (300 MHz, DMSO-d$_6$) δ 10.82 (s, 1H), 9.52 (s, 1H), 8.42 (br s, 1H), 8.19 (s, 1H), 7.95 (s, 1H), 7.81 (d, J=8.4 Hz, 2H), 7.31 (d, J=8.4 Hz, 2H), 7.20 (br s, 1H), 7.00 (d, J=10.8 Hz, 1H), 6.60 (br s, 1H), 5.17 (br s, 1H), 4.02-3.90 (m, 2H), 3.76 (s, 3H); ES-MS m/z 497.2 (MH)$^+$; HPLC RT (Method B) 1.31 min.

Example 9

Preparation of 4-amino-5-{4-[(6-bromo-1H-benzimidazol-2-yl)amino]phenyl}-N-(2,2,2-trifluoroethyl)pyrrolo[2,1-f][1,2,4]triazine-6-carboxamide

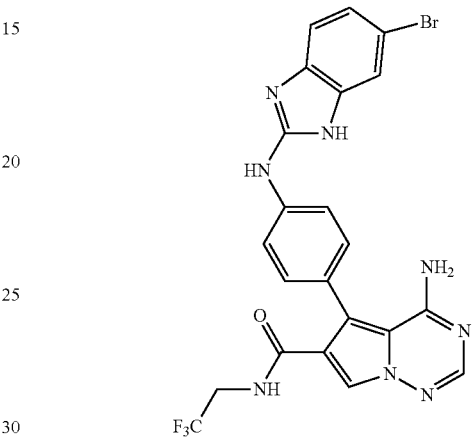

The procedure used for the preparation of Example 1 was used to prepare the title compound by substituting 4-bromo-1,2-phenylenediamine for 1,2-phenylenediamine. $^1$H-NMR (300 MHz, DMSO-d$_6$) δ 9.80 (s, 1H), 8.50 (dd, J=6.4, 6.4 Hz, 1H), 8.21 (s, 1H), 7.95 (s, 1H), 7.82 (d, J=8.4 Hz, 2H), 7.50 (br s, 1H), 7.15-7.39 (m, 4H), 5.13 (br s, 1H), 3.92-4.02 (m, 2H); ES-MS m/z 545.1 (MH)$^+$; HPLC RT (Method B) 1.58 min.

Example 10

Preparation of 4-amino-5-{4-[(6-tert-butyl-1H-benzimidazol-2-yl)amino]phenyl}-N-(2,2,2-trifluoroethyl)pyrrolo[2,1-f][1,2,4]triazine-6-carboxamide

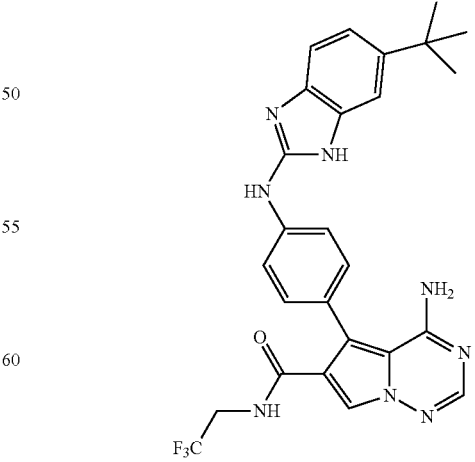

The procedure used for the preparation of Example 1 was used to prepare the title compound by substituting 4-(tert-butyl)benzene-1,2-diamine for 1,2-phenylenediamine.

¹H-NMR (300 MHz, DMSO-d₆) δ 9.60 (s, 1H), 8.48 (dd, J=6.4, 6.4 Hz, 1H), 8.21 (s, 1H), 7.95 (s, 1H), 7.82 (d, J=8.4 Hz, 2H), 7.63 (s, 1H), 7.40-7.22 (m, 4H), 5.15 (br s, 1H), 3.92-4.06 (m, 2H), 1.38 (s, 9H); ES-MS m/z 523.2 (MH)⁺; HPLC RT (Method A) 3.04 min.

Example 11

Preparation of 4-amino-5-{4-[(6-benzoyl-1H-benzimidazol-2-yl)amino]phenyl}-N-(2,2,2-trifluoroethyl)pyrrolo[2,1-f][1,2,4]triazine-6-carboxamide

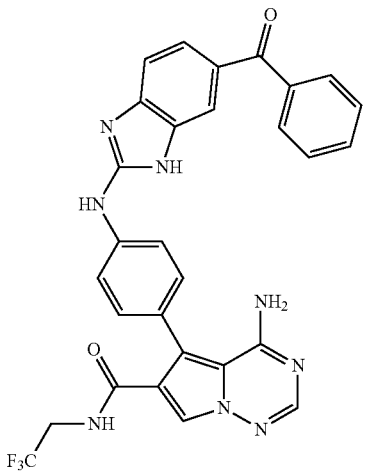

The procedure used for the preparation of Example 1 was used to prepare the title compound by substituting 3,4-diamino-benzophenone for 1,2-phenylenediamine. ¹H-NMR (300 MHz, DMSO-d₆) δ 10.01 (s, 1H), 8.53 (dd, J=6.4, 6.4 Hz, 1H), 8.21 (s, 1H), 7.96 (s, 1H), 7.82 (d, J=8.8 Hz, 2H), 7.70-7.80 (m, 3H), 7.50-7.62 (m, 4H), 7.48 (d, J=8.4 Hz, 1H), 7.38 (d, J=8.4 Hz, 2H), 5.18 (br s, 1H), 3.90-4.02 (m, 2H); ES-MS m/z 571.1 (MH)⁺; HPLC RT (Method A) 2.99 min.

Example 12

Preparation of 4-amino-5-{4-[(5,6-dichloro-1H-benzimidazol-2-yl)amino]phenyl}-N-(2,2,2-trifluoroethyl)pyrrolo[2,1-f][1,2,4]triazine-6-carboxamide

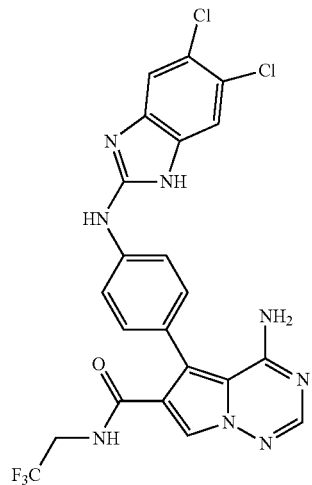

The procedure used for the preparation of Example 1 was used to prepare the title compound by substituting 4,5-dichloro-1,2-phenylenediamine for 1,2-phenylenediamine. ¹H-NMR (300 MHz, DMSO-d₆) δ 9.95 (s, 1H), 8.55 (dd, J=6.4, 6.4 Hz, 1H), 8.21 (s, 1H), 7.95 (s, 1H), 7.82 (d, J=8.4 Hz, 2H), 7.62 (s, 1H), 7.58 (s, 1H), 7.38 (d, J=8.4 Hz, 2H), 5.15 (br s, 1H), 3.95-4.05 (m, 2H); ES-MS m/z 534.9 (MH)⁺; HPLC RT (Method A) 2.53 min.

Example 13

Preparation of 4-amino-5-{4-[(6-chloro-5-fluoro-1H-benzimidazol-2-yl)amino]phenyl}-N-(2,2,2-trifluoroethyl)pyrrolo[2,1-f][1,2,4]triazine-6-carboxamide

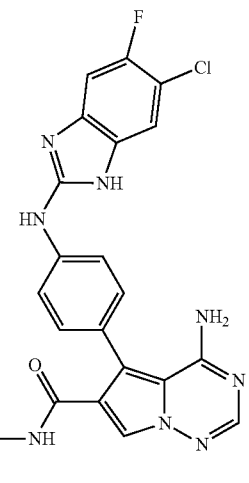

The procedure used for the preparation of Example 1 was used to prepare the title compound by substituting 4-chloro-5-fluoro-1,2-phenylenediamine for 1,2-phenylenediamine. ¹H-NMR (300 MHz, DMSO-d₆) δ 9.83 (s, 1H), 8.55 (dd, J=6.4, 6.4 Hz, 1H), 8.21 (s, 1H), 7.95 (s, 1H), 7.82 (d, J=8.4 Hz, 2H), 7.28-7.34 (m, 4H), 5.15 (br s, 1H), 4.04-3.95 (m, 2H); ES-MS m/z 518.9 (MH)⁺; HPLC RT (Method A) 2.39 min.

Example 14

Preparation of 4-amino-5-{4-[(5,6-difluoro-1H-benzimidazol-2-yl)amino]phenyl}-N-(2,2,2-trifluoroethyl)pyrrolo[2,1-f][1,2,4]triazine-6-carboxamide

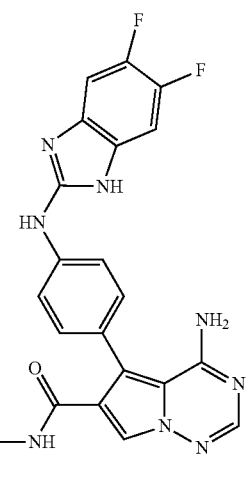

The procedure used for the preparation of Example 1 was used to prepare the title compound by substituting 4,5-difluoro-1,2-phenylenediamine for 1,2-phenylenediamine. ¹H-NMR (300 MHz, DMSO-d₆) δ 9.80 (s, 1H), 8.52 (dd, J=6.4, 6.4 Hz, 1H), 8.21 (s, 1H), 7.95 (s, 1H), 7.82 (d, J=8.4 Hz, 2H), 7.30-7.40 (m, 4H), 5.19 (br s, 1H), 3.96-4.04 (m, 2H); ES-MS m/z 502.9 (MH)⁺; HPLC RT (Method A) 2.30 min.

Example 15

Preparation of 4-amino-5-{4-[(5,6-dimethyl-1H-benzimidazol-2-yl)amino]phenyl}-N-(2,2,2-trifluoroethyl)pyrrolo[2,1-f][1,2,4]triazine-6-carboxamide

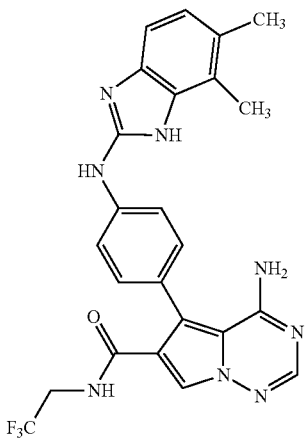

The procedure used for the preparation of Example 0.1 was used to prepare the title compound by substituting 3,4-dimethyl-1,2-phenylenediamine for 1,2-phenylenediamine.

$^1$H-NMR (300 MHz, DMSO-$d_6$) δ 9.60 (s, 1H), 8.51 (s, 1H), 8.21 (s, 1H), 7.95 (s, 1H), 7.81 (d, J=8.4 Hz, 2H), 7.38 (d, J=8.4 Hz, 2H), 7.03-7.15 (m, 2H), 5.19 (br s, 1H), 3.95-4.06 (m, 2H), 2.50 (s, 3H), 2.31 (s, 3H); ES-MS m/z 495.0 (MH)$^+$; HPLC RT (Method A) 2.39 min.

By using the method described above for Example 1, and by substituting the appropriate starting materials, Examples 16-57 found in the table below were similarly prepared. The 1,2-diamine reagents used to make these compounds were either purchased, prepared according to literature procedures, or prepared according to procedures detailed above for the corresponding Intermediates.

TABLE 2

| Ex. | R-group | LC-MS m/z (MH+), | LC-MS RT (min) [Method] |
|---|---|---|---|
| 16 | (thienoimidazole) | 473.0 | 2.08 [Method A] |
| 17 | (difluoromethylenedioxy-benzimidazole) | 546.9 | 2.45 [Method A] |
| 18 | (imidazopyridine) | 568.0 | 1.83 [Method A] |

TABLE 2-continued
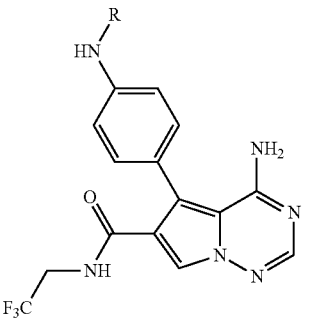
| Ex. | R-group | LC-MS m/z (MH+), | LC-MS RT (min) [Method] |
|---|---|---|---|
| 19 | 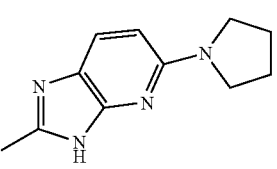 | 573.3 | 2.69 [Method A] |
| 20 | 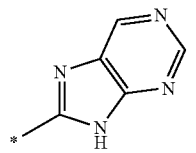 | 537.3 | 2.22 [Method A] |
| 21 | 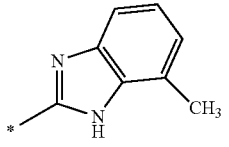 | 469.1 | 1.72 [Method A] |
| 22 | 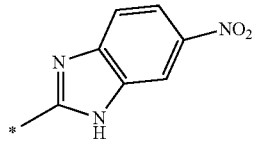 | 481.3 | 2.36 [Method A] |
| 23 | 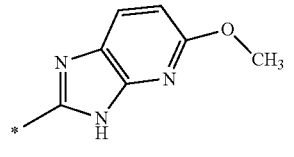 | 512.5 | 2.48 [Method A] |
| 24 | 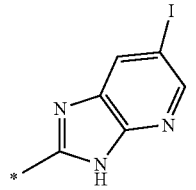 | 498.8 | 1.63 [Method A] |
| 25 |  | 594.2 | 2.34 [Method A] |

TABLE 2-continued

| Ex. | R-group | LC-MS m/z (MH+), | LC-MS RT (min) [Method] |
|---|---|---|---|
| 26 | 5-chloro-3H-imidazo[4,5-b]pyridin-2-yl | 502.1 | 2.33 [Method A] |
| 27 | 5-phenoxy-1H-benzimidazol-2-yl | 559.3 | 2.65 [Method B] |
| 28 | 5-methyl-3H-imidazo[4,5-b]pyridin-2-yl | 482.2 | 1.91 [Method A] |
| 29 | 5-(4-fluorophenoxy)-1H-benzimidazol-2-yl | 577.3 | 3.02 [Method A] |
| 30 | 6-methyl-3H-imidazo[4,5-b]pyridin-2-yl | 482.2 | 1.94 [Method A] |
| 31 | 5-(trifluoromethoxy)-1H-benzimidazol-2-yl | 551.2 | 2.57 [Method B] |
| 32 | 4-fluoro-5-phenoxy-1H-benzimidazol-2-yl | 577.2 | 2.78 [Method B] |

TABLE 2-continued

| Ex. | R-group | LC-MS m/z (MH+) | LC-MS RT (min) [Method] |
|---|---|---|---|
| 33 | 5-ethoxy-1H-benzimidazol-2-yl | 511.3 | 2.40 [Method B] |
| 34 | 4-fluoro-5-(4-methylphenoxy)-1H-benzimidazol-2-yl | 591.3 | 2.92 [Method B] |
| 35 | 4-fluoro-5-(4-fluorophenoxy)-1H-benzimidazol-2-yl | 595.2 | 3.86 [Method B] |
| 36 | 1-methyl-1H-benzimidazol-2-yl | 481.3 | 2.25 [Method B] |
| 37 | 4-fluoro-5-(pyrrolidin-1-yl)-1H-benzimidazol-2-yl | 554.3 | 2.40 [Method B] |
| 38 | 5-phenoxy-3H-imidazo[4,5-b]pyridin-2-yl | 560.3 | 3.01 [Method A] |

TABLE 2-continued

| Ex. | R-group | LC-MS m/z (MH+), | LC-MS RT (min) [Method] |
|---|---|---|---|
| 39 | benzimidazole-F-O-(2-F-phenyl) | 595.2 | 2.84 [Method B] |
| 40 | benzimidazole-F-O-(3-F-phenyl) | 595.2 | 2.91 [Method B] |
| 41 | benzimidazole-F-O-(2-CH₃-phenyl) | 591.2 | 2.92 [Method B] |
| 42 | benzimidazole-F-O-(3-CH₃-phenyl) | 591.2 | 2.89 [Method B] |
| 43 | imidazopyridine-NH-isopropyl | 542.2 | 2.19 [Method B] |
| 44 | N-methylbenzimidazole-C(O)CH₃ | 523.3 | 2.25 [Method A] |

TABLE 2-continued

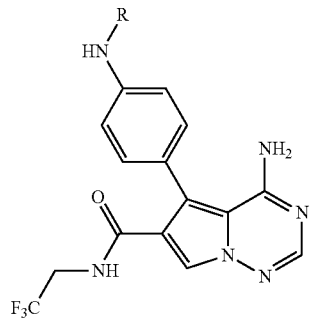

| Ex. | R-group | LC-MS m/z (MH+), | LC-MS RT (min) [Method] |
|---|---|---|---|
| 45 | H₃C-[6-methyl-9H-purin-2-yl] | 483.2 | 1.79 [Method A] |

Example 46

Preparation of 4-amino-5-{4-[(5-morpholin-4-yl-3H-imidazo[4,5-b]pyridin-2-yl)amino]phenyl}-N-(2,2,2-trifluoroethyl)pyrrolo[2,1-f][1,2,4]triazine-6-carboxamide

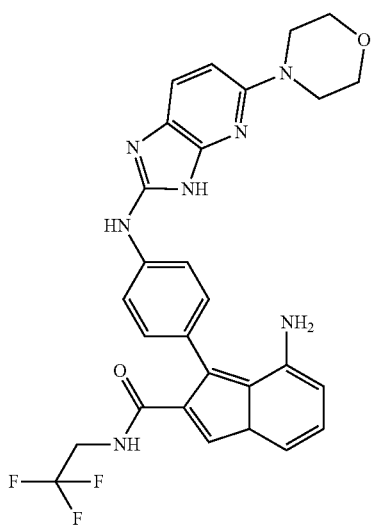

Step 1: Preparation of 6-morpholin-4-yl-3-nitropyridin-2-amine

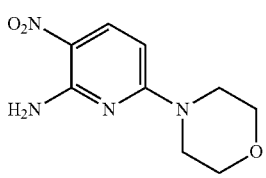

To a suspension of 6-chloro-3-nitropyridin-2-amine (150 mg, 0.864 mmol) in acetonitrile (10 mL) was added 0.3 mL of morpholine (0.3 mL, 3.46 mmol). The reaction mixture was heated (70° C.) for 5 h. The solvent was removed under vacuum and the residue was triturated with ether. The resulting yellow solid was filtered and dried to provide the desired product (100 mg, 51%). ES-MS m/z 224.91 (MH)⁺; HPLC RT (Method A) 2.33 min.

Step 2: Preparation of 6-morpholin-4-ylpyridine-2,3-diamine

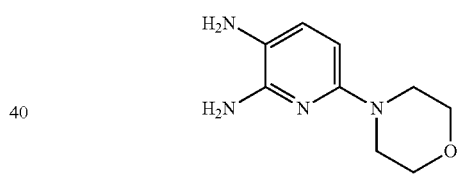

To a suspension of 6-morpholin-4-yl-3-nitropyridin-2-amine (200 mg, 0.89 mmol) in acetic acid (3.8 mL) was added iron powder (249 mg, 4.46 mmol). The mixture was stirred at rt for 16 h and then poured slowly into saturated aqueous sodium bicarbonate solution (100 mL). The mixture was extracted with ethyl acetate (3×50 mL), and then the combined organic extracts were washed with brine, dried over sodium sulfate, and concentrated under reduced pressure to provide the desired intermediate (150 mgs, 89%). The crude material was used directly without purification or analysis.

Step 3: Preparation of the Title Compound

To a solution of 4-amino-5-(4-aminophenyl)-N-(2,2,2-trifluoroethyl)pyrrolo[2,1-f][1,2,4]triazine-6-carboxamide (50 mg, 0.143 mmol) in DMF was added 1,1'-thiocarbonyldiimidazole (26.71 mg, 0.15 mmol) at rt, under an inert atmosphere. The mixture was stirred at it overnight. The following day, 1,2-phenylenediamine (29.11 mg, 0.15 mmol) was added and the mixture was stirred at rt for an additional 18 h. The following day, N,N'-diisopropylcarbodiimide (0.12 mL, 0.72 mmol) was added and the mixture was stirred at rt for an additional 18 h. The mixture was then concentrated under reduced pressure and the residue was submitted to silica gel column chromatography using 2 to 8% methanol/dichlo romethane as the eluent to afford the desired product (41 mg, 52%). ¹H-NMR (300 MHz, DMSO-d₆) δ 8.58 (t, J=7.2 Hz, 1H), 8.31 (s, 1H), 8.05 (s, 1H), 7.92 (d, J=7.2 Hz, 2H), 7.60 (br, 1H), 7.40 (d, J=7.2 Hz, 2H), 6.55-6.65 (m, 1H), 5.23 (br s, 1H), 4.02-4.12 (m, 2H), 3.75-3.85 (m, 4H), 3.35-4.45 (m, 4H); ES-MS m/z 553.30 (MH)⁺; HPLC RT (Method A) 2.14 min.

By using the method described above for Example 46 and by substituting the appropriate starting materials, examples 47-58 found in the table below were similarly prepared.

TABLE 3

| Ex. | R-group | LC-MS m/z (MH+), | LC-MS RT (min) [Method A] |
|---|---|---|---|
| 47 | | 537.3 | 2.51 [Method A] |
| 48 | | 565.3 | 2.94 [Method A] |
| 49 | | 588.3 | 3.07 [Method A] |
| 50 | | 594.2 | 3.04 [Method A] |
| 51 | | 579.4 | 2.96 [Method A] |
| 52 | | 539.3 | 2.47 [Method A] |

TABLE 3-continued
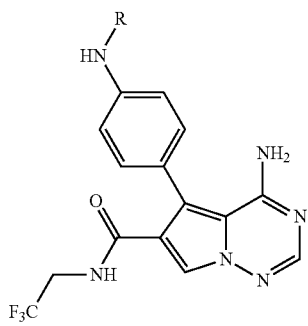
| Ex. | R-group | LC-MS m/z (MH+) | LC-MS RT (min) [Method A] |
|---|---|---|---|
| 53 | | 541.2 | 2.21 [Method A] |
| 54 | | 539.2 | 1.59 [Method A] |
| 55 | | 525.3 | 1.94 [Method A] |
| 56 | | 555.3 | 1.83 [Method A] |
| 57 | | 523.2 | 1.94 [Method A] |

TABLE 3-continued

| Ex. | R-group | LC-MS m/z (MH+), | LC-MS RT (min) [Method A] |
|---|---|---|---|
| 58 | | 573.0 | 2.40 [Method A] |

Example 59

Preparation of 4-amino-5-{4-[(5,7-difluoro-1H-benz-imidazol-2-yl)amino]-3-fluorophenyl}-N-(2,2,2-trifluoroethyl)pyrrolo[2,1-f][1,2,4]triazine-6-carboxamide

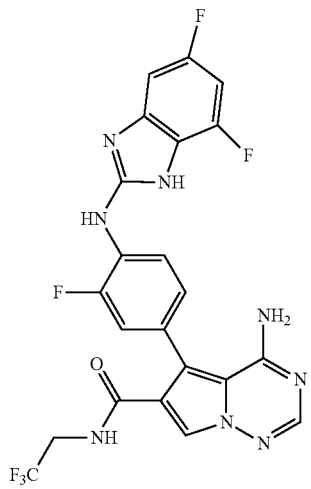

The procedure used for the preparation of Example 1 was used to prepare the title compound by substituting 3,5-difluoro-1,2-phenylenediamine for 1,2-phenylenediamine and ethyl 4-amino-5-(4-amino-3-fluorophenyl)pyrrolo[2,1-f][1,2,4]triazine-6-carboxylate (Intermediate E) for 4-amino-5-(4-aminophenyl)-N-(2,2,2-trifluoroethyl)pyrrolo[2,1-f][1,2,4]triazine-6-carboxamide (Intermediate C). $^1$H-NMR (300 MHz, DMSO-d$_6$) δ 11.05 (s, 1H), 9.58 (s, 1H), 8.58-8.65 (m, 2H), 8.21 (s, 1H), 7.91 (s, 1H), 7.28 (d, J=7.2 Hz, 1H), 7.21 (d, J=7.2 Hz, 1H), 7.10 (d, J=7.2 Hz, 1H), 6.86 (t, J=7.2 Hz, 1H), 5.35 (br s, 1H), 3.93-4.01 (m, 2H); ES-MS m/z 521.2 (MH)$^+$; HPLC RT (Method A) 2.45 min.

By using the method described above for Example 59, and by substituting the appropriate starting materials, Examples 60-70 found in the table below were similarly prepared. The 1,2-diamine reagents used to make these compounds were either purchased, prepared according to literature procedures, or prepared according to procedures detailed above for the corresponding Intermediates.

TABLE 4

| Ex. | R-group | LC-MS m/z (MH+) | LC-MS RT (min) [Method] |
|---|---|---|---|
| 60 | | 565.1 | 2.30 [Method A] |

TABLE 4-continued

[Structure: R-HN-phenyl(F)-pyrrolo[2,1-f][1,2,4]triazine with NH2 and C(O)NH-CH2-CF3]

| Ex. | R-group | LC-MS m/z (MH+) | LC-MS RT (min) [Method] |
|---|---|---|---|
| 61 | 5-chloro-benzimidazol-2-yl | 519.2 | 2.48 [Method A] |
| 62 | 5-methyl-imidazo[4,5-b]pyridin-2-yl | 500.3 | 1.97 [Method A] |
| 63 | 5-morpholino-imidazo[4,5-b]pyridin-2-yl | 571.3 | 2.20 [Method A] |
| 64 | 5-pyrrolidinyl-imidazo[4,5-b]pyridin-2-yl | 555.4 | 2.34 [Method A] |
| 65 | imidazo[4,5-b]pyridin-2-yl | 486.2 | 1.89 [Method A] |
| 66 | 5-chloro-6-fluoro-benzimidazol-2-yl | 537.3 | 2.93 [Method A] |
| 67 | thieno-imidazol-2-yl | 491.4 | 2.01 [Method A] |
| 68 | 5-benzoyl-benzimidazol-2-yl | 589.3 | 3.02 [Method B] |
| 69 | imidazo[4,5-c]pyridin-2-yl | 486.2 | 1.85 [Method A] |
| 70 | 7-methyl-benzimidazol-2-yl | 499.24 | 2.34 [Method A] |

Example 71

Preparation of 4-amino-5-{4-[(5,7-difluoro-1H-benzimidazol-2-yl)amino]phenyl}pyrrolo[2,1-f][1,2,4]triazine-6-carboxylic acid To a mixture of ethyl 4-amino-5-{4-[(5,7-difluoro-1H-benzimidazol-2-yl)amino]phenyl}pyrrolo[2,1-f][1,2,4]triazine-6-carboxylate (5.85 g, 13.0 mmol) in THF (300 mL) and methanol (100 mL) was added 1N aqueous sodium hydroxide solution (130 mL, 130 mmol). The reaction was stirred at rt overnight and then the solution was concentrated under reduced pressure. The residue was diluted in water (500 mL) and then the mixture was adjusted to pH 3 using concentrated hydrochloric acid. The resulting precipitate was collected by filtration and dried to yield the desired product (5.60 g, 100%) containing some trace impurities. $^1$H-NMR (300 MHz, DMSO-$d_6$) δ 10.17 (s, 1H), 8.17-8.38 (br s, 1H) 8.14 (s, 1H), 7.97 (s, 1 H), 7.77 (d, J=8.0 Hz, 2H), 7.38 (d, J=8.0 Hz, 2H), 7.05 (d, J=8.1 Hz, 1H), 6.93 (dd, J=10.2, 10.2 Hz, 1H) 5.22-5.44 (br s, 1H); ES-MS m/z 422.1 (MH)$^+$; HPLC RT (Method B) 2.13 min.

Example 72

Preparation of 4-amino-N-(tert-butyl)-5-{4-[(5,7-difluoro-1H-benzimidazol-2-yl)amino]phenyl}pyrrolo[2,1-f][1,2,4]triazine-6-carboxamide

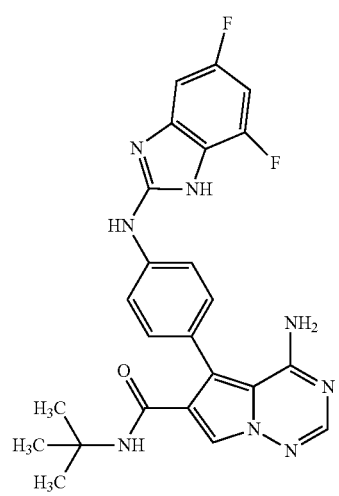

To a suspension of 4-amino-5-{4-[(5,7-difluoro-1H-benzimidazol-2-yl)amino]phenyl}pyrrolo[2,1-f][1,2,4]triazine-6-carboxylic acid (75.0 mg, 0.178 mmol) in DMF (3 mL) was added tert-butylamine (0.021 ml, 0.196 mmol), benzotriazolyloxytris(dimethylamino)phosphonium PF$_6$ (86.6 mg, 0.196 mmol), and 4-methylmorpholine (0.039 ml, 0.356 mmol). The reaction was stirred for 3 hr at rt and then purified directly by HPLC using 25-85% acetonitrile in water to afford the desired product (75.3 mg, 89%). $^1$H-NMR (300 MHz, DMSO-$d_6$) δ 9.80 (s, 1H), 8.02 (s, 1H), 7.80-8.02 (m, 3H), 7.38 (dd, J=6.7, 2.0 Hz, 2H), 7.00 (dd, J=8.9, 2.2 Hz, 1H), 6.85 (ddd, J=10.7, 10.7, 2.4 Hz, 1H), 6.54 (s, 1H), 4.96-5.21 (br s, 1H), 1.16 (s, 9H); ES-MS m/z 477.1 (MH)$^+$; HPLC RT (Method B) 2.54 min.

By using the method described above for Example 72, and by substituting the appropriate starting materials, Examples 73-100 found in the table below were similarly prepared.

TABLE 5

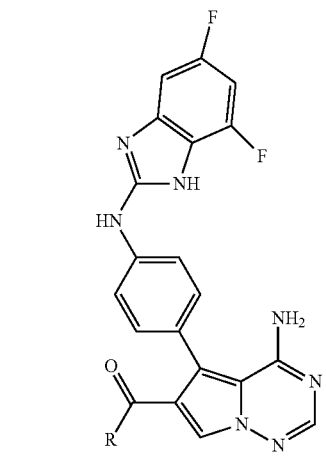

| Ex. | R-group | LC-MS m/z (MH+) | LC-MS RT (min) [Method] |
|---|---|---|---|
| 73 | H₃C—CH₂—NH—* | 449.1 | 2.21 [Method B] |
| 74 | (H₃C)₂N—* | 449.1 | 2.08 [Method A] |
| 75 | H₃C—O—CH₂CH₂—NH—* | 479.1 | 2.15 [Method A] |
| 76 | morpholin-4-yl—* | 491.2 | 2.15 [Method B] |
| 77 | cyclobutyl-NH—* | 475.2 | 2.97 [Method D] |
| 78 | cyclohexyl-NH—* | 503.2 | 3.03 [Method D] |
| 79 | (H₃C)₂CHCH₂—NH—* | 491.2 | 3.00 [Method D] |
| 80 | cyclopropyl-CH₂—NH—* | 475.2 | 2.86 [Method D] |
| 81 | H₂N-CO-(piperidin-4-yl)-N—* | 532.2 | 2.57 [Method D] |

TABLE 5-continued
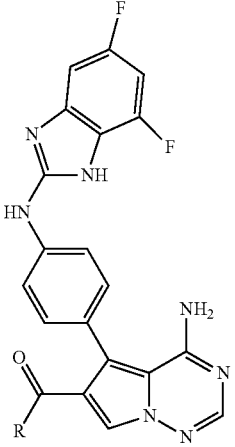
| Ex. | R-group | LC-MS m/z (MH+), | LC-MS RT (min) [Method] |
|---|---|---|---|
| 82 | 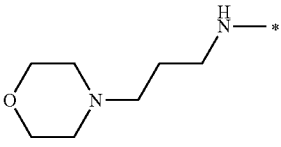 | 532.2 | 2.53 [Method D] |
| 83 | 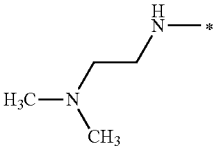 | 548.2 | 2.52 [Method D] |
| 84 | 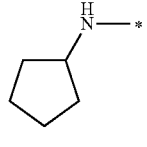 | 492.2 | 2.49 [Method D] |
| 85 | 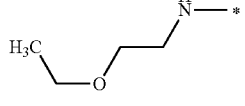 | 489.2 | 2.93 [Method D] |
| 86 | 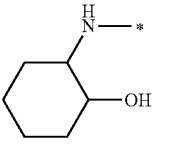 | 493.2 | 2.79 [Method D] |
| 87 | 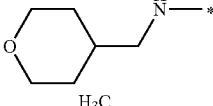 | 519.2 | 2.83 [Method D] |
| 88 | 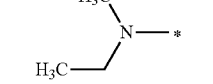 | 519.2 | 2.74 [Method D] |
| 89 | 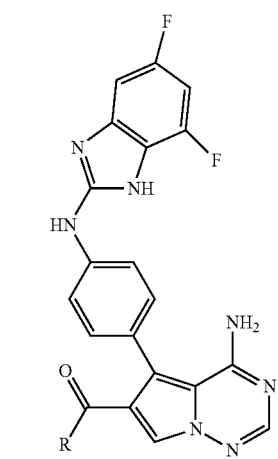 | 463.2 | 2.74 [Method D] |
TABLE 5-continued
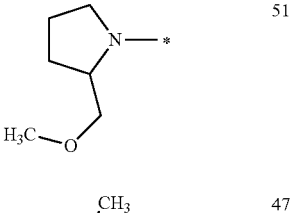
| Ex. | R-group | LC-MS m/z (MH+), | LC-MS RT (min) [Method] |
|---|---|---|---|
| 90 | 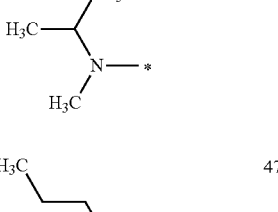 | 491.2 | 2.89 [Method D] |
| 91 | 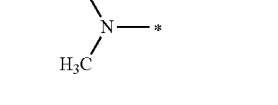 | 519.2 | 2.83 [Method D] |
| 92 | 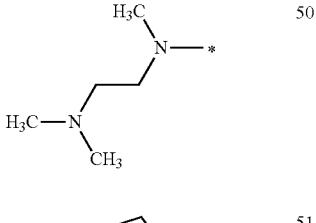 | 477.2 | 2.8 [Method D] |
| 93 | 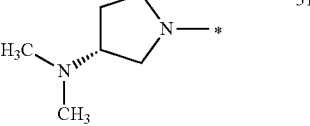 | 477.2 | 2.81 [Method D] |
| 94 | | 506.2 | 2.5 [Method D] |
| 95 | | 518.2 | 2.48 [Method D] |

TABLE 5-continued

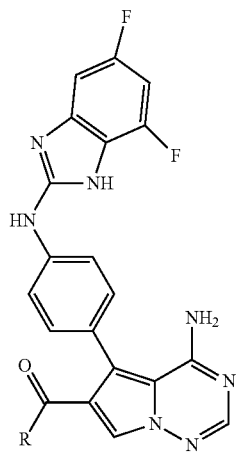

| Ex. | R-group | LC-MS m/z (MH+) | LC-MS RT (min) [Method] |
|---|---|---|---|
| 96 | pyrrolidinyl | 475.2 | 2.76 [Method D] |
| 97 | N,N-diethylamino | 491.2 | 2.89 [Method D] |
| 98 | 4-methylpiperazinyl | 504.2 | 2.49 [Method D] |
| 99 | 3-oxopiperazinyl | 504.2 | 2.55 [Method D] |
| 100 | N-methyl-N-((tetrahydropyran-4-yl)methyl)amino | 533.2 | 2.75 [Method D] |

Example 101

4-amino-5-{4-[(7-fluoro-6-phenoxy-1H-benzimidazol-2-yl)amino]phenyl}pyrrolo[2,1-f][1,2,4]triazine-6-carboxylic acid

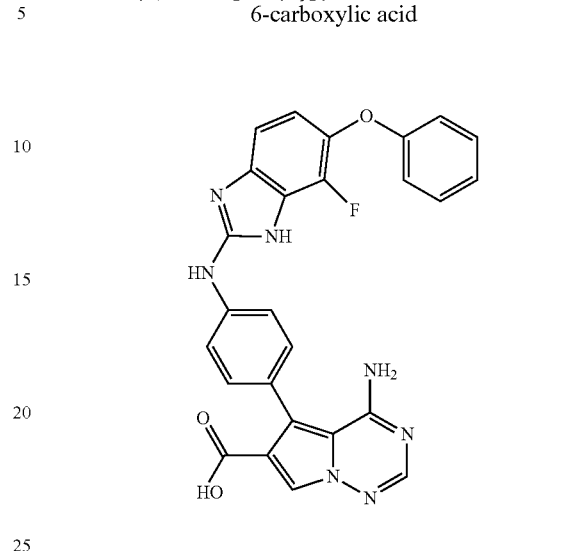

The procedure used for the preparation of Example 71 was used to prepare the title compound by substituting ethyl 4-amino-5-{4-[(7-fluoro-6-phenoxy-1H-benzimidazol-2-yl)amino]phenyl}pyrrolo[2,1-f][1,2,4]triazine-6-carboxylate (Intermediate G) for ethyl 4-amino-5-{4-[(5,7-difluoro-1H-benzimidazol-2-yl)amino]phenyl}pyrrolo[2,1-f][1,2,4]triazine-6-carboxylate (Intermediate F). $^1$H-NMR (300 MHz, DMSO-$d_6$) δ 8.06 (s, 1H), 7.95-8.06 (br s, 1H), 7.91 (s, 1H), 7.81 (d, J=8.4 Hz, 2H), 7.28-7.40 (m, 4H), 7.12 (d, J=8.5 Hz, 1H), 7.02 (dd, J=7.3, 7.3 Hz, 1H), 6.89 (d, J=8.1 Hz, 1H), 6.82 (dd, J=7.8, 7.8 Hz, 1H), 5.02-5.19 (br s, 1H); ES-MS m/z 496.3 (MH)$^+$; HPLC RT (Method A) 2.94 min.

Example 102

Preparation of 4-amino-5-{4-[(7-fluoro-6-phenoxy-1H-benzimidazol-2-yl)amino]phenyl}-N-methylpyrrolo[2,1-f][1,2,4]triazine-6-carboxamide

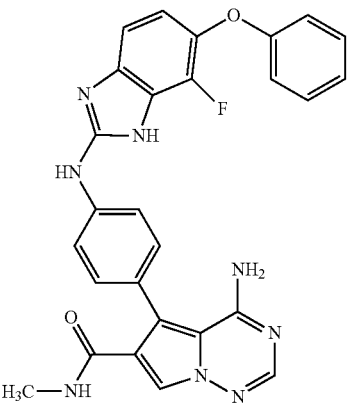

The procedure used for the preparation of Example 72 was used to prepare the title compound by substituting 4-amino-5-{4-[(7-fluoro-6-phenoxy-1H-benzimidazol-2-yl)amino]phenyl}pyrrolo[2,1-f][1,2,4]triazine-6-carboxylic acid (Example 101) for 4-amino-5-{4-[(5,7-difluoro-1H- benzimidazol-2-yl)amino]phenyl}pyrrolo[2,1-f][1,2,4]triazine-6-carboxylic acid (Example 71). $^1$H-NMR (300 MHz, DMSO-d$_6$) δ 9.98 (s, 1H), 8.08 (s, 1H), 7.73-7.95 (m, 4H), 7.27-7.39 (m, 4H), 7.15 (d, J=8.5 Hz, 1H), 7.03 (dd, J=7.8, 7.8 Hz, 1H), 6.83-6.93 (m, 3H), 5.11-5.28 (br s, 1H), 2.63 (d, J=4.5 Hz, 3H); ES-MS m/z 509.1 (MH)$^+$; HPLC RT (Method B) 2.55 min.

By using the method described above for Example 102, and by substituting the appropriate starting materials, Examples 103-114 found in the table below were similarly prepared.

TABLE 6

| Ex. | R-group | LC-MS m/z (MH+], | LC-MS RT (min) |
|---|---|---|---|
| 103 | | 537.3 | 2.62 [Method A] |
| 104 | | 537.3 | 2.60 [Method A] |
| 105 | | 535.1 | 2.67 [Method B] |
| 106 | | 537.2 | 2.66 [Method B] |
| 107 | | 563.3 | 2.79 [Method B] |

TABLE 6-continued

| Ex. | R-group | LC-MS m/z (MH+], | LC-MS RT (min) |
|---|---|---|---|
| 108 | | 565.3 | 2.60 [Method B] |
| 109 | | 523.3 | 2.51 [Method A] |
| 110 | | 553.1 | 2.96 [Method A] |
| 111 | | 551.3 | 2.73 [Method A] |
| 112 | | 563.3 | 2.76 [Method A] |
| 113 | | 549.2 | 2.93 [Method A] |
| 114 | | 549.2 | 2.82 [Method B] |

Example 115

Preparation of 4-amino-5-(4-{[5-(4-methylphenyl)-3H-imidazo[4,5-b]pyridin-2-yl]amino}phenyl)-N-(2,2,2-trifluoroethyl)pyrrolo[2,1-f][1,2,4]triazine-6-carboxamide

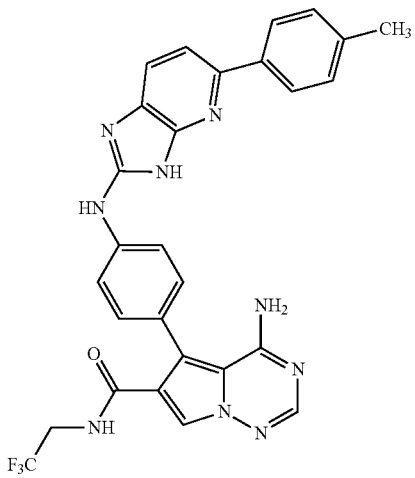

To a mixture of 4-amino-5-{4-[(5-chloro-3H-imidazo[4,5-b]pyridin-2-yl)amino]phenyl}-N-(2,2,2-trifluoroethyl)pyrrolo[2,1-f][1,2,4]triazine-6-carboxamide (50 mg, 0.1 mmol), p-tolylboronic acid (27 mg, 0.2 mmol), potassium carbonate (82 mg, 0.6 mmol), in DMF was added 1,1'-bis(diphenylphosphino)ferrocinepalladium (II) chloride (7.3 mg, 0.01 mmol). The mixture was then degassed using nitrogen for 10 min, and then heated (150° C.) in a microwave for 15 min. After cooling to room temperature, the mixture was diluted with methanol and concentrated under reduced pressure. The residue purified by silica gel chromatography using a 1 to 8% methanol/dichloromethane as the eluant to afford the desired product (5.9 mg, 11%). $^1$H-NMR (300 MHz, CD$_3$OD) δ 7.86 (s, 1H), 7.81-7.87 (m, 4H), 7.73-7.79 (m, 2H), 7.63-7.69 (m, 1H), 7.53 (s, 1H), 7.40-7.49 (m, 2H), 7.22-7.28 (m, 2H), 3.92-3.99 (m, 2H), 2.38 (s, 3H); ES-MS m/z 558.3 (MH)$^+$; HPLC RT (Method A) 2.64 min.

Example 116

Preparation of 4-amino-5-[4-({5-[3-(methoxymethyl)phenyl]-3H-imidazo[4,5-b]pyridin-2-yl}amino)phenyl]-N-(2,2,2-trifluoroethyl)pyrrolo[2,1-f][1,2,4]triazine-6-carboxamide

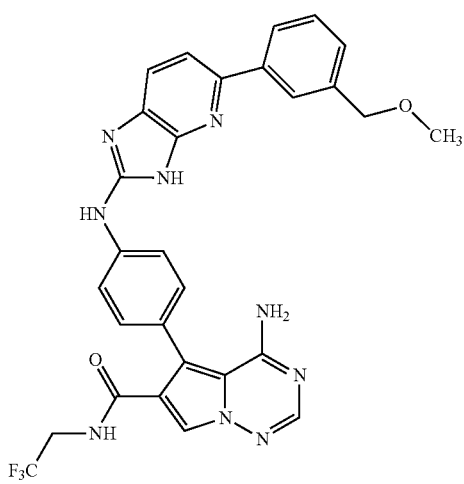

The procedure used for the preparation of Example 115 was used to prepare the title compound by substituting 3-methoxyphenylboronic acid for p-tolylboronic acid. $^1$H-NMR (300 MHz, CD$_3$OD) δ 8.05 (s, 1H), 7.97 (s, 1H), 7.89-7.95 (m, 1H), 7.86 (s, 1H), 7.73-7.79 (m, 2H), 7.41-7.48 (m, 2H), 7.65-7.71 (m, 1H), 7.55-7.62 (m, 1H), 7.39-7.47 (m, 3H), 7.34 (s, 1H), 4.54 (s, 2H), 3.92-3.99 (m, 2H), 3.41 (s, 3H); ES-MS m/z 588.0 (MH)$^+$; HPLC RT (Method A) 2.40 min.

Example 117

Preparation of 4-amino-N-(tert-butyl)-5-{4-[(6-chloro-3H-imidazo[4,5-b]pyridin-2-yl)amino]-3-fluorophenyl}pyrrolo[2,1-f][1,2,4]triazine-6-carboxamide

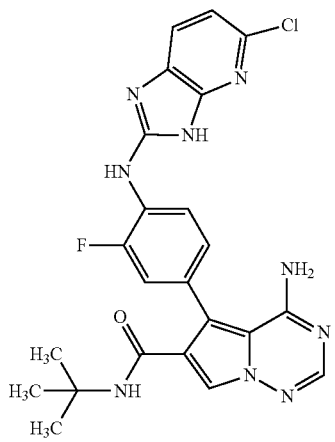

To a solution of 4-amino-5-(4-amino-3-fluorophenyl)-N-tert-butylpyrrolo[2,1-f][1,2,4]triazine-6-carboxamide (100.0 mg, 0.29 mmol) in DMF (3.4 mL) was added 1,1'-thiocarbonyldiimidazole (54.7 mg, 0.31 mmol). The mixture was stirred at rt overnight. 2,3-Diamino-5-chloropyridine (44.0 mg, 0.31 mmol) was added and the resultant mixture was stirred overnight. Finally, N,N'-diisopropylcarbodiimide (184.3 mg, 1.46 mmol) was added and the solution was stirred at it overnight. The crude reaction mixture was purified via HPLC using a gradient of 20-70% acetonitrile in water to yield the desired product (29.9 mg, 21%). $^1$H NMR (DMSO-d$_5$) δ 8.09 (s, 1H), 7.92 (s, 1H), 7.78 (br s, 1H), 7.35 (dd, J=12.3, 1.9 Hz, 1H), 7.26 (d, J=8.6, 1H), 1.22 (s, 9H); ES-MS m/z 494.1 (MH)$^+$; HPLC RT (Method B) 2.55 min.

Example 118

Preparation of 4-amino-N-(tert-butyl)-5-{4-[(2,2-difluoro-5H-[1,3]dioxolo[4,5-f]benzimidazol-6-yl)amino]-3-fluorophenyl}pyrrolo[2,1-f][1,2,4]triazine-6-carboxamide

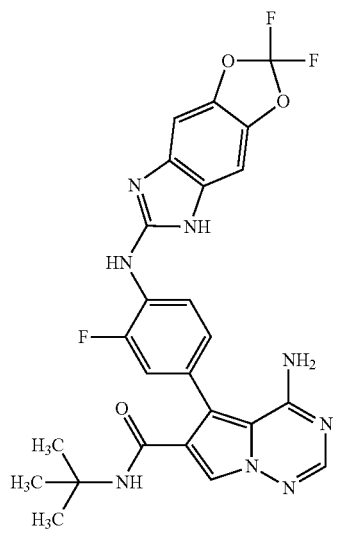

The procedure used for the preparation of Example 117 was used to prepare the title compound by substituting 2,3-diamino-5-chloropyridine for 5,6-diamino-2,2-difluoro-1,3-benzodioxole. $^1$H NMR (DMSO-$d_6$) δ 10.91 (s, 1H), 9.52 (d, J=2.2 Hz, 1H), 8.68 (t, J=8.7 Hz, 1H), 8.06 (s, 1H), 7.90 (s, 1H), 7.42 (d, J=8.5 Hz, 2H), 7.31 (dd, J=12.4, 1.8 Hz, 1H), 7.21 (dd, J=8.2, 1.4 Hz, 1H), 6.89 (s, 1H), 1.20 (s, 9H); ES-MS m/z 539.1 (MH)$^+$; HPLC RT (Method B) 2.73 min.

Example 119

4-amino-5-(4-{([5-(trifluoromethyl)-3H-imidazo[4,5-b]pyridin-2-yl]amino}phenyl)pyrrolo[2,1-f][1,2,4]triazine-6-carboxylic acid

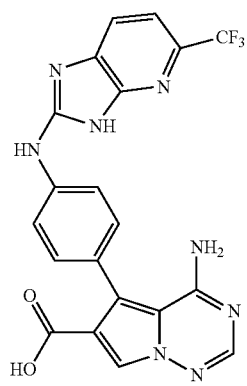

The procedure used for the preparation of Example 71 was used to prepare the title compound by substituting ethyl 4-amino-5-(4-{[5-(trifluoromethyl)-3H-imidazo[4,5-b]pyridin-2-yl]amino}phenyl)pyrrolo[2,1-f][1,2,4]triazine-6-carboxylate (Intermediate H) for ethyl 4-amino-5-{4-[(5,7-difluoro-1H-benzimidazol-2-yl)amino]phenyl}pyrrolo[2,1-f][1,2,4]triazine-6-carboxylate (Intermediate F). $^1$H-NMR (300 MHz, DMSO-$d_6$) δ 8.10 (s, 1H), 7.94 (s, 1H), 7.82-7.89 (m, 2H), 7.73-7.79 (m, 1H), 7.65-7.71 (m, 2H), 7.45-7.51 (m, 1H), 7.34-7.41 (m, 2H); ES-MS m/z 455.2 (MH)$^+$; HPLC RT (Method A) 2.40 min.

Example 120

Preparation of 4-amino-N-(2,2,2-trifluoroethyl)-5-(4-{[5-(trifluoromethyl)-3H-imidazo[4,5-b]pyridin-2-yl]amino}phenyl)pyrrolo[2,1-f][1,2,4]triazine-6-carboxamide

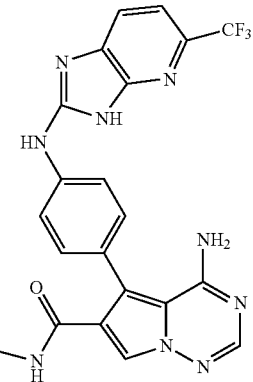

The procedure used for the preparation of Example 72 was used to prepare the title compound by substituting 4-amino-5-(4-{[5-(trifluoromethyl)-3H-imidazo[4,5-b]pyridin-2-yl]amino}phenyl)pyrrolo[2,1-f][1,2,4]triazine-6-carboxylic acid (Example 119) for 4-amino-5-{4-[(5,7-difluoro-1H-benzimidazol-2-yl)amino]phenyl}pyrrolo[2,1-f][1,2,4]triazine-6-carboxylic acid (Example 71). $^1$H-NMR (300 MHz, CD$_3$OD) δ 8.05 (s, 1H), 7.85 (s, 1H), 7.77-7.85 (m, 2H), 7.55-7.69 (m, 2H), 7.42-7.49 (m, 3H), 7.22-7.31 (m, 1H), 3.92-3.99 (m, 2H); ES-MS m/z 536.2 (MH)$^+$; HPLC RT (Method A) 2.73 min.

Example 121

Preparation of ethyl 4-amino-5-[4-(1H-benzimidazol-2-ylamino)phenyl]pyrrolo[2,1-f][1,2,4]triazine-6-carboxylate

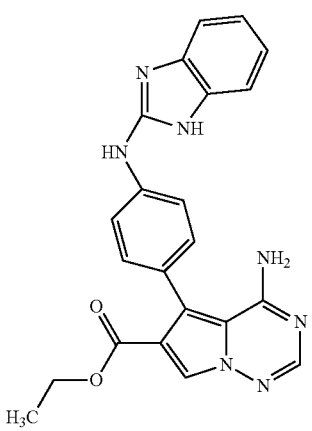

A solution of ethyl 4-amino-5-(4-aminophenyl)pyrrolo[2,1-f][1,2,4]triazine-6-carboxylate (50.0 mg, 0.17 mmol) and 2-chlorobenzimidazole (30.2 mg, 0.17 mmol) in n-butanol (5 mL) and DMF (1 mL) were heated (90° C.) overnight in the presence of a trace amount of 4 M hydrogen chloride in dioxane. After cooling, the solution was concentrated under reduced pressure and the residue was purified by HPLC to afford the desired product (14.2 mg, 19%). ¹H-NMR (300 MHz, DMSO-d₆) δ 8.09 (s, 1H), 8.05 (br s, 1H), 7.89 (s, 1H), 7.79-7.85 (m, 2H), 7.24-7.34 (m, 4H), 6.89-6.99 (m, 2H), 5.14 (br, s, 1H), 4.06 (q, J=7.1 Hz, 2H), 1.09 (t, J=7.1 Hz, 3H); ES-MS m/z 414.3 (MH)⁺; HPLC RT (Method A) 2.57 min.

Example 122

Preparation of ethyl 4-amino-5-{4-[(6-methoxy-1H-benzimidazol-2-yl)amino]phenyl}pyrrolo[2,1-f][1,2,4]triazine-6-carboxylate

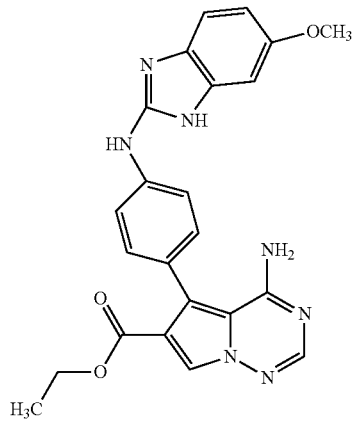

The procedure used for the preparation of Example 121 was used to prepare the title compound by substituting 2-chloro-4-methoxybenzimidazole for 2-chlorobenzimidazole. ¹H-NMR (300 MHz, DMSO-d₆) δ 8.09 (s, 1H), 8.05 (br s, 1H), 7.89 (s, 1. H), 7.79 (d, J=8.5 Hz, 2H), 7.28 (d, J=8.5 Hz, 2H), 7.16 (br d 1H), 6.87 (br s, 1H), 6.54-6.60 (m, 1H), 5.16 (br, s, 1H), 4.06 (q, J=7.1 Hz, 2H), 3.71 (s, 3H), 1.09 (t, J=7.1 Hz, 3H); ES-MS m/z 444.3 (MH)⁺; HPLC RT (Method A) 2.63 min.

Further examples, which can be prepared by using the methods described above, are as follows:

Example 123

Preparation of 5-{4-[(6-acetyl-1H-benzimidazol-2-yl)amino]phenyl}-4-amino-N-(2,2,2-trifluoroethyl)pyrrolo[2,1-f][1,2,4]triazine-6-carboxamide

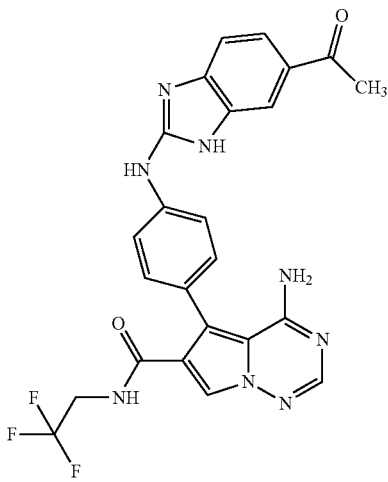

The procedure used for the preparation of Example 1 is used to prepare the title compound by substituting 1-(3,4-diaminophenyl)ethanone for 1,2-phenylenediamine.

Example 124

Preparation of 4-amino-5-[4-({6-[(methylamino)carbonyl]-1H-benzimidazol-2-yl}amino)phenyl]-N-(2,2,2-trifluoroethyl)pyrrolo[2,1-f][1,2,4]triazine-6-carboxamide

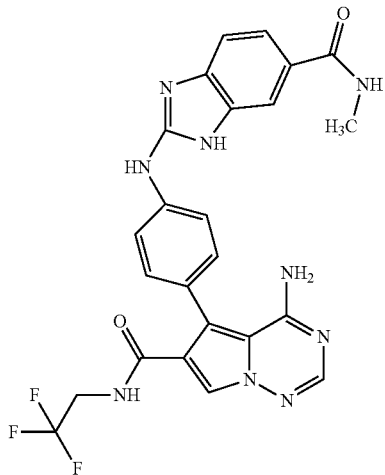

The procedure used for the preparation of Example 1 is used to prepare the title compound by substituting 3,4-diamino-N-methylbenzamide for 1,2-phenylenediamine.

Example 125

Preparation of 4-amino-5-[4-({6-[(diethylamino)sulfonyl]-1H-benzimidazol-2-yl}amino)phenyl]-N-(2,2,2-trifluoroethyl)pyrrolo[2,1-f][1,2,4]triazine-6-carboxamide

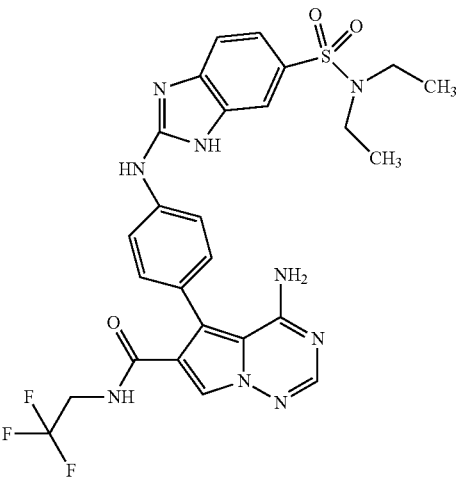

The procedure used for the preparation of Example 1 is used to prepare the title compound by substituting 3,4-diamino-N,N-diethylbenzenesulfonamide for 1,2-phenylenediamine.

Example 126

Preparation of 2-{[4-(4-amino-6-{[(2,2,2-trifluoroethyl)amino]carbonyl}pyrrolo[2,1-f][1,2,4]triazin-5-yl)phenyl]amino}-1H-benzimidazole-6-carboxylic acid

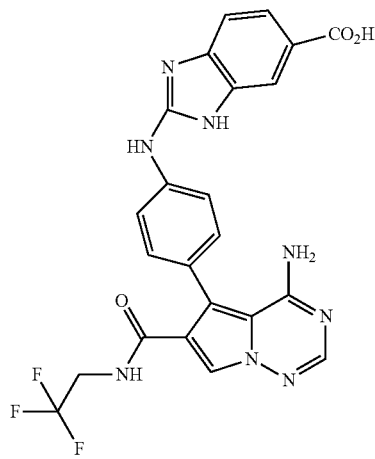

The procedure used for the preparation of Example 1 is used to prepare the title compound by substituting 3,4-diaminobenzoic acid for 1,2-phenylenediamine.

Example 127

Preparation of 4-amino-5-{4-[(6-morpholin-4-yl-1H-benzimidazol-2-yl)amino]phenyl}-N-(2,2,2-trifluoroethyl)pyrrolo[2,1-f][1,2,4]triazine-6-carboxamide

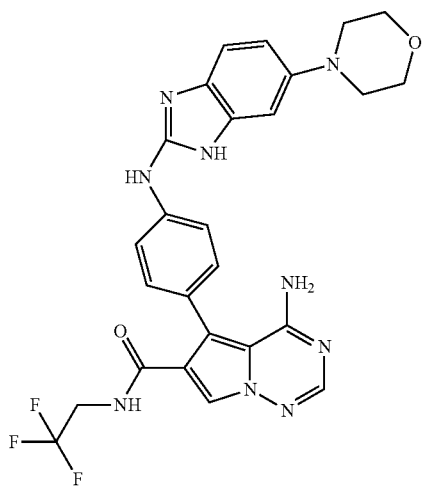

The procedure used for the preparation of Example 1 is used to prepare the title compound by substituting 4-morpholin-4-ylbenzene-1,2-diamine for 1,2-phenylenediamine.

Example 128

Preparation of 4-amino-5-(4-{[(6-(4-methylpiperazin-1-yl)-1H-benzimidazol-2-yl]amino}phenyl)-N-(2,2,2-trifluoroethyl)pyrrolo[2,1-f][1,2,4]triazine-6-carboxamide

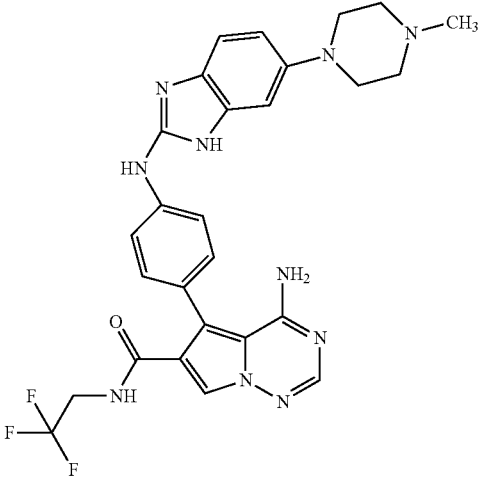

The procedure used for the preparation of Example 1 is used to prepare the title compound by substituting 4-(4-methylpiperazin-1-yl)benzene-1,2-diamine for 1,2-phenylenediamine.

Example 129

Preparation of 4-amino-5-(4-{[(6-({2-[(methylamino)carbonyl]pyridin-4-yl}oxy)-1H-benzimidazol-2-yl]amino}phenyl)-N-(2,2,2-trifluoroethyl)pyrrolo[2,1-f][1,2,4]triazine-6-carboxamide

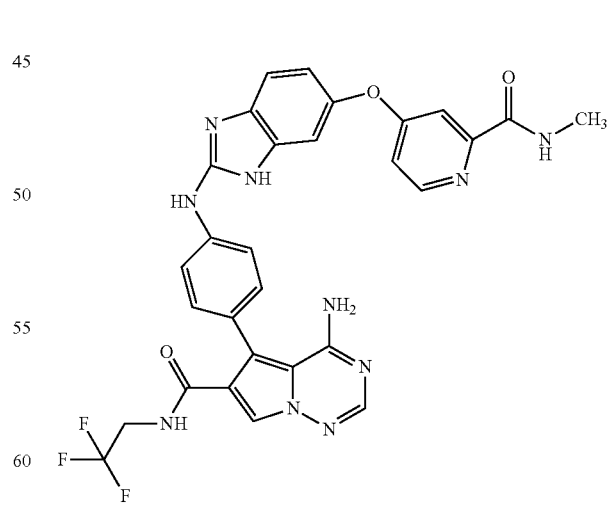

The procedure used for the preparation of Example 1 is used to prepare the title compound by substituting 4-(3,4-diaminophenoxy)-N-methylpyridine-2-carboxamide for 1,2-phenylenediamine.

Example 130

Preparation of 4-amino-5-{4-[(5,6-dimethoxy-1H-benzimidazol-2-yl)amino]phenyl}-N-(2,2,2-trifluoroethyl)pyrrolo[2,1-f][1,2,4]triazine-6-carboxamide

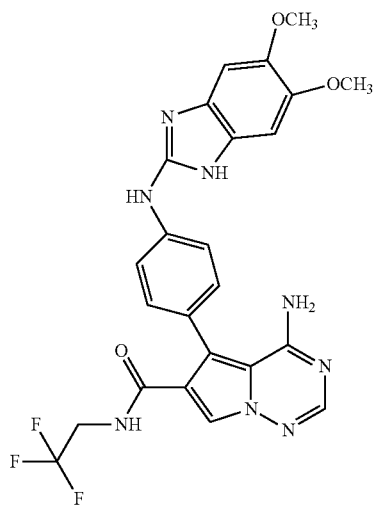

The procedure used for the preparation of Example 1 is used to prepare the title compound by substituting 4,5-dimethoxybenzene-1,2-diamine for 1,2-phenylenediamine.

Example 131

Preparation of 4-amino-5-{4-[(5,7-dimethyl-1H-benzimidazol-2-yl)amino]phenyl}-N-(2,2,2-trifluoroethyl)pyrrolo[2,1-f][1,2,4]triazine-6-carboxamide

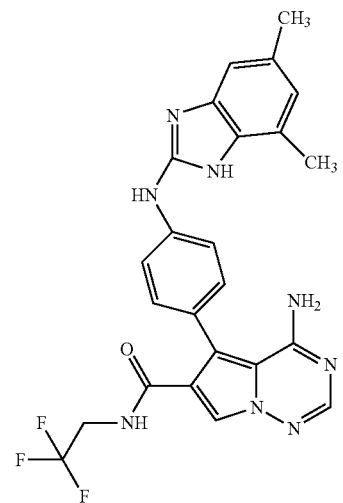

The procedure used for the preparation of Example 1 is used to prepare the title compound by substituting 3,5-dimethylbenzene-1,2-diamine for 1,2-phenylenediamine.

Example 132

Preparation of 4-amino-5-{4-[(7-methoxy-1H-benzimidazol-2-yl)amino]phenyl}-N-(2,2,2-trifluoroethyl)pyrrolo[2,1-f][1,2,4]triazine-6-carboxamide

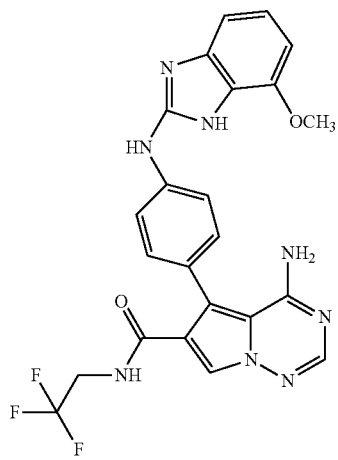

The procedure used for the preparation of Example 1 is used to prepare the title compound by substituting 3-methoxy-1,2-phenylenediamine for 1,2-phenylenediamine.

Example 133

Preparation of methyl 2-{([4-(4-amino-6-{[(2,2,2-trifluoroethyl)amino]carbonyl}pyrrolo[2,1-f][1,2,4]triazin-5-yl)phenyl]amino}-1H-benzimidazole-7-carboxylate

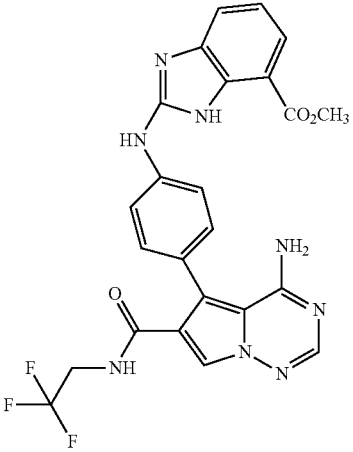

The procedure used for the preparation of Example 1 is used to prepare the title compound by substituting methyl 2,3-diaminobenzoate for 1,2-phenylenediamine.

Example 134

Preparation of 4-amino-5-[4-(5H-[1,3]dioxolo[4,5-f]benzimidazol-6-ylamino)phenyl]-N-(2,2,2-trifluoroethyl)pyrrolo[2,1-f][1,2,4]triazine-6-carboxamide

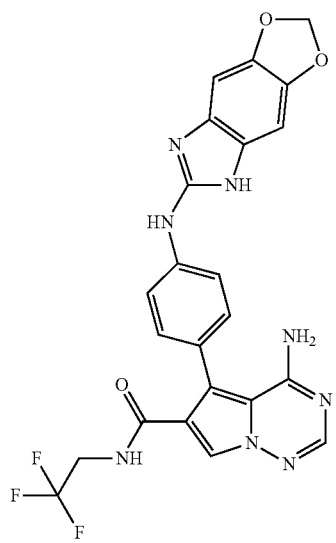

The procedure used for the preparation of Example 1 is used to prepare the title compound by substituting 1,3-benzodioxole-5,6-diamine for 1,2-phenylenediamine.

Example 135

Preparation of 4-amino-5-[4-(6,7-dihydro-1H-[1,4]dioxino[2,3-f]benzimidazol-2-ylamino)phenyl]-N-(2,2,2-trifluoroethyl)pyrrolo[2,1-f][1,2,4]triazine-6-carboxamide

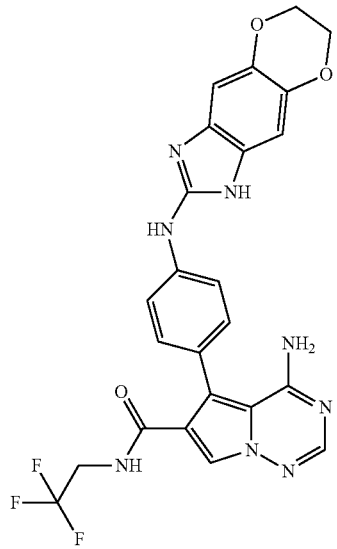

The procedure used for the preparation of Example 1 is used to prepare the title compound by substituting 2,3-dihydro-1,4-benzodioxine-6,7-diamine for 1,2-phenylenediamine.

Example 136

Preparation of 4-amino-5-[4-(1H-benzimidazol-2-ylamino)-3-fluorophenyl]-N-(tert-butyl)pyrrolo[2,1-f][1,2,4]triazine-6-carboxamide

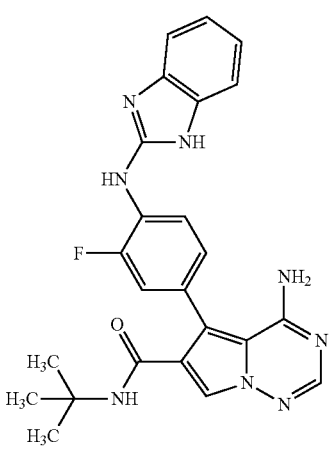

The procedure used for the preparation of Example 1 is used to prepare the title compound by substituting Intermediate I for Intermediate C.

Example 137

Preparation of ethyl 4-amino-5-[4-(1H-benzimidazol-2-ylamino)-3-fluorophenyl]pyrrolo[2,1-f][1,2,4]triazine-6-carboxylate

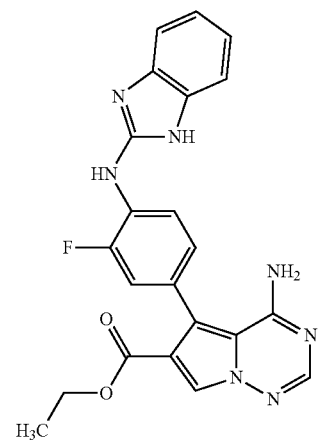

The procedure used for the preparation of Example 1 is used to prepare the title compound by substituting Intermediate D for Intermediate C.

Example 138

Preparation of 4-amino-5-[4-(1H-benzimidazol-2-ylamino)-3-fluorophenyl]-N-(2,2,2-trifluoroethyl)pyrrolo[2,1-f][1,2,4]triazine-6-carboxamide

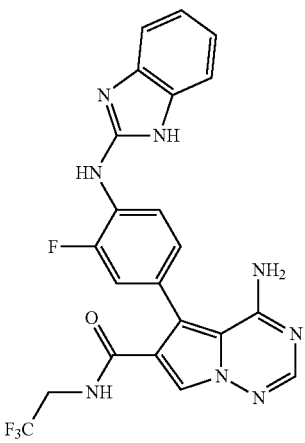

The procedure used for the preparation of Example 1 is used to prepare the title compound by substituting Intermediate E for Intermediate C.

A. Physiological Activity

The utility of the compounds of the present invention can be illustrated, for example, by their activity in vitro in the Aurora 1 and 2 biochemical and Aurora 1 autophosphorylation assays described before. The link between Aurora Kinase inhibition and activity in human tumor xenograft models in mice has been established (Harrington et al. *Nature Medicine* 2004, 10 (3), 262). Furthermore, it has been very well established in the art that activity in human tumor xenograft models is associated with anti-tumor activity in the clinical setting. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vivo tumor xenograft models The in vitro effect of the compounds according to the invention can be demonstrated in the following assays:

Using a Scintillation Proximity Assay (SPA) format, the murine Aurora Kinase 1 (mAur1) and murine Aurora Kinase 2 (mAur2) biochemical assay measures the ability of mAur2 to phosphorylate the substrate, biotinylated Peptide 830 (DRT, Protein Sciences). Once radiolabeled by the enzyme, the biotinylated substrate is captured on streptavidin-coated SPA beads and the radioactivity, in proximity to the SPA beads, is measured. For the generation of $IC_{50}$ curves, the reaction was performed in 96-well isoplates (Wallac 1450-514) under the following conditions: a 10 mM stock solution of compound (in 100% dimethylsulfoxide; DMSO) was diluted 10 fold in 100% DMSO. Compounds were then serially diluted, 1:5, for an eight point dose curve, in 100% DMSO. A volume of 1 µL of the diluted compound was added to the reaction buffer that consisted of 25 mM HEPES pH 7.5, 1 mM $MnCl_2$, 1 mM $MgCl_2$, 1 mM DTT, 0.01% Tween20. A mixture with a final concentration per well of 1 µM cold ATP, 0.1 µCi $^{33}$P-ATP (Amersham AH9968) and 1 µM biotinylated Peptide 830 was then added. The reaction was initiated with the addition of either recombinant, GST-tagged mAur 1 (amino acids 67-345) that was co-expressed with human INCENP (amino acids 704-919) (DRT, Protein Sciences) at a final concentration of 12 nM or N-terminal His-tagged mAur2 (amino acids 98-395; DRT, Protein Sciences) at a final concentration of 20 nM. The final reaction volume in each well was 100 µL and the final compound concentration ranged from 10 µM-128 µM in 1% DMSO. The reaction mixture was allowed to incubate for 1-2 hours with gentle agitation at 25° C. To terminate the reaction, streptavidin-coated SPA beads (Amersham RPNQ0007; 50 µL of 0.5 mg beads dissolved in 165 mM EDTA) were then added to each well and incubation proceeded for an additional 15 minutes at 25° C. The plate was then centrifuged for ten minutes at 2000 rpm. Phosphorylation of the peptide substrate was measured using a Wallac 1450 Microbeta Plus Liquid Scintillation Counter. Using these procedures, compounds of Examples 1, 6, 8, 9, 14, 16, 17, 22, 23, 24, 25, 26, 45, 45, 48, 39, 40, 42, 47, 48, 49, 50, 55, 60, 71, 72, 73, 74, 75, 76, 80, 81, 85, 89, 90, 91, 92, 93, 96, 101, 102, 105, 106, 107, 108, 110, 111, 112, 113, 115, 116, 117, 119, and 120 demonstrate IC50s less then 0.1 µM in both the Aurora 1 and Aurora 2 murine biochemical assays.

To determine the ability of compounds to inhibit Aurora Kinase 1 activity in cells, a capture ELISA measuring Aurora Kinase 1 autophosphorylation was developed in HT29 colon carcinoma cells (Yasui Y, et al 2004). Briefly, 15,000 cells/well were seeded in a 96-well collagen coated plates in RPMI+10% FBS and incubated at 37° C. in 5% $CO_2$ overnight. The following day, the cells were treated with 166 nM nacadazole compounds for 24 hours at 37° C. Synchronized cells were further treated with compounds for 2 hours. Compound dilutions were prepared from 0.1 mM DMSO stocks such that 1.1 µL of each dilution was added to obtain a final concentration ranging from 10 µM to 13 nM in one-third log steps. Following compound treatment, plates were centrifuged at 1000 rpm for 2 minutes and washed twice with 100 µL of cold sterile TBS. Cells were then lysed (100 µL of 150 mM NaCl, 20 mM Tris, pH 7.5, 1 mM EDTA, 1 mM EGTA, 1% Triton-x-100 plus protease and phosphatase inhibitors) by shaking at 4° C. for 1 hour. Cell lysates were transferred to plates pre-coated with anti-phospho mAur1 (Rockland, 600-401-677) and blocked with 5% blocker A in TBS from Meso Scale Discovery. After incubating for 1 hour at RT, plates were washed with 300 µL of TBST for a total of three times. The supernatant was removed and replaced with 50 µL of diluted primary antibody (anti-Aurora Kinase 1, Pharmingen, 611083) at 1:1000 in 2% blocker A in TBS and incubated at room temperature for 1 hour. The antibody buffer was removed from each well and washed three times with 300 µL of cold TBS-T (50 µM Tris pH 8.0, 138 mM NaCl, 2.7 mM KCL, 0.05% Tween 20). The wash buffer was replaced with 50 µL of secondary antibody (Sulfa TAG anti-mouse, Meso Scale Discovery) at 1:1000 in 2% blocker A and incubated at room temperature for 1 hour. For the final readout with the Sector 6000, 150 µL of reading buffer T was added and the plates were read immediately. Using this procedure, compounds of Examples 10, 17, 20, 31, 32, 35, 47, 72, and 102 demonstrate an IC50 less then 1 µM.

B. Operative Examples Relating to Pharmaceutical Compositions

The compounds according to the invention can be converted into pharmaceutical preparations as follows:

Tablet:

Composition:

100 mg of the compound of Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is molded using a customary tablet press (tablet format, see above). The molding force applied is typically 15 kN.

Suspension for Oral Administration:

Composition:

1000 mg of the compound of Example 1, 1000 mg of ethanol (96%), 400 mg of Rhodigel (xanthan gum from FMC, Pennsylvania, USA) and 99 g of water.

A single dose of 100 mg of the compound according to the invention is provided by 10 ml of oral suspension.

Preparation:

The Rhodigel is suspended in ethanol and the active component is added to the suspension. The water is added with stirring. Stirring is continued for about 6 h until the swelling of the Rhodigel is complete.

What is claimed is:

1. A compound of formula (I)

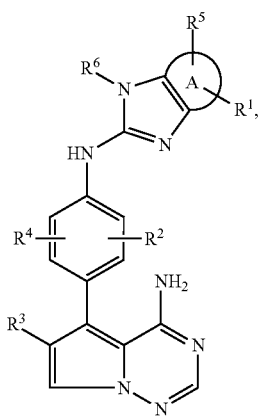

(I)

wherein

The A ring denotes a 5 to 7 membered aryl, heteroaryl, heterocyclic or cycloalkyl ring wherein the heteroaryl or heterocyclic rings include 1 to 3 heteroatoms selected from O, N or S;

$R^1$ is selected from the group consisting of hydrogen, halo, alkyl, trifluoromethyl, hydroxy, alkoxy, alkoxyalkyl, trifluoromethoxy, phenyloxy, halophenyloxy, methylphenyloxy, alkoxyphenyl, alkylphenyl, alkoxyalkylphenyl, halothiophenyl, alkylcarbonyl, nitro, cyano, carboxyl, alkoxycarbonyl, benzoyl, alkylamino, alkylaminocarbonyl, alkylaminosulfonyl, cycloalkylamino, cycloakylalkylamino, benzylamino, alkoxyalkylamino, and heterocyclyl, or $R^1$ is a group

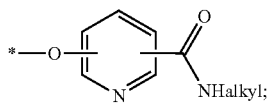

or $R^1$ and $R^5$ together with the carbon atoms to which they are attached, form a 1,3-dioxolane or 1,4-dioxane ring, which can optionally be substituted with 1, 2, or 3 halo;

$R^2$ is hydrogen, halo or methyl;

$R^3$ is

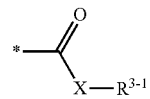

wherein $R^{3-1}$ is hydrogen, alkyl, trifluoroethyl, alkoxyalkyl, cycloalkyl, cycloalkylalkyl, heterocyclylalkyl, dialkylaminoalkyl, hydroxycycloalkyl, and X is —O—, —NH— or —N(alkyl)-, or wherein X and R3-1 are taken together to form a heterocyclyl ring optionally substituted with alkyl, carboxamide, alkoxyalkyl, or dialkylamino;

$R^4$ is hydrogen or halo;

$R^5$ is hydrogen, halo, or alkyl; and $R^6$ is hydrogen or alkyl;

or a pharmaceutically acceptable salt thereof.

2. The compound of claim 1, wherein X is —O—.

3. The compound of claim 1, wherein X is —NH—.

4. The compound of claim 1, wherein $R^{3-1}$ is trifluoroethyl.

5. The compound of claim 1, wherein X and $R^{3-1}$ are taken together to form a heterocyclyl ring optionally substituted with alkyl, carboxamide, alkoxyalkyl, or dialkylamino.

6. The compound of claim 1, wherein $R^2$ is hydrogen and $R^4$ is halogen.

7. The compound of claim 6, wherein $R^4$ is fluorine.

8. The compound of claim 1, wherein $R^6$ is hydrogen.

9. The compound of claim 1 having formula (Ia):

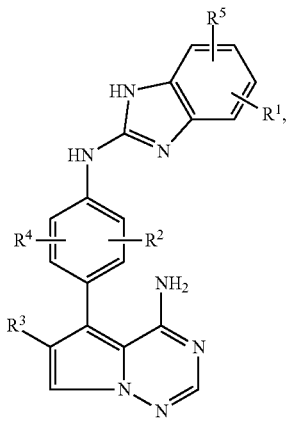

(Ia)

wherein $R^1$ is selected from the group consisting of hydrogen, halo, alkyl, trifluoromethyl, hydroxy, alkoxy, trifluoromethoxy, alkylcarbonyl, cyano, carboxyl, alkoxycarbonyl, alkylaminocarbonyl, alkylaminosulfonyl, and heterocyclyl, or R¹ is a group

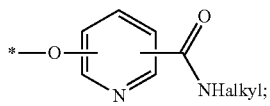

or R¹ and R⁵ together with the carbon atoms to which they are attached, form a 1,3-dioxolane or 1,4-dioxane ring, which can optionally be substituted with 1, 2, or 3 halo;
R² is hydrogen, halo or methyl;
R³ is

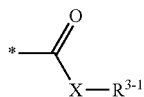

wherein R³⁻¹ is alkyl or trifluoroethyl, and X is O or —NH—;
R⁴ is hydrogen or halo;
R⁵ is hydrogen, halo, alkyl, or alkoxy;
or a pharmaceutically acceptable salt thereof.

10. A compound having the formula:
4-amino-5-[4-(1H-benzimidazol-2-ylamino)phenyl]-N-(2,2,2-trifluoroethyl)pyrrolo[2,1-f][1,2,4]triazine-6-carboxamide;
4-amino-5-{4-[(5-cyano-1H-benzimidazol-2-yl)amino]phenyl}-N-(2,2,2-trifluoroethyl)pyrrolo[2,1-f][1,2,4]triazine-6-carboxamide;
4-amino-5-{4-[(7-hydroxy-1H-benzimidazol-2-yl)amino]phenyl}-N-(2,2,2-trifluoroethyl)pyrrolo[2,1-f][1,2,4]triazine-6-carboxamide;
4-amino-5-{4-[(6-chloro-1H-benzimidazol-2-yl)amino]phenyl}-N-(2,2,2-trifluoroethyl)pyrrolo[2,1-f][1,2,4]triazine-6-carboxamide;
4-amino-N-(2,2,2-trifluoroethyl)-5-(4-{[6-(trifluoromethyl)-1H-benzimidazol-2-yl]amino}phenyl)pyrrolo[2,1-f][1,2,4]triazine-6-carboxamide;
4-amino-5-{4-[(5,7-difluoro-1H-benzimidazol-2-yl)amino]phenyl}-N-(2,2,2-trifluoroethyl)pyrrolo[2,1-f][1,2,4]triazine-6-carboxamide;
4-amino-5-{4-[(6-fluoro-1H-benzimidazol-2-yl)amino]phenyl}-N-(2,2,2-trifluoroethyl)pyrrolo[2,1-f][1,2,4]triazine-6-carboxamide;
4-amino-5-{4-[(6-methoxy-1H-benzimidazol-2-yl)amino]phenyl}-N-(2,2,2-trifluoroethyl)pyrrolo[2,1-f][1,2,4]triazine-6-carboxamide;
4-amino-5-{4-[(6-bromo-1H-benzimidazol-2-yl)amino]phenyl}-N-(2,2,2-trifluoroethyl)pyrrolo[2,1-f][1,2,4]triazine-6-carboxamide;
4-amino-5-{4-[(6-tert-butyl-1H-benzimidazol-2-yl)amino]phenyl}-N-(2,2,2-trifluoroethyl)pyrrolo[2,1-f][1,2,4]triazine-6-carboxamide;
4-amino-5-{4-[(6-benzoyl-1H-benzimidazol-2-yl)amino]phenyl}-N-(2,2,2-trifluoroethyl)pyrrolo[2,1-f][1,2,4]triazine-6-carboxamide;
4-amino-5-{4-[(5,6-dichloro-1H-benzimidazol-2-yl)amino]phenyl}-N-(2,2,2-trifluoroethyl)pyrrolo[2,1-f][1,2,4]triazine-6-carboxamide;
4-amino-5-{4-[(6-chloro-5-fluoro-1H-benzimidazol-2-yl)amino]phenyl}-N-(2,2,2-trifluoroethyl)pyrrolo[2,1-f][1,2,4]triazine-6-carboxamide;
4-amino-5-{4-[(5,6-difluoro-1H-benzimidazol-2-yl)amino]phenyl}-N-(2,2,2-trifluoroethyl)pyrrolo[2,1-f][1,2,4]triazine-6-carboxamide;
4-amino-5-{4-[(6,7-dimethyl-1H-benzimidazol-2-yl)amino]phenyl}-N-(2,2,2-trifluoroethyl)pyrrolo[2,1-f][1,2,4]triazine-6-carboxamide;
4-amino-5-[4-(1H-thieno[3,4-d]imidazol-2-ylamino)phenyl]-N-(2,2,2-trifluoroethyl)pyrrolo[2,1-f][1,2,4]triazine-6-carboxamide;
4-amino-5-{4-[(2,2-difluoro-5H-[1,3]dioxolo[4,5-f]benzimidazol-6-yl)amino]phenyl}-N-(2,2,2-trifluoroethyl)pyrrolo[2,1-f][1,2,4]triazine-6-carboxamide;
4-amino-5-[4-(3H-imidazo[4,5-b]pyridin-2-ylamino)phenyl]-N-(2,2,2-trifluoroethyl)pyrrolo[2,1-f][1,2,4]triazine-6-carboxamide;
4-amino-5-(4-{[6-(4-methoxyphenyl)-1H-benzimidazol-2-yl]amino}phenyl)-N-(2,2,2-trifluoroethyl)pyrrolo[2,1-f][1,2,4]triazine-6-carboxamide;
4-amino-5-{4-[(5-pyrrolidin-1-yl-3H-imidazo[4,5-b]pyridin-2-yl)amino]phenyl}-N-(2,2,2-trifluoroethyl)pyrrolo[2,1-f][1,2,4]triazine-6-carboxamide;
4-amino-5-[4-(9H-purin-8-ylamino)phenyl]-N-(2,2,2-trifluoroethyl)pyrrolo[2,1-f][1,2,4]triazine-6-carboxamide;
4-amino-5-{4-[(7-methyl-1H-benzimidazol-2-yl)amino]phenyl}-N-(2,2,2-trifluoroethyl)pyrrolo[2,1-f][1,2,4]triazine-6-carboxamide;
4-amino-5-{4-[(6-nitro-1H-benzimidazol-2-yl)amino]phenyl}-N-(2,2,2-trifluoroethyl)pyrrolo[2,1-f][1,2,4]triazine-6-carboxamide;
4-amino-5-{4-[(5-methoxy-3H-imidazo[4,5-b]pyridin-2-yl)amino]phenyl}-N-(2,2,2-trifluoroethyl)pyrrolo[2,1-f][1,2,4]triazine-6-carboxamide;
4-amino-5-{4-[(6-iodo-3H-imidazo[4,5-b]pyridin-2-yl)amino]phenyl}-N-(2,2,2-trifluoroethyl)pyrrolo[2,1-f][1,2,4]triazine-6-carboxamide;
4-amino-5-{4-[(5-chloro-3H-imidazo[4,5-b]pyridin-2-yl)amino]phenyl}-N-(2,2,2-trifluoroethyl)pyrrolo[2,1-f][1,2,4]triazine-6-carboxamide;
4-amino-5-{4-[(6-phenoxy-1H-benzimidazol-2-yl)amino]phenyl}-N-(2,2,2-trifluoroethyl)pyrrolo[2,1-f][1,2,4]triazine-6-carboxamide;
4-amino-5-{4-[(5-methyl-3H-imidazo[4,5-b]pyridin-2-yl)amino]phenyl}-N-(2,2,2-trifluoroethyl)pyrrolo[2,1-f][1,2,4]triazine-6-carboxamide;
4-amino-5-(4-{[6-(4-fluorophenoxy)-1H-benzimidazol-2-yl]amino}phenyl)-N-(2,2,2-trifluoroethyl)pyrrolo[2,1-f][1,2,4]triazine-6-carboxamide;
4-amino-5-{4-[(6-methyl-3H-imidazo[4,5-b]pyridin-2-yl)amino]phenyl}-N-(2,2,2-trifluoroethyl)pyrrolo[2,1-f][1,2,4]triazine-6-carboxamide;
4-amino-N-(2,2,2-trifluoroethyl)-5-(4-{[6-(trifluoromethoxy)-1H-benzimidazol-2-yl]amino}phenyl)pyrrolo[2,1-f][1,2,4]triazine-6-carboxamide;
4-amino-5-{4-[(7-fluoro-6-phenoxy-1H-benzimidazol-2-yl)amino]phenyl}-N-(2,2,2-trifluoroethyl)pyrrolo[2,1-f][1,2,4]triazine-6-carboxamide;
4-amino-5-{4-[(5-ethoxy-1H-benzimidazol-2-yl)amino]phenyl}-N-(2,2,2-trifluoroethyl)pyrrolo[2,1-f][1,2,4]triazine-6-carboxamide;
4-amino-5-(4-{[7-fluoro-6-(4-methylphenoxy)-1H-benzimidazol-2-yl]amino}phenyl)-N-(2,2,2-trifluoroethyl)pyrrolo[2,1-f][1,2,4]triazine-6-carboxamide;
4-amino-5-(4-{[7-fluoro-6-(4-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-{4-[(1-methyl-1H-benzimidazol-2-yl)amino]phenyl}-N-(2,2,2-trifluoroethyl)pyrrolo[2,1-f][1,2,4]triazine-6-carboxamide;

4-amino-5-{4-[(7-fluoro-6-pyrrolidin-1-yl-1H-benzimidazol-2-yl)amino]phenyl}-N-(2,2,2-trifluoroethyl)pyrrolo[2,1-f][1,2,4]triazine-6-carboxamide;

4-amino-5-{4-[(5-phenoxy-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-(4-{[7-fluoro-6-(2-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(3-fluorophenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(2-methylphenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(3-methylphenoxy)-1H-benzimidazol-2-yl]amino}phenyl)-N-(2,2,2-trifluoroethyl)pyrrolo[2,1-f][1,2,4]triazine-6-carboxamide;

4-amino-5-(4-{[7-fluoro-6-(isopropylamino)-1H-benzimidazol-2-yl]amino}phenyl)-N-(2,2,2-trifluoroethyl)pyrrolo[2,1-f][1,2,4]triazine-6-carboxamide trifluoroacetate;

5-{4-[(6-acetyl-1-methyl-1H-benzimidazol-2-yl)amino]phenyl}-4-amino-N-(2,2,2-trifluoroethyl)pyrrolo[2,1-f][1,2,4]triazine-6-carboxamide;

4-amino-5-{4-[(6-methyl-9H-purin-8-yl)amino]phenyl}-N-(2,2,2-trifluoroethyl)pyrrolo[2,1-f][1,2,4]triazine-6-carboxamide;

4-amino-5-{4-[(5-morpholin-4-yl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-(4-{[5-(cyclobutylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(cyclohexylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(3,4-dimethylphenoxy)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[(3-fluorophenyl)thio]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-[4-({5-[(cyclohexylmethyl)amino]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-(4-{[5-(isobutylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-({5-[(2-methoxyethyl)amino]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-(4-{[5-(tert-butylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(propylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[(2-methoxyethyl)(methyl)amino]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-5-(4-{[5-(cyclopropylamino)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-(4-{[5-(3,3-difluoropyrrolidin-1-yl)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-{4-[(5,7-difluoro-1H-benzimidazol-2-yl)amino]-3-fluorophenyl}-N-(2,2,2-trifluoroethyl)pyrrolo[2,1-f][1,2,4]triazine-6-carboxamide;

4-amino-5-{4-[(2,2-difluoro-5H-[1,3]dioxolo[4,5-f]benzimidazol-6-yl)amino]-3-fluorophenyl}-N-(2,2,2-trifluoroethyl)pyrrolo[2,1-f][1,2,4]triazine-6-carboxamide;

4-amino-5-{4-[(6-chloro-1H-benzimidazol-2-yl)amino]-3-fluorophenyl}-N-(2,2,2-trifluoroethyl)pyrrolo[2,1-f][1,2,4]triazine-6-carboxamide;

4-amino-5-{3-fluoro-4-[(5-methyl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-{3-fluoro-4-[(5-morpholin-4-yl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-{3-fluoro-4-[(5-pyrrolidin-1-yl-3H-imidazo[4,5-b]pyridin-2-yl)amino]phenyl}-N-(2,2,2-trifluoroethyl)pyrrolo[2,1-f][1,2,4]triazine-6-carboxamide;

4-amino-5-[3-fluoro-4-(3H-imidazo[4,5-b]pyridin-2-ylamino)phenyl]-N-(2,2,2-trifluoroethyl)pyrrolo[2,1-f][1,2,4]triazine-6-carboxamide;

4-amino-5-{4-[(5-chloro-6-fluoro-1H-benzimidazol-2-yl)amino]-3-fluorophenyl}-N-(2,2,2-trifluoroethyl)pyrrolo[2,1-f][1,2,4]triazine-6-carboxamide;

4-amino-5-[3-fluoro-4-(1H-thieno[3,4-d]imidazol-2-ylamino)phenyl]-N-(2,2,2-trifluoroethyl)pyrrolo[2,1-f][1,2,4]triazine-6-carboxamide;

4-amino-5-{4-[(5-benzoyl-1H-benzimidazol-2-yl)amino]-3-fluorophenyl}-N-(2,2,2-trifluoroethyl)pyrrolo[2,1-f][1,2,4]triazine-6-carboxamide;

4-amino-5-[3-fluoro-4-(1H-imidazo[4,5-c]pyridin-2-ylamino)phenyl]-N-(2,2,2-trifluoroethyl)pyrrolo[2,1-f][1,2,4]triazine-6-carboxamide;

4-amino-5-{3-fluoro-4-[(7-methyl-1H-benzimidazol-2-yl)amino]phenyl}-N-(2,2,2-trifluoroethyl)pyrrolo[2,1-f][1,2,4]triazine-6-carboxamide;

4-amino-5-{4-[(5,7-difluoro-1H-benzimidazol-2-yl)amino]phenyl}pyrrolo[2,1-f][1,2,4]triazine-6-carboxylic acid;

4-amino-N-(tert-butyl)-5-{4-[(5,7-difluoro-1H-benzimidazol-2-yl)amino]phenyl}pyrrolo[2,1-f][1,2,4]triazine-6-carboxamide;

4-amino-5-{4-[(5,7-difluoro-1H-benzimidazol-2-yl)amino]phenyl}-N-ethylpyrrolo[2,1-f][1,2,4]triazine-6-carboxamide;

4-amino-5-{4-[(5,7-difluoro-1H-benzimidazol-2-yl)amino]phenyl}-N,N-dimethylpyrrolo[2,1-f][1,2,4]triazine-6-carboxamide;

4-amino-5-{4-[(5,7-difluoro-1H-benzimidazol-2-yl)amino]phenyl}-N-(2-methoxyethyl)pyrrolo[2,1-f][1,2,4]triazine-6-carboxamide;

5-{4-[(5,7-difluoro-1H-benzimidazol-2-yl)amino]phenyl}-6-(morpholin-4-ylcarbonyl)pyrrolo[2,1-f][1,2,4]triazin-4-amine;

4-amino-N-cyclobutyl-5-{4-[(5,7-difluoro-1H-benzimidazol-2-yl)amino]phenyl}pyrrolo[2,1-f][1,2,4]triazine-6-carboxamide;

4-amino-N-cyclohexyl-5-{4-[(5,7-difluoro-1H-benzimidazol-2-yl)amino]phenyl}pyrrolo[2,1-f][1,2,4]triazine-6-carboxamide;

4-amino-5-{4-[(5,7-difluoro-1H-benzimidazol-2-yl)amino]phenyl}-N-(3-methylbutyl)pyrrolo[2,1-f][1,2,4]triazine-6-carboxamide;

4-amino-N-(cyclopropylmethyl)-5-{4-[(5,7-difluoro-1H-benzimidazol-2-yl)amino]phenyl}pyrrolo[2,1-f][1,2,4]triazine-6-carboxamide;

1-[(4-amino-5-{4-[(5,7-difluoro-1H-benzimidazol-2-yl)amino]phenyl}pyrrolo[2,1-f][1,2,4]triazin-6-yl)carbonyl]piperidine-4-carboxamide;

4-amino-5-{4-[(5,7-difluoro-1H-benzimidazol-2-yl)amino]phenyl}-N-(3-pyrrolidin-1-ylpropyl)pyrrolo[2,1-f][1,2,4]triazine-6-carboxamide;

4-amino-5-{4-[(5,7-difluoro-1H-benzimidazol-2-yl)amino]phenyl}-N-(3-morpholin-4-ylpropyl)pyrrolo[2,1-f][1,2,4]triazine-6-carboxamide;

4-amino-5-{4-[(5,7-difluoro-1H-benzimidazol-2-yl)amino]phenyl}-N-[2-(dimethylamino)ethyl]pyrrolo[2,1-f][1,2,4]triazine-6-carboxamide;

4-amino-N-cyclopentyl-5-{4-[(5,7-difluoro-1H-benzimidazol-2-yl)amino]phenyl}pyrrolo[2,1-f][1,2,4]triazine-6-carboxamide;

4-amino-5-{4-[(5,7-difluoro-1H-benzimidazol-2-yl)amino]phenyl}-N-(2-ethoxyethyl)pyrrolo[2,1-f][1,2,4]triazine-6-carboxamide;

4-amino-5-{4-[(5,7-difluoro-1H-benzimidazol-2-yl)amino]phenyl}-N-(2-hydroxycyclohexyl)pyrrolo[2,1-f][1,2,4]triazine-6-carboxamide;

4-amino-5-{4-[(5,7-difluoro-1H-benzimidazol-2-yl)amino]phenyl}-N-(tetrahydro-2H-pyran-4-ylmethyl)pyrrolo[2,1-f][1,2,4]triazine-6-carboxamide;

4-amino-5-{4-[(5,7-difluoro-1H-benzimidazol-2-yl)amino]phenyl}-N-ethyl-N-methylpyrrolo[2,1-f][1,2,4]triazine-6-carboxamide;

4-amino-5-{4-[(5,7-difluoro-1H-benzimidazol-2-yl)amino]phenyl}-N-ethyl-N-isopropylpyrrolo[2,1-f][1,2,4]triazine-6-carboxamide;

5-{4-[(5,7-difluoro-1H-benzimidazol-2-yl)amino]phenyl}-6-{[2-(methoxymethyl)pyrrolidin-1-yl]carbonyl}pyrrolo[2,1-f][1,2,4]triazin-4-amine;

4-amino-5-{4-[(5,7-difluoro-1H-benzimidazol-2-yl)amino]phenyl}-N-isopropyl-N-methylpyrrolo[2,1-f][1,2,4]triazine-6-carboxamide;

4-amino-5-{4-[(5,7-difluoro-1H-benzimidazol-2-yl)amino]phenyl}-N-methyl-N-propylpyrrolo[2,1-f][1,2,4]triazine-6-carboxamide;

4-amino-5-{4-[(5,7-difluoro-1H-benzimidazol-2-yl)amino]phenyl}-N-[2-(dimethylamino)ethyl]-N-methylpyrrolo[2,1-f][1,2,4]triazine-6-carboxamide;

5-{4-[(5,7-difluoro-1H-benzimidazol-2-yl)amino]phenyl}-6-{[(3R)-3-(dimethylamino)pyrrolidin-1-yl]carbonyl}pyrrolo[2,1-f][1,2,4]triazin-4-amine;

5-{4-[(5,7-difluoro-1H-benzimidazol-2-yl)amino]phenyl}-6-(pyrrolidin-1-ylcarbonyl)pyrrolo[2,1-f][1,2,4]triazin-4-amine;

4-amino-5-{4-[(5,7-difluoro-1H-benzimidazol-2-yl)amino]phenyl}-N-ethyl-N-propylpyrrolo[2,1-f][1,2,4]triazine-6-carboxamide;

5-{4-[(5,7-difluoro-1H-benzimidazol-2-yl)amino]phenyl}-6-[(4-methylpiperazin-1-yl)carbonyl]pyrrolo[2,1-f][1,2,4]triazin-4-amine;

4-[(4-amino-5-{4-[(5,7-difluoro-1H-benzimidazol-2-yl)amino]phenyl}pyrrolo[2,1-f][1,2,4]triazin-6-yl)carbonyl]piperazin-2-one;

4-amino-5-{4-[(5,7-difluoro-1H-benzimidazol-2-yl)amino]phenyl}-N-methyl-N-(tetrahydro-2H-pyran-4-ylmethyl)pyrrolo[2,1-f][1,2,4]triazine-6-carboxamide;

4-amino-5-{4-[(7-fluoro-6-phenoxy-1H-benzimidazol-2-yl)amino]phenyl}pyrrolo[2,1-f][1,2,4]triazine-6-carboxylic acid;

4-amino-5-{4-[(7-fluoro-6-phenoxy-1H-benzimidazol-2-yl)amino]phenyl}-N-methylpyrrolo[2,1-f][1,2,4]triazine-6-carboxamide;

4-amino-5-{4-[(7-fluoro-6-phenoxy-1H-benzimidazol-2-yl)amino]phenyl}-N-propylpyrrolo[2,1-f][1,2,4]triazine-6-carboxamide;

4-amino-5-{4-[(7-fluoro-6-phenoxy-1H-benzimidazol-2-yl)amino]phenyl}-N-isopropylpyrrolo[2,1-f][1,2,4]triazine-6-carboxamide;

4-amino-N-cyclopropyl-5-{4-[(7-fluoro-6-phenoxy-1H-benzimidazol-2-yl)amino]phenyl}pyrrolo[2,1-f][1,2,4]triazine-6-carboxamide;

4-amino-N-ethyl-5-{4-[(7-fluoro-6-phenoxy-1H-benzimidazol-2-yl)amino]phenyl}-N-methylpyrrolo[2,1-f][1,2,4]triazine-6-carboxamide;

5-{4-[(7-fluoro-6-phenoxy-1H-benzimidazol-2-yl)amino]phenyl}-6-(piperidin-1-ylcarbonyl)pyrrolo[2,1-f][1,2,4]triazin-4-amine;

5-{4-[(7-fluoro-6-phenoxy-1H-benzimidazol-2-yl)amino]phenyl}-6-(morpholin-4-ylcarbonyl)pyrrolo[2,1-f][1,2,4]triazin-4-amine;

4-amino-N-ethyl-5-{4-[(5-pyrrolidin-1-yl-3H-imidazo[4,5-b]pyridin-2-yl)amino]phenyl}pyrrolo[2,1-f][1,2,4]triazine-6-carboxamide;

4-amino-5-{4-[(7-fluoro-6-phenoxy-1H-benzimidazol-2-yl)amino]phenyl}-N-(2-methoxyethyl)pyrrolo[2,1-f][1,2,4]triazine-6-carboxamide;

4-amino-5-{4-[(7-fluoro-6-phenoxy-1H-benzimidazol-2-yl)amino]phenyl}-N-isobutylpyrrolo[2,1-f][1,2,4]triazine-6-carboxamide;

4-amino-N-cyclopentyl-5-{4-[(7-fluoro-6-phenoxy-1H-benzimidazol-2-yl)amino]phenyl}pyrrolo[2,1-f][1,2,4]triazine-6-carboxamide;

5-{4-[(7-fluoro-6-phenoxy-1H-benzimidazol-2-yl)amino]phenyl}-6-(pyrrolidin-1-ylcarbonyl)pyrrolo[2,1-f][1,2,4]triazin-4-amine;

4-amino-N-(cyclopropylmethyl)-5-{4-[(7-fluoro-6-phenoxy-1H-benzimidazol-2-yl)amino]phenyl}pyrrolo[2,1-f][1,2,4]triazine-6-carboxamide;

4-amino-5-(4-{[5-(4-methylphenyl)-3H-imidazo[4,5-b]pyridin-2-yl]amino}phenyl)-N-(2,2,2-trifluoroethyl)pyrrolo[2,1-f][1,2,4]triazine-6-carboxamide;

4-amino-5-[4-({5-[3-(methoxymethyl)phenyl]-3H-imidazo[4,5-b]pyridin-2-yl}amino)phenyl]-N-(2,2,2-trifluoroethyl)pyrrolo[2,1-f][1,2,4]triazine-6-carboxamide;

4-amino-N-(tert-butyl)-5-{4-[(6-chloro-3H-imidazo[4,5-b]pyridin-2-yl)amino]-3-fluorophenyl}pyrrolo[2,1-f][1,2,4]triazine-6-carboxamide;

4-amino-N-(tert-butyl)-5-{4-[(2,2-difluoro-5H-[1,3]dioxolo[4,5-f]benzimidazol-6-yl)amino]-3-fluorophenyl}pyrrolo[2,1-f][1,2,4]triazine-6-carboxamide;

4-amino-5-(4-{[5-(trifluoromethyl)-3H-imidazo[4,5-b]pyridin-2-yl]amino}phenyl)pyrrolo[2,1-f][1,2,4]triazine-6-carboxylic acid;

4-amino-N-(2,2,2-trifluoroethyl)-5-(4-{[5-(trifluoromethyl)-3H-imidazo[4,5-b]pyridin-2-yl]amino}phenyl)pyrrolo[2,1-f][1,2,4]triazine-6-carboxamide;

ethyl 4-amino-5-[4-(1H-benzimidazol-2-ylamino)phenyl]pyrrolo[2,1-f][1,2,4]triazine-6-carboxylate;

ethyl 4-amino-5-{4-[(5-methoxy-1H-benzimidazol-2-yl)amino]phenyl}pyrrolo[2,1-f][1,2,4]triazine-6-carboxylate;

or a pharmaceutically acceptable salt thereof.

11. A process for preparing a compound of claim 1, comprising

[A] reacting a compound of formula (II)

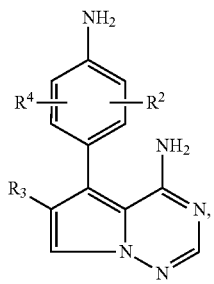
(II)

wherein $R^2$, $R^3$ and $R^4$ have the meaning indicated in claim 1, with a diamino compound of formula (III)

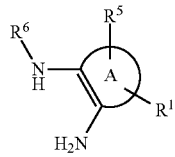
(III)

wherein A, $R^1$, $R^5$ and $R^6$ have the meaning indicated in claim 1, in the presence of thiocarbonyldiimidazole, followed by cyclization with a coupling agent; or

[B] coupling a compound of formula (II), wherein $R^2$, $R^3$ and $R^4$ have the meaning indicated in claim 1, with a 2-chlorobenzimidazole of formula (IV),

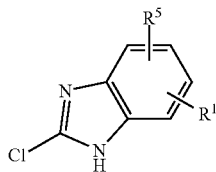
(IV)

wherein $R^1$ and $R^5$ have the meaning indicated in claim 1.

12. The process of claim 11, wherein the compound of formula (III), has the formula (IIIa)

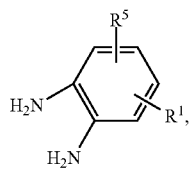
(IIIa)

wherein $R^1$ and $R^5$ have the meaning indicated in claim 1.

13. A pharmaceutical composition comprising a compound as defined in claim 1 and at least one pharmaceutically acceptable excipient.

14. A method of treating cancer of the breast, comprising administering to a mammal in need thereof an effective amount of a compound as defined in claim 1.

* * * * *